United States Patent
Gallop

(10) Patent No.: US 8,058,260 B2
(45) Date of Patent: Nov. 15, 2011

(54) 2'-C-METHYL-RIBOFURANOSYL CYTIDINE PRODRUGS, PHARMACEUTICAL COMPOSITIONS AND USES THEREOF

(75) Inventor: Mark A. Gallop, Santa Clara, CA (US)

(73) Assignee: XenoPort, Inc., Santa Clara, CA (US)

( * ) Notice: Subject to any disclaimer, the term of this patent is extended or adjusted under 35 U.S.C. 154(b) by 1129 days.

(21) Appl. No.: 11/752,214

(22) Filed: May 22, 2007

(65) Prior Publication Data

US 2007/0270374 A1    Nov. 22, 2007

Related U.S. Application Data

(60) Provisional application No. 60/808,360, filed on May 22, 2006.

(51) Int. Cl.
*A61K 31/70* (2006.01)
*C07H 19/067* (2006.01)

(52) U.S. Cl. ........................ 514/49; 536/28.5; 536/28.51

(58) Field of Classification Search ........................ None
See application file for complete search history.

(56) References Cited

U.S. PATENT DOCUMENTS

| | | | |
|---|---|---|---|
| 3,845,770 A | 11/1974 | Theeuwes et al. | |
| 3,916,899 A | 11/1975 | Theeuwes et al. | |
| 5,698,155 A | 12/1997 | Grosswald et al. | |
| 6,812,219 B2 * | 11/2004 | LaColla et al. | 514/49 |
| 6,914,054 B2 | 7/2005 | Sommadossi et al. | |
| 7,101,861 B2 * | 9/2006 | Sommadossi et al. | 514/49 |
| 7,105,493 B2 * | 9/2006 | Sommadossi et al. | 514/42 |
| 7,148,206 B2 * | 12/2006 | Sommadossi et al. | 514/45 |
| 7,163,929 B2 * | 1/2007 | Sommadossi et al. | 514/49 |
| 7,192,936 B2 * | 3/2007 | LaColla et al. | 514/49 |
| 7,429,572 B2 * | 9/2008 | Clark | 514/49 |
| 7,582,618 B2 * | 9/2009 | Sommadossi et al. | 514/49 |
| 7,632,821 B2 * | 12/2009 | Butora et al. | 514/43 |
| 7,645,745 B2 * | 1/2010 | Sarma | 514/49 |
| 2004/0077587 A1 | 4/2004 | Sommadossi et al. | |
| 2004/0142857 A1 | 7/2004 | Gallop et al. | |

FOREIGN PATENT DOCUMENTS

| WO | WO 01/20331 | 3/2001 |
|---|---|---|
| WO | WO 2004/002999 | 1/2004 |
| WO | WO 2004/003000 | 1/2004 |

OTHER PUBLICATIONS

Alderman, A review of cellulose ethers in hydrophilic matrices for oral controlled release dosage forms, *Int. J. Pharm. Tech. & Prod. Mfg.*, 1984, 5(3), 1-9.
Balimane et al., Involvement of multiple transporters in the oral absorption of nucleoside analogues, *Adv. Drug Delivery Rev.* 1999, 39, 183-209.
Bamba et al., Release mechanisms in gelforming sustained release preparations, *Int. J. Pharm.*, 1979, 2, 307-315.
Boyer, et al., Pathogenesis, diagnosis and management of hepatitis C, *J. Hepatol.* 2000, 32, 98-112.

Clark et al., Design, synthesis and antiviral activity of 2'-deoxy-2'-fluor-2'-c'-methylcytidine, a potent inhibitor of hepatitis C virus replication, *J. Med. Chem.* 2005, 48, 5504-5508.
Di Bisceglie et al., The unmet challenges, Scientific American Oct. 1999, 80-85.
During, et al., Controlled release of dopamine from a polymeric brain implant: in vivo characterization, 1989, *Ann. Neurol.* 25, 351.
Goodson, in "Medical Applications of Controlled Release," *supra*, vol. 2, pp. 1.15-138 (1984).
Howard et al. Intracerebral drug delivery in rats with lesion-induced memory deficits, *J. Neurosurg.* 71,105-112.
Langer, R. , (1983). Chemical and physical structure of polymers as carriers for controlled release of bioactive agents: a review. JMS Rev Macromol Chem. Phys. C23(1), 61-126.
Langer, 1990, New methods of drug delivery Science 249,1527-1533.
Leibach, et al., Peptide transporter in the intestine and kidney, *Annu. Rev. Nutr.* 1996, 16, 99-119.
Levy, et al., Inhibition of calcification of bioprosthetic heart valves by local controlled—release diphosphonate Science 228, 190-192.
Pierra et al., *Nucleosides, Nucleotides* 2005, 24, 767-770.
Pierra et al., *J. Med. Chem.* 2006, 49, 6614-6620.
Rice, C. M., Flaviviridae: The viruses and their replication. In: *Fields Virology*, Editors: Fields, B. N., Knipe, D. M., and Howley, P. M., Lippincott-Raven Publishers, Philadelphia, Pa., Chapter 30, 931-959, 1996.
Saudek et al., A preliminary trial of the programmable implantable medication system for insulin delivery ,1989, *N. Engl. J Med.* 321, 574-579.
Sefton, 1987, Implantable Pumps, *CRC Crit Ref Biomed Eng.* 14, 201-240.
Verma et al., Osmotically Controlled Oral Drug Delivery, *Drug Dev. Ind. Pharm.*, 2000, 26, 695-708.
Kolor, Patient Education and Treatment Strategies Implemented at a Pharmacist-Managed Hepatitis C Virus Clinic, *Pharmacother.* (2005), 25(9): 1230-1241.
Moreno-Otero, et al., Is interferon-beta an alternative treatment for chronic hepatitis C?, *W. J. Gastroenterol.* (2006), 12(17): 2730-2736.
Moriyama, et al., Treatment of interferon-α for chronic hepatitis C, *Expert Opin. Pharmacother.* (2006), 7(9): 1163-1179.

* cited by examiner

*Primary Examiner* — Lawrence E Crane
(74) *Attorney, Agent, or Firm* — Dorsey & Whitney LLP

(57) ABSTRACT

The present disclosure provides 2'-C-methyl-ribofuranosyl cytidine prodrugs, methods of making 2'-C-methyl-ribofuranosyl cytidine prodrugs, pharmaceutical compositions of 2'-C-methyl-ribofuranosyl cytidine prodrugs, and methods of using 2'-C-methyl-ribofuranosyl cytidine prodrugs and pharmaceutical compositions thereof to treat viral diseases such as hepatitis C.

54 Claims, 8 Drawing Sheets

(XVII) → (XXII)

2'-C-METHYL-RIBOFURANOSYL CYTIDINE PRODRUGS, PHARMACEUTICAL COMPOSITIONS AND USES THEREOF

This application claims priority to U.S. Provisional Application Ser. No. 60/808,360 filed May 22, 2006, which is incorporated by reference in its entirety.

TECHNICAL FIELD

The present disclosure relates generally to 2'-C-methyl-ribofuranosyl cytidine prodrugs, methods of making 2'-C-methyl-ribofuranosyl cytidine prodrugs, pharmaceutical compositions of 2'-C-methyl-ribofuranosyl cytidine prodrugs, and methods of using 2'-C-methyl-ribofuranosyl cytidine prodrugs and pharmaceutical compositions thereof to treat diseases or disorders such as hepatitis C.

BACKGROUND

The hepatitis C virus (HCV) is the leading cause of chronic liver disease worldwide. (Boyer et al., *J. Hepatol.* 2000, 32, 98-112). HCV causes a slow growing viral infection and is the major cause of cirrhosis and hepatocellular carcinoma (Di Besceglie et al., *Scientific American* 1999, October, 80-85). An estimated 170 million persons are infected with HCV worldwide. Cirrhosis caused by chronic hepatitis C infection accounts for 8,000-12,000 deaths per year in the United States, and HCV infection is the leading indication for liver transplant.

HCV is known to cause at least 80% of posttransfusion hepatitis and a substantial proportion of sporadic acute hepatitis. Preliminary evidence also implicates HCV in many cases of "idiopathic" chronic hepatitis, "cryptogenic" cirrhosis, and probably hepatocellular carcinoma unrelated to other hepatitis viruses, such as Hepatitis B Virus (HBV). A small proportion of healthy persons appear to be chronic HCV carriers, varying with geography and other epidemiological factors. The numbers may substantially exceed those for HBV, though information is still preliminary; how many of these persons have subclinical chronic liver disease is unclear.

HCV has been classified as a member of the virus family Flaviviridae that includes the genera flaviviruses, pestiviruses, and hapaceiviruses, which includes hepatitis C viruses (Rice, C. M., *Flaviviridae: The viruses and their replication. In: Fields Virology*, Editors: Fields, B. N., Knipe, D. M., and Howley, P. M., Lippincott-Raven Publishers, Philadelphia, Pa., Chapter 30, 931-959, 1996). HCV is an enveloped virus containing a positive-sense single-stranded RNA genome of approximately 9.4 kb. Currently, there are two primary antiviral compounds, Ribavirin and interferon-alpha, which are used for the treatment of chronic HCV infections in humans. The non-structural protein NS5B has been described as an RNA-dependent RNA polymerase that is required for viral replication. This polymerase is an essential component in the HCV replication complex and therefore is an excellent target for drug discovery.

Several 2'-modified nucleoside analogs with potent inhibitory activity against the HCV NS5B polymerase have been identified, including β-D-2'-C-methyl-ribofuranosyl cytidine (1) (e.g., see Sommadossi et al., U.S. Pat. No. 6,914,054 and references therein; and Clark et al., *J. Med. Chem.* 2005, 48, 5504-5508). Efforts to improve the oral bioavailability of (1) have resulted in the investigation of prodrug derivatives, including synthesis of compounds with acyl and/or α-aminoacyl moieties appended at one or more of the 5'-O, 3'-O, or N-4 positions of the ribonucleoside nucleus (e.g., see Pierra et al., *Nucleosides, Nucleotides* 2005, 24, 767-770; Pierra et al., *J. Med. Chem.* 2006, 49, 6614-6620; U.S. Application Publication No. 2004/0077587; International Publication No. WO 2004/002999; and International Application No. WO04/003000). One compound of particular interest is NM 283 (2), the 3'-O-L-valinyl ester of β-D-2'-C-methyl-ribofuranosyl cytidine, which shows good bioavailability in preclinical species and in humans (e.g., see Pierra et al., *J. Med. Chem.* 2006, 49, 6614-6620). NM 283 is currently undergoing clinical evaluation as a treatment for HCV, where significant antiviral activity has been demonstrated.

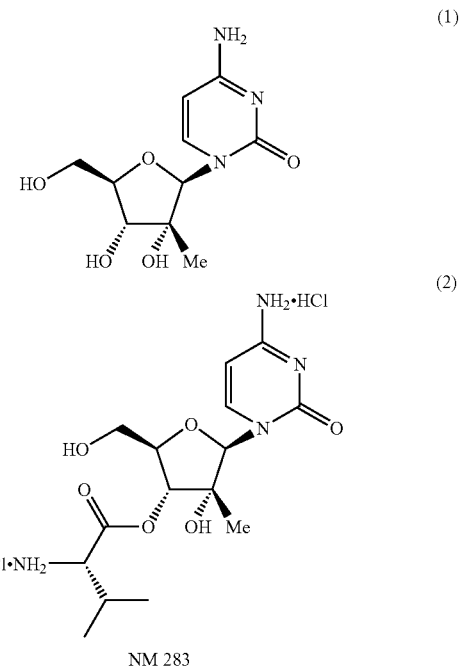

NM 283

One significant problem with oral administration of NM 283 or β-D-2'-C-methyl-ribofuranosyl cytidine is the gastrointestinal (GI) toxicity of the parent nucleoside analog which results in unpleasant side-effects in some patients such as nausea, vomiting and diarrhea. This toxicity may arise as a result of accumulation of the phosphorylated nucleoside analog within intestinal cells, and its incomplete selectivity for inhibition of the viral RNA polymerase relative to mammalian polymerase enzymes. Thus, there is a need for improved prodrugs of (1) having a superior safety and tolerability profile than NM 283 (2). Preferred prodrugs are sufficiently stable in the intestinal lumen and during transit across the enterocyte barrier so that little or no compound (1) is liberated within the intestinal cells themselves. This limits direct exposure of sensitive GI cells to toxic levels of (1). However, once the prodrug has entered the portal circulation and is delivered to the liver, cleavage to compound (1) via enzymatic, chemical, or a combination of enzymatic and chemical means should occur in order that a therapeutically effective concentration of (1) is provided to virally infected cells (hepatocytes).

SUMMARY

These and other needs are provided for by the disclosure herein of 2'-C-methyl-ribofuranosyl cytidine prodrugs, methods of making 2'-C-methyl-ribofuranosyl cytidine prodrugs, pharmaceutical compositions of 2'-C-methyl-ribofuranosyl cytidine prodrugs, and methods of using 2'-C-methyl-ribofuranosyl cytidine prodrugs and pharmaceutical compositions thereof to treat diseases or disorders such as hepatitis C.

In a first aspect, a compound of structural Formula (I) is provided:

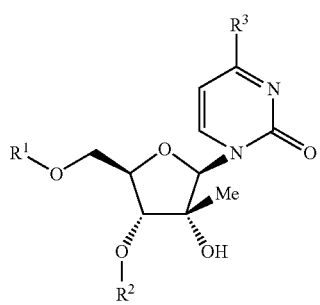

(I)

a pharmaceutically acceptable salt thereof, a pharmaceutically acceptable solvate of any of the foregoing, or a pharmaceutically acceptable N-oxide of any of the foregoing, wherein:

$R^1$ is selected from hydrogen, acyl, substituted acyl, acyloxyalkylcarbonyl, substituted acyloxyalkylcarbonyl, oxycarbonyl, substituted oxycarbonyl, and

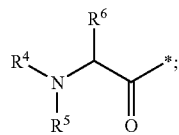

$R^2$ is selected from hydrogen, acyl, substituted acyl, acyloxyalkylcarbonyl, substituted acyloxyalkylcarbonyl, oxycarbonyl, substituted oxycarbonyl, and

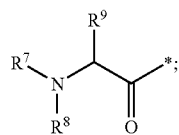

$R^3$ is selected from —N=C($R^{10}$)($R^{11}$) and —NHR$^{12}$;
$R^4$ and $R^7$ are independently selected from hydrogen, alkyl, substituted alkyl, acyl, substituted acyl, acyloxyalkylcarbonyl, substituted acyloxyalkylcarbonyl, arylalkyl, substituted arylalkyl, oxycarbonyl, and substituted oxycarbonyl;
$R^5$ and $R^8$ are independently selected from hydrogen, alkyl, substituted alkyl, arylalkyl, substituted arylalkyl, cycloalkyl, and substituted cycloalkyl;
$R^8$ and $R^9$ are independently selected from hydrogen, alkyl, substituted alkyl, alkoxy, substituted alkoxy, acyl, substituted acyl, alkoxycarbonyl, substituted alkoxycarbonyl, aryl, substituted aryl, arylalkyl, substituted arylalkyl, carbamoyl, substituted carbamoyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, and substituted heteroarylalkyl;
or $R^5$ and $R^6$ together with the nitrogen atom to which they are bonded form a cycloheteroalkyl or substituted cycloheteroalkyl ring;

or $R^8$ and $R^9$ together with the nitrogen atom to which they are bonded form a cycloheteroalkyl or substituted cycloheteroalkyl ring;
$R^{10}$ and $R^{11}$ are independently selected from hydrogen, acyl, substituted acyl, alkyl, substituted alkyl, alkoxy, substituted alkoxy, alkylamino, substituted alkylamino, amido, substituted amido, aryl, substituted aryl, arylalkyl, substituted arylalkyl, cycloalkyl, substituted cycloalkyl, cycloheteroalkyl, substituted cycloheteroalkyl, dialkylamino, substituted dialkylamino, heteroalkyl, substituted heteroalkyl, heteroaryl, substituted heteroaryl, heteroarylalkyl, and substituted heteroarylalkyl;
$R^{12}$ is selected from acyloxyalkylcarbonyl, substituted acyloxyalkylcarbonyl, oxycarbonyl, substituted oxycarbonyl, and a moiety of structural Formula (II):

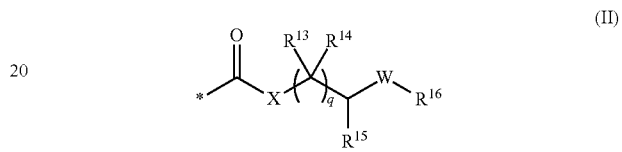

(II)

wherein X is selected from O and $CH_2$;
q is selected from 1 and 2;
each $R^{13}$ and $R^{14}$ are independently selected from hydrogen, $C_{1-4}$ alkyl, phenyl, and substituted phenyl, or $R^{13}$ and $R^{14}$ together with the carbon atom to which they are both bonded form a $C_{3-7}$ cycloalkyl ring;
$R^{15}$ is selected from hydrogen, $C_{1-4}$ alkyl, and —$CO_2R^{17}$;
W is selected from O and NR$^{18}$;
$R^{17}$ is selected from hydrogen, $C_{1-4}$ alkyl, phenyl, and substituted phenyl;
$R^{18}$ is selected from hydrogen and $C_{1-4}$ alkyl;
$R^{16}$ is selected from $C_{1-4}$ alkyl, —C(O)R$^{19}$, —C(O)OR$^{20}$,

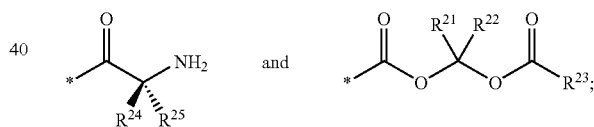

wherein $R^{19}$ is selected from hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, and substituted heteroarylalkyl;
$R^{20}$ is selected from $C_{1-6}$ alkyl, $C_{3-7}$ cycloalkyl, aryl, substituted aryl, arylalkyl, substituted arylalkyl, heteroaryl, and substituted heteroaryl;
$R^{21}$ and $R^{22}$ are independently selected from hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, cycloalkoxycarbonyl, substituted cycloalkoxycarbonyl, heteroaryl, substituted heteroaryl, heteroarylalkyl, and substituted heteroarylalkyl or $R^{21}$ and $R^{22}$ together with the carbon atom to which they are bonded form a cycloalkyl, substituted cycloalkyl, cycloheteroalkyl, or substituted cycloheteroalkyl ring;
$R^{23}$ is selected from acyl, substituted acyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, and substituted heteroarylalkyl;

$R^{24}$ is selected from hydrogen, alkyl, substituted alkyl, alkoxy, substituted alkoxy, acyl, substituted acyl, alkoxycarbonyl, substituted alkoxycarbonyl, aryl, substituted aryl, arylalkyl, substituted arylalkyl, carbamoyl, substituted carbamoyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, and substituted heteroarylalkyl; and $R^{25}$ is selected from hydrogen, and $C_{1-4}$ alkyl; or $R^{24}$ and $R^{25}$ together with the carbon to which they are bonded form a cycloalkyl or cycloheteroalkyl ring;

with the provisos that:

$R^3$ is not phenylcarbonylamino;

when $R^3$ is $-N=C(R^{10})(R^{11})$, and each of $R^1$, $R^2$, and $R^{11}$ is hydrogen; then $R^{12}$ is not dimethylamino; or when $R^3$ is $-NHR^{12}$ and $R^{12}$ is a moiety of structural Formula (II), X is $CH_2$, and W is O; then $R^{16}$ is not $C_{1-4}$ alkyl.

In a second aspect, pharmaceutical compositions are provided which generally comprise one or more compounds of Formula (I), pharmaceutically acceptable salts thereof, pharmaceutically acceptable solvates of any of the foregoing, or pharmaceutically acceptable N-oxides of any of the foregoing, and a pharmaceutically acceptable vehicle such as a diluent, carrier, excipient, or adjuvant. The choice of diluent, carrier, excipient and adjuvant will depend upon, among other factors, the desired mode of administration.

In a third aspect, methods for treating various viral diseases are provided, including infection with hepatitis C. The methods generally involve administering to a patient in need of such treatment a therapeutically effective amount of a compound Formula (I) and/or a pharmaceutical composition thereof.

DETAILED DESCRIPTION

Definitions

Figure 1:
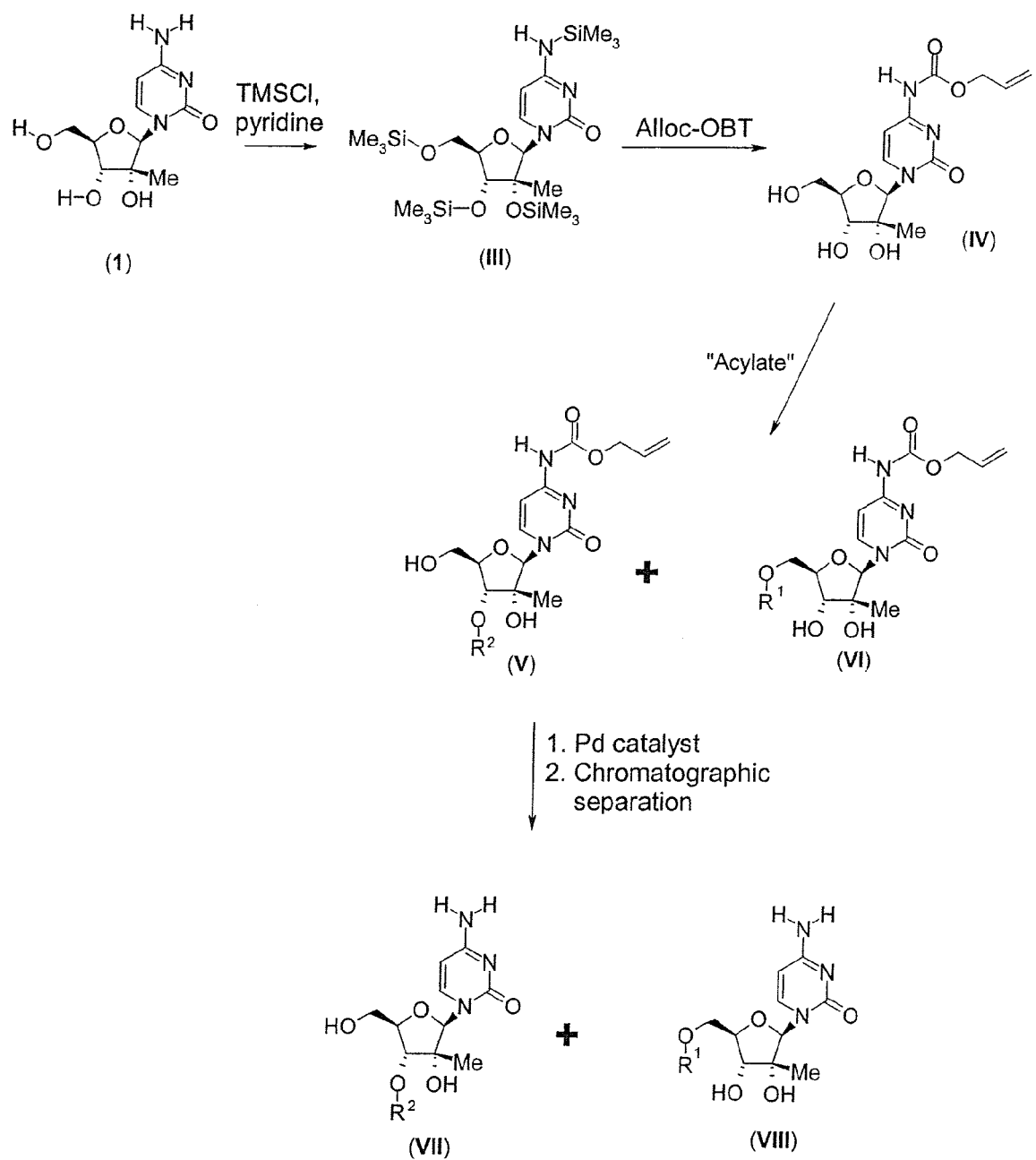
FIG. 1 illustrates a general synthetic route to monosubstituted (3'- or 5'-substituted) 2'-C-methyl-ribofuranosyl cytidine analogs.

A dash ("-") that is not between two letters or symbols is used to indicate a point of attachment for a moiety or substituent. For example, $-CONH_2$ is attached through the carbon atom.

"Aforementioned embodiments of compounds of Formula (I)" refers to embodiments of compounds of Formula (I) within the same numbered paragraph.

"Alkyl" by itself or as part of another substituent refers to a saturated or unsaturated, branched or straight-chain, monovalent hydrocarbon radical derived by the removal of one hydrogen atom from a single carbon atom of a parent alkane, alkene, or alkyne. Examples of alkyl groups include, but are not limited to, methyl; ethyls such as ethanyl, ethenyl, ethynyl; propyls such as propan-1-yl, propan-2-yl, prop-1-en-1-yl, prop-1-en-2-yl, prop-2-en-1-yl (allyl), prop-1-yn-1-yl, prop-2-yn-1-yl, etc.; butyls such as butan-1-yl, butan-2-yl, 2-methyl-propan-1-yl, 2-methyl-propan-2-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. In certain embodiments, an alkyl group comprises from 1 to 20 carbon atoms, in certain embodiments, from 1 to 10 carbon atoms, in certain embodiments from 1 to 6 carbon atoms, in certain embodiments from 1 to 4 carbon atoms, and in certain embodiments from 1 to 3 carbon atoms. "$C_{1-6}$ alkyl" refers to an alkyl group containing from 1 to 6 carbon atoms.

"Alkanyl" by itself or as part of another substituent refers to a saturated branched or straight-chain alkyl radical derived by the removal of one hydrogen atom from a single carbon atom of a parent alkane. Examples of alkanyl groups include, but are not limited to, methanyl; ethanyl; propanyls such as propan-1-yl, propan-2-yl (isopropyl), etc.; butanyls such as butan-1-yl, butan-2-yl (sec-butyl), 2-methyl-propan-1-yl (isobutyl), 2-methyl-propan-2-yl (tert-butyl), etc.; and the like.

"Alkenyl" by itself or as part of another substituent refers to an unsaturated branched or straight-chain alkyl radical having at least one carbon-carbon double bond derived by the removal of one hydrogen atom from a single carbon atom of a parent alkene. The group may be in either the cis or trans conformation about the double bond(s). Examples of alkenyl groups include, but are not limited to, ethenyl; propenyls such as prop-1-en-1-yl, prop-1-en-2-yl, prop-2-en-1-yl (allyl), and prop-2-en-2-yl, ; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, etc.; and the like.

"Alkynyl" by itself or as part of another substituent refers to an unsaturated branched or straight-chain alkyl radical having at least one carbon-carbon triple bond derived by the removal of one hydrogen atom from a single carbon atom of a parent alkyne. Examples of alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Acyl" by itself or as part of another substituent refers to a radical $-C(O)R^{30}$, where $R^{30}$ is selected from hydrogen, alkyl, cycloalkyl, cycloheteroalkyl, aryl, arylalkyl, heteroalkyl, heteroaryl, and heteroarylalkyl, and the corresponding substituted groups as defined herein. Examples of acyl groups include, but are not limited to formyl, acetyl, cyclohexylcarbonyl, cyclohexylmethylcarbonyl, benzoyl, benzylcarbonyl, and the like.

"Acyloxyalkylcarbonyl" by itself or as part of another substituent refers to a radical $-C(O)OC(R^{21})(R^{22})OC(O)R^{23}$ where $R^{21}$ and $R^{22}$ are independently selected from hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, cycloalkoxycarbonyl, substituted cycloalkoxycarbonyl, heteroaryl, substituted heteroaryl, heteroarylalkyl, and substituted heteroarylalkyl; or $R^{21}$ and $R^{22}$ together with the carbon atom to which they are bonded form a cycloalkyl, substituted cycloalkyl, cycloheteroalkyl, or substituted cycloheteroalkyl ring; and $R^{23}$ is selected from acyl, substituted acyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, and substituted heteroarylalkyl.

"Alkylamino" by itself or as part of another substituent refers to a radical —$NHR^{35}$ where $R^{35}$ is selected from alkyl, substituted, cycloalkyl, and substituted cycloalkyl as defined herein. Examples of alkylamino groups include, but are not limited to, methylamino, ethylamino, 1-methylethylamino, cyclohexyl amino, and the like.

"Alkoxy" by itself or as part of another substituent refers to a radical —$OR^{36}$ where $R^{36}$ is selected from alkyl, substituted alkyl, cycloalkyl, and substituted cycloalkyl, as defined herein. Examples of alkoxy groups include, but are not limited to, methoxy, ethoxy, propoxy, butoxy, cyclohexyloxy, and the like.

"Amido" by itself or as part of another substituent refers to a radical —$NR^{37}C(O)R^{38}$, where $R^{37}$ and $R^{38}$ are independently selected from hydrogen, alkyl, cycloalkyl, cycloheteroalkyl, aryl, arylalkyl, heteroalkyl, heteroaryl, and heteroarylalkyl, as defined herein. Examples of amido groups include, but are not limited to, formylamino, acetylamino (i.e., acetamido), cyclohexylcarbonylamino, cyclohexylmethylcarbonylamino, benzoylamino (i.e., benzamido), benzylcarbonylamino, and the like.

"Aryl" by itself or as part of another substituent refers to a monovalent aromatic hydrocarbon radical derived by the removal of one hydrogen atom from a single carbon atom of a parent aromatic ring system. Aryl encompasses carbocyclic aromatic rings, for example, benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene. Aryl encompasses multiple ring systems having at least one carbocyclic aromatic ring fused to at least one carbocylic aromatic ring, cycloalkyl ring, or heterocycloalkyl ring. For example, aryl includes 5- and 6-membered carbocyclic aromatic rings fused to a 5- to 7-membered heterocycloalkyl ring containing one or more heteroatoms chosen from N, O, and S. For such fused, bicyclic ring systems wherein only one of the rings is a carbocyclic aromatic ring, the point of attachment may be at the carbocyclic aromatic ring or the heterocycloalkyl ring. Examples of aryl groups include, but are not limited to, groups derived from aceanthrylene, acenaphthylene, acephenanthryiene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In certain embodiments, an aryl group comprises from 6 to 20 carbon atoms ($C_{6-20}$), in certain embodiments, from 6 to 12 carbon atoms ($C_{6-12}$), and in certain embodiments from 6 to 8 carbon atoms (C6-8). Aryl, however, does not encompass or overlap in any way with heteroaryl, separately defined herein.

"Arylalkyl" by itself or as part of another substituent refers to an acyclic alkyl radical in which one of the hydrogen atoms bonded to a carbon atom, typically a terminal or $sp^3$ carbon atom, is replaced with an aryl group. Examples of arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl, or arylalkynyl is used. In certain embodiments, an arylalkyl group is $C_{6-30}$ arylalkyl, e.g., the alkanyl, alkenyl or alkynyl moiety of the arylalkyl group is $C_{1-10}$ and the aryl moiety is $C_{6-20}$, in certain embodiments, an arylalkyl group is $C_{6-20}$ arylalkyl, e.g., the alkanyl, alkenyl or alkynyl moiety of the arylalkyl group is $C_{1-8}$ and the aryl moiety is $C_{6-12}$.

"Carbamoyl" by itself or as part of another substituent refers to the radical —$C(O)N(R^{39})R^{40}$ where $R^{39}$ and $R^{40}$ are independently selected from hydrogen, alkyl, substituted alkyl, aryl, substituted aryl, arylalkyl, substituted arylalkyl, heteroarylalkyl, substituted heteroarylalkyl, heteroaryl, and substituted heteroaryl, as defined herein.

"Compounds," such as for example, "compounds of Formula (I), refers to compounds encompassed by the generic formulae disclosed herein and includes any specific compounds within those formulae whose structure is disclosed herein. Compounds may be identified either by their chemical structure and/or chemical name. When the chemical structure and chemical name conflict, the chemical structure is determinative of the identity of the compound. The compounds described herein may contain one or more chiral centers and/or double bonds and therefore, may exist as stereoisomers, such as double-bond isomers (i.e., geometric isomers), enantiomers, or diastereomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure, or diastereomerically pure) and enantiomeric and stereoisomeric mixtures. Enantiomeric and stereoisomeric mixtures may be resolved into their component enantiomers or stereoisomers using separation techniques or chiral synthesis techniques well known to the skilled artisan.

Compounds include, but are not limited to, optical isomers, racemates thereof, and other mixtures thereof. In such embodiments, the single enantiomers or diastereomers, i.e., optically active forms, can be obtained by asymmetric synthesis or by resolution of the racemates. Resolution of the racemates may be accomplished, for example, by conventional methods such as crystallization in the presence of a resolving agent, or chromatography, using, for example a chiral high-pressure liquid chromatography (HPLC) column. In addition, compounds include Z- and E-forms (or cis- and trans-forms) of compounds with double bonds.

The compounds may also exist in several tautomeric forms including the enol form, the keto form and mixtures thereof. Accordingly, the chemical structures depicted herein encompass all possible tautomeric forms of the illustrated compounds. The compounds also include isotopically labeled compounds where one or more atoms have an atomic mass different from the atomic mass conventionally found in nature. Examples of isotopes that may be incorporated into the compounds include, but are not limited to, $^2H$, $^3H$, $^{13}C$, $^{14}C$, $^{15}N$, $^{18}O$, $^{17}O$, $^{31}P$ and $^{32}P$. Compounds may exist in unsolvated forms as well as solvated forms, including hydrated forms and as N-oxides. In general, the hydrated, solvated and N-oxide forms are within the scope of the present disclosure. Certain compounds may exist in multiple crystalline or amorphous forms. Compounds include pharmaceutically acceptable salts thereof, or pharmaceutically acceptable solvates of the free acid form of any of the foregoing, as well as crystalline forms of any of the foregoing.

In general, all physical forms are equivalent for the uses contemplated herein and are intended to be within the scope of the present disclosure. Further, when partial structures of the compounds are illustrated, an asterisk (*) indicates the point of attachment of the partial structure to the rest of the molecule.

"Cycloalkyl" by itself or as part of another substituent refers to a saturated or unsaturated cyclic alkyl radical. Where a specific level of saturation is intended, the nomenclature "cycloalkanyl" or "cycloalkenyl" is used. Examples of cycloalkyl groups include, but are not limited to, groups derived from cyclopropane, cyclobutane, cyclopentane, cyclohexane, and the like. In certain embodiments, a cycloalkyl group is $C_{3-15}$ cycloalkyl, in certain embodiments, $C_{5-12}$ cycloalkyl, and in certain embodiments, $C_{3-7}$ cycloalkyl.

"Cycloheteroalkyl" by itself or as part of another substituent refers to a saturated or unsaturated cyclic alkyl radical in which one or more carbon atoms (and any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Examples of cycloheteroalkyl groups include, but are not limited to, groups derived from epoxides, azirines, thiiranes, imidazolidine, morpholine, piperazine, piperidine, pyrazolidine, pyrrolidine, quinuclidine, and the like.

"Dialkylamino" by itself or as part of another substituent refers a radical —$NR^{41}R^{42}$ where $R^{41}$ and $R^{42}$ are independently selected from alkyl, substituted alkyl, cycloalkyl, and substituted cycloalkyl, as defined herein. Examples of dialkylamino groups include, but are not limited to, dimethylamino, methylethylamino, di-(1-methylethyl)amino, (cyclohexyl)(methyl)amino, (cyclohexyl)(ethyl)amino, (cyclohexyl)(propyl)amino, and the like.

"Heteroalkyl, heteroalkanyl, heteroalkenyl and heteroalkynyl" by themselves or as part of another substituent refer to alkyl, alkanyl, alkenyl, or alkynyl groups, respectively, in which one or more of the carbon atoms (and any associated hydrogen atoms) are independently replaced with the same or different heteroatomic groups. Examples of heteroatomic groups include, but are not limited to, —O—, —S—, —O—O—, —S—S—, —O—S—, —$NR^{43}R^{44}$—, =N—N=, —N=N—, —N=N—$NR^{45}R^{46}$, —$PR^{46}$—, —$P(O)_2$—, —$POR^{48}$—, —O—$P(O)_2$—, —SO—, —$SO_2$—, —$SnR^{49}R^{50}$— and the like, where $R^{43}$, $R^{44}$, $R^{45}$, $R^{46}$, $R^{47}$, $R^{48}$, $R^{49}$, and $R^{50}$ are independently selected from hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, and substituted heteroarylalkyl. In certain embodiments, $R^{37}$, $R^{38}$, $R^{39}$, $R^{40}$, $R^{41}$, $R^{42}$, $R^{43}$, and $R^{44}$ are independently selected from hydrogen, $C_{1-6}$ alkyl, substituted $C_{1-6}$ alkyl, $C_{6-12}$ aryl, substituted $C_{6-12}$ aryl, $C_{7-18}$ arylalkyl, substituted $C_{7-18}$ arylalkyl, $C_{3-7}$ cycloalkyl, substituted $C_{3-7}$ cycloalkyl, $C_{3-7}$ cycloheteroalkyl, substituted $C_{3-7}$ cycloheteroalkyl, $C_{1-6}$ heteroalkyl, substituted $C_{1-6}$ heteroalkyl, $C_{6-12}$ heteroaryl, substituted $C_{6-12}$ heteroaryl, $C_{7-18}$ heteroarylalkyl, and substituted $C_{7-18}$ heteroarylalkyl. In certain embodiments, $R^{37}$, $R^{38}$, $R^{39}$, $R^{40}$, $R^{41}$, $R^{42}$, $R^{43}$, and $R^{44}$ are independently selected from hydrogen and $C_{1-4}$ alkyl.

"Heteroaryl" by itself or as part of another substituent refers to a monovalent heteroaromatic radical derived by the removal of one hydrogen atom from a single atom of a parent heteroaromatic ring system. Heteroaryl encompasses multiple ring systems having at least one heteroaromatic ring fused to at least one other ring, which can be aromatic or non-aromatic. Heteroaryl encompasses 5- to 7-membered aromatic, monocyclic rings containing one or more, for example, from 1 to 4, or in certain embodiments, from 1 to 3, heteroatoms chosen from N, O, and S, with the remaining ring atoms being carbon; and bicyclic heterocycloalkyl rings containing one or more, for example, from 1 to 4, or in certain embodiments, from 1 to 3, heteroatoms chosen from N, O, and S, with the remaining ring atoms being carbon and wherein at least one heteroatom is present in an aromatic ring. For example, heteroaryl includes a 5- to 7-membered heteroaromatic ring fused to a 5- to 7-membered cycloalkyl ring. For such fused, bicyclic heteroaryl ring systems wherein only one of the rings contains one or more heteroatoms, the point of attachment may be at the heteroaromatic ring or the cycloalkyl ring. In certain embodiments, when the total number of N, S, and O atoms in the heteroaryl group exceeds one, the heteroatoms are not adjacent to one another. In certain embodiments, the total number of N, S, and O atoms in the heteroaryl group is not more than two. In certain embodiments, the total number of N, S, and O atoms in the aromatic heterocycle is not more than one. Heteroaryl does not encompass or overlap with aryl as defined herein. Examples of heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In certain embodiments, a heteroaryl group is from 5-20 membered heteroaryl, in certain embodiments, from 5-10 membered heteroaryl, and in certain embodiments, from 6- to 8-heteroaryl. In certain embodiments, heteroaryl groups are those derived from thiophene, pyrrole, benzothiophene, benzofuran, indole, pyridine, quinoline, imidazole, oxazole, and pyrazine.

"Heteroarylalkyl" by itself or as part of another substituent refers to an acyclic alkyl radical in which one of the hydrogen atoms bonded to a carbon atom is replaced with a heteroaryl group. Typically a terminal or $Sp^3$ carbon atom is the atom replaced with the heteroaryl group. Where specific alkyl moieties are intended, the nomenclature heteroarylalkanyl, heteroarylalkenyl, and heterorylalkynyl is used. In certain embodiments, a heteroarylalkyl group is a 6- to 30-membered heteroarylalkyl ($C_{1-30}$), e.g., the alkanyl, alkenyl, or alkynyl moiety of the heteroarylalkyl is 1- to 10-membered ($C_{1-10}$) and the heteroaryl moiety is a 5- to 20-membered heteroaryl ($C_{5-20}$), and in certain embodiments, 6- to 20-membered ($C_{6-20}$) heteroarylalkyl, e.g., the alkanyl, alkenyl, or alkynyl moiety of the heteroarylalkyl is 1- to 8-membered ($C_{1-8}$) and the heteroaryl moiety is a 5- to 12-membered ($C_{5-12}$) heteroaryl.

"Oxycarbonyl" by itself or as part of another substituent refers to a radical —C(O)—$OR^{51}$ where $R^{51}$ is selected from alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, and substituted heteroarylalkyl, as defined herein. Examples of oxycarbonyl groups include, but are not limited to, methoxycarbonyl, piperdineoxycarbonyl, phenyloxycarbonyl, benzyloxycarbonyl, and the like.

"Parent aromatic ring system" refers to an unsaturated cyclic or polycyclic ring system having a conjugated π (pi) electron system. Included within the definition of "parent aromatic ring system" are fused ring systems in which one or more of the rings are aromatic and one or more of the rings are saturated or unsaturated, such as, for example, fluorene, indane, indene, phenalene, etc. Examples of parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like.

"Parent heteroaromatic ring system" refers to a parent aromatic ring system in which one or more carbon atoms (and any associated hydrogen atoms) are independently replaced with the same or different heteroatom. Examples of heteroatoms to replace the carbon atoms include, but are not limited to, N, P, O, S, Si, etc. Included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Examples of parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Pharmaceutically acceptable salt" refers to a salt of a compound, which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; and (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine, and the like. In certain embodiments, a pharmaceutically acceptable salt is the hydrochloride salt.

"Pharmaceutically acceptable" refers to approved or approvable by a regulatory agency of the Federal or a state government or listed in the U.S. Pharmacopoeia or other generally recognized pharmacopoeia for use in animals, and more particularly in humans.

"Pharmaceutically acceptable vehicle" refers to a pharmaceutically acceptable diluent, a pharmaceutically acceptable adjuvant, a pharmaceutically acceptable excipient, a pharmaceutically acceptable carrier, or a combination of any of the foregoing with which a compound provided by the present disclosure may be administered to a patient and which does not destroy the pharmacological activity thereof and which is non-toxic when administered in doses sufficient to provide a therapeutically effective amount of the compound.

"Patient" refers to a mammal, for example, a human.

"Prodrug" refers to a derivative of a drug molecule that requires a transformation within the body to release the active drug. Prodrugs are frequently, although not necessarily, pharmacologically inactive until converted to the parent drug. Prodrugs can be obtained by bonding a promoiety (defined herein) typically via a functional group, to a drug. For example, referring to compounds of Formula (I) the drug is 2'-C-methyl-ribofuranosyl cytidine prodrugs and the promoieties are the $R^1$, $R^2$, and/or $R^3$ groups.

"Promoiety" refers to a group bonded to a drug, typically to a functional group of the drug, via bond(s) that are cleavable under specified conditions of use. The bond(s) between the drug and promoiety may be cleaved by enzymatic or non-enzymatic means. Under the conditions of use, for example following administration to a patient, the bond(s) between the drug and promoiety may be cleaved to release the parent drug. The cleavage of the promoiety may proceed spontaneously, such as via a hydrolysis reaction, or it may be catalyzed or induced by another agent, such as by an enzyme, by light, by acid, or by a change of or exposure to a physical or environmental parameter, such as a change of temperature, pH, etc. The agent may be endogenous to the conditions of use, such as an enzyme present in the systemic circulation of a patient to which the prodrug is administered or the acidic conditions of the stomach, or the agent may be supplied exogenously. For example, for a prodrug of Formula (I), the promoieties are the $R^1$, $R^2$, and/or $R^3$ groups.

"Protecting group" refers to a grouping of atoms that when bonded to a reactive functional group in a molecule masks, reduces or prevents reactivity of the functional group. Examples of protecting groups can be found in Green et al., "Protective Groups in Organic Chemistry," (Wiley, $2^{nd}$ ed. 1991) and Harrison et al., "Compendium of Synthetic Organic Methods," Vols. 1-8 (John Wiley and Sons, 1971-1996). Representative amino protecting groups include, but are not limited to, formyl, acetyl, trifluoroacetyl, benzyl, benzyloxycarbonyl (CBZ), tert-butoxycarbonyl (Boc), trimethylsilyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC) and the like. Examples of hydroxy protecting groups include, but are not limited to, those where the hydroxy group is either acylated or alkylated such as benzyl and trityl ethers as well as alkyl ethers, tetrahydropyranyl ethers, trialkylsilyl ethers, and allyl ethers.

"Substituted" refers to a group in which one or more hydrogen atoms are independently replaced with the same or different substituent(s). Examples of substituents include, but are not limited to, -M, $-R^{60}$, $-O^-$, $=O$, $-OR^{60}$, $-SR^{60}$, $-S^-$, $=S$, $-NR^{60}R^{61}$, $=NR^6$, $-CF_3$, $-CN$, $-OCN$, —SCN, —NO, —NO$_2$, =N$_2$, —N$_3$, —S(O)$_2$O$^-$, —S(O)$_2$OH, —S(O)$_2$R$^{60}$, —OS(O$_2$)O$^-$, —OS(O)$_2$R$^{60}$, —P(O)(O$^-$)$_2$, —P(O)(OR$^{60}$)(O$^-$), —OP(O)(OR$^{60}$)(R$^{61}$), —C(O)R$^{60}$, —C(S)R$^{60}$, —C(O)OR$^{60}$, —C(O)NR$^{60}$R$^{61}$, —C(O)O$^-$, —C(S)OR$^{60}$, —NR$^{62}$C(O)NR$^{60}$R$^{61}$, —NR$^{62}$C(S)NR$^{60}$R$^{61}$, —NR$^{62}$C(NR$^{63}$)NR$^{60}$R$^{61}$, and —C(NR$^{62}$)NR$^{60}$R$^{61}$ where M is independently a halogen; R$^{60}$, R$^{61}$, R$^{62}$, and R$^{63}$ are independently selected from hydrogen, alkyl, substituted alkyl, alkoxy, substituted alkoxy, cycloalkyl, substituted cycloalkyl, cycloheteroalkyl, substituted cycloheteroalkyl, aryl, substituted aryl, heteroaryl, and substituted heteroaryl; or R$^{60}$ and R$^{61}$ together with the nitrogen atom to which they are bonded form a cycloheteroalkyl or substituted cycloheteroalkyl ring; and R$^{64}$ and R$^{65}$ are independently selected from hydrogen, alkyl, substituted alkyl, aryl, cycloalkyl, substituted cycloalkyl, cycloheteroalkyl, substituted cycloheteroalkyl, aryl, substituted aryl, heteroaryl, and substituted heteroaryl; or R$^{64}$ and R$^{65}$ together with the nitrogen atom to which they are bonded form a cycloheteroalkyl or substituted cycloheteroalkyl ring. In certain embodiments, substituents are selected from -M, —R$^{60}$, =O, —OR$^{60}$, —SR$^{60}$, —S$^-$, =S, —NR$^{60}$R$^{61}$, =NR$^{60}$, —CF$_3$, —CN, —OCN, —SCN, —NO, —NO$_2$, =N$_2$, —N$_3$, —S(O)$_2$R$^{60}$, —OS($_2$)O$^-$, —OS(O)$_2$R$^{60}$, —P(O)(O$^-$)$_2$, —P(O)(OR$^{60}$)(O$^-$), —OP(O)(OR$^{60}$)(OR$^{61}$), —C(O)R$^{60}$, —C(S)R$^{60}$, —C(O)OR$^{60}$, —C(O)NR$^{60}$R$^{61}$, —C(O)O$^-$, and —NR$^{62}$C(O)NR$^{60}$R$^{61}$; in certain embodiments, -M, —R$^{60}$, =O, —OR$^{60}$, —SR$^{60}$, —NR$^{60}$R$^{61}$, —CF$_3$, —CN, —NO$_2$, —S(O)$_2$R$^{60}$, —P(O)(OR$^{60}$)(O$^-$), —OP(O)(OR$^{60}$)(OR$^{61}$), —C(O)R$^{60}$, —C(O)OR$^{60}$, —C(O)NR$^{60}$R$^{61}$, and —C(O)O$^-$; and in certain embodiments, -M, —R$^{60}$, =O, —OR$^{60}$, —SR$^{60}$, —NR$^{60}$R$^{61}$, —CF$_3$, —CN, —NO$_2$, —S(O)$_2$R$^{60}$, —OP(O)(OR$^{60}$)(OR$^{61}$), —C(O)R$^{60}$, —C(O)OR$^{60}$, and —C(O)O$^-$, where R$^{60}$, R$^{61}$, and R$^{62}$ are as defined herein. In certain embodiments, R$^{60}$, R$^{61}$, R$^{62}$, and R$^{63}$ are independently selected from hydrogen, alkyl, alkoxy, cycloalkyl, cycloheteroalkyl, aryl, and heteroaryl, or R$^{60}$ and R$^{61}$ together with the nitrogen atom to which they are bonded form a ring chosen from a cycloheteroalkyl ring. In certain embodiments, R$^{60}$, R$^{61}$, R$^{62}$, and R$^{63}$ are independently selected from hydrogen, C$_{1-6}$ alkyl, C$_{1-6}$ alkoxy, C$_{3-12}$ cycloalkyl, C$_{3-12}$ cycloheteroalkyl, C$_{6-12}$ a and C$_{6-12}$ heteroaryl. In certain embodiments, each substituted group is independently selected from halogen, —OH, —CN, —CF$_3$, =O, —NO$_2$, C$_{1-3}$ alkoxy, C$_{1-3}$ alkyl, —COOR$^{64}$ wherein R$^{64}$ is selected from hydrogen and C$_{1-3}$ alkyl, and —NR$^{65}$$_2$ wherein each R$^{65}$ is independently selected from hydrogen and C$_{1-3}$ alkyl.

"Treating" or "treatment" of any disease or disorder refers to arresting or ameliorating a disease, disorder, or at least one of the clinical symptoms of a disease or disorder, reducing the risk of acquiring a disease, disorder, or at least one of the clinical symptoms of a disease or disorder, reducing the development of a disease, disorder or at least one of the clinical symptoms of the disease or disorder, or reducing the risk of developing a disease or disorder or at least one of the clinical symptoms of a disease or disorder. "Treating" or "treatment" also refers to inhibiting the disease or disorder, either physically, (e.g., stabilization of a discernible symptom), physiologically, (e.g., stabilization of a physical parameter), or both, and to inhibiting at least one physical parameter that may or may not be discernible to the patient. In certain embodiments, "treating" or "treatment" refers to delaying the onset of the disease or disorder or at least one or more symptoms thereof in a patient which may be exposed to or predisposed to a disease or disorder even though that patient does not yet experience or display symptoms of the disease or disorder.

"Therapeutically effective amount" refers to the amount of a compound that, when administered to a subject for treating a disease or disorder, or at least one of the clinical symptoms of a disease or disorder, is sufficient to affect such treatment of the disease, disorder, or symptom. The "therapeutically effective amount" may vary depending, for example, on the compound, the disease, disorder, and/or symptoms of the disease or disorder, severity of the disease, disorder, and/or symptoms of the disease or disorder, the age, weight, and/or health of the patient to be treated, and the judgment of the prescribing physician. An appropriate amount in any given instance may be ascertained by those skilled in the art or capable of determination by routine experimentation.

Reference is now made in detail to certain embodiments of compounds, compositions, and methods. The disclosed embodiments are not intended to be limiting of the claims. To the contrary, the claims are intended to cover all alternatives, modifications, and equivalents.

Compounds

In certain embodiments of compounds of Formula (I):

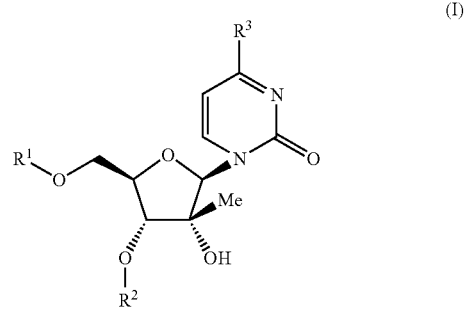

pharmaceutically acceptable salts thereof, pharmaceutically acceptable solvates of any of the foregoing, or pharmaceutically acceptable N-oxides of any of the foregoing, wherein:

R$^1$ is selected from hydrogen, acyl, substituted acyl, acyloxyalkylcarbonyl, substituted acyloxyalkylcarbonyl, oxycarbonyl, substituted oxycarbonyl, and

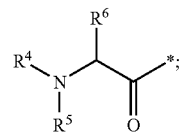

R$^2$ is selected from hydrogen, acyl, substituted acyl, acyloxyalkylcarbonyl, substituted acyloxyalkylcarbonyl, oxycarbonyl, substituted oxycarbonyl, and

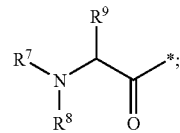

R$^3$ is selected from —N=C(R$^{10}$)(R$^{11}$) and —NHR$^{12}$;

R$^4$ and R$^7$ are independently selected from hydrogen, alkyl, substituted alkyl, acyl, substituted acyl, acyloxyalkylcarbonyl, substituted acyloxyalkylcarbonyl, arylalkyl, substituted arylalkyl, oxycarbonyl, and substituted oxycarbonyl;

$R^5$ and $R^8$ are independently selected from hydrogen, alkyl, substituted alkyl, arylalkyl, substituted arylalkyl, cycloalkyl, and substituted cycloalkyl;

$R^6$ and $R^9$ are independently selected from hydrogen, alkyl, substituted alkyl, alkoxy, substituted alkoxy, acyl, substituted acyl, alkoxycarbonyl, substituted alkoxycarbonyl, aryl, substituted aryl, arylalkyl, substituted arylalkyl, carbamoyl, substituted carbamoyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, and substituted heteroarylalkyl;

or, $R^5$ and $R^6$ together with the nitrogen atom to which they are bonded form a cycloheteroalkyl or substituted cycloheteroalkyl ring;

or, $R^8$ and $R^9$ together with the nitrogen atom to which they are bonded form a cycloheteroalkyl or substituted cycloheteroalkyl ring;

$R^{10}$ and $R^{11}$ are independently selected from hydrogen, acyl, substituted acyl, alkyl, substituted alkyl, alkoxy, substituted alkoxy, alkylamino, substituted alkylamino, amido, substituted amido, aryl, substituted aryl, arylalkyl, substituted arylalkyl, cycloalkyl, substituted cycloalkyl, cycloheteroalkyl, substituted cycloheteroalkyl, dialkylamino, substituted dialkylamino, heteroalkyl, substituted heteroalkyl, heteroaryl, substituted heteroaryl, heteroarylalkyl, and substituted heteroarylalkyl;

$R^{12}$ is selected from acyloxyalkylcarbonyl, substituted acyloxyalkylcarbonyl, oxycarbonyl, substituted oxycarbonyl, and a moiety of structural Formula (II):

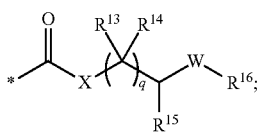

(II)

wherein X is selected from O and $CH_2$;
q is selected from 1 and 2;
each $R^{13}$ and $R^{14}$ is independently selected from hydrogen, $C_{1-4}$ alkyl, phenyl, and substituted phenyl; or $R^{13}$ and $R^{14}$ together with the carbon atom to which they are both bonded form a $C_{3-7}$ cycloalkyl ring;
$R^{15}$ is selected from hydrogen, $C_{1-4}$ alkyl, and $-CO_2R^{17}$;
W is selected from O and $NR^{18}$;
$R^{17}$ is selected from hydrogen, $C_{1-4}$ alkyl, phenyl, and substituted phenyl;
$R^{18}$ is selected from hydrogen and $C_{1-4}$ alkyl;
$R^{16}$ is selected from $C_{1-4}$ alkyl, $-C(O)R^{19}$, $-C(O)OR^{20}$,

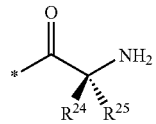 and 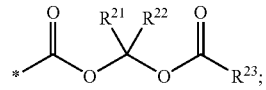;

wherein $R^{19}$ is selected from hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, and substituted heteroarylalkyl;

$R^{20}$ is selected from $C_{1-6}$ alkyl, $C_{3-7}$ cycloalkyl, aryl, substituted aryl, arylalkyl, substituted arylalkyl, heteroaryl, and substituted heteroaryl;

$R^{21}$ and $R^{22}$ are independently selected from hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, cycloalkoxycarbonyl, substituted cycloalkoxycarbonyl, heteroaryl, substituted heteroaryl, heteroarylalkyl, and substituted heteroarylalkyl; or $R^{21}$ and $R^{22}$ together with the carbon atom to which they are bonded form a cycloalkyl, substituted cycloalkyl, cycloheteroalkyl, or substituted cycloheteroalkyl ring;

$R^{23}$ is selected from acyl, substituted acyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, and substituted heteroarylalkyl;

$R^{24}$ is selected from hydrogen, alkyl, substituted alkyl, alkoxy, substituted alkoxy, acyl, substituted acyl, alkoxycarbonyl, substituted alkoxycarbonyl, aryl, substituted aryl, arylalkyl, substituted arylalkyl, carbamoyl, substituted carbamoyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, and substituted heteroarylalkyl; and $R^{25}$ is selected from hydrogen and $C_{1-4}$ alkyl; or $R^{24}$ and $R^{25}$ together with the carbon to which they are bonded form a cycloalkyl or cycloheteroalkyl ring;

with the provisos that:
$R^3$ is not phenylcarbonylamino;
when $R^3$ is $-N=C(R^{10})(R^{11})$, and each of $R^1$, $R^2$ and $R^{11}$ is hydrogen; then $R^{12}$ is not dimethylamino; or
when $R^3$ is $-NHR^{12}$ and $R^{12}$ is a moiety of structural Formula (II), X is $CH_2$, and W is O; then $R^{16}$ is not $C_{1-4}$ alkyl.

In certain embodiments of compounds of Formula (I), $R^1$ is selected from hydrogen, acyl, substituted acyl, acyloxyalkylcarbonyl, substituted acyloxyalkylcarbonyl, oxycarbonyl, and substituted oxycarbonyl. In certain embodiments, $R^1$ is selected from hydrogen, acyl, and substituted acyl. In still another embodiment, $R^1$ is selected from hydrogen, acyloxyalkylcarbonyl, substituted acyloxyalkylcarbonyl, oxycarbonyl, and substituted oxycarbonyl.

In certain embodiments of compounds of Formula (I), $R^2$ is selected from hydrogen, acyl, substituted acyl, acyloxyalkylcarbonyl, substituted acyloxyalkylcarbonyl, oxycarbonyl, and substituted oxycarbonyl. In other embodiments, $R^2$ is selected from hydrogen, acyl, and substituted acyl. In other embodiments, $R^2$ is selected from hydrogen, acyloxyalkylcarbonyl, substituted acyloxyalkylcarbonyl, oxycarbonyl, and substituted oxycarbonyl.

In certain embodiments of compounds of Formula (I), $R^3$ is $-N=C(R^{10})(R^{11})$, and $R^{10}$ and $R^{11}$ are independently selected from hydrogen, alkoxy, substituted alkoxy, alkyl, substituted alkyl, alkylamino, substituted alkylamino, amido, substituted amido, aryl, substituted aryl, arylalkyl, substituted arylalkyl, dialkylamino, substituted dialkylamino, heteroalkyl, substituted heteroalkyl, heteroaryl, substituted heteroaryl, heteroarylalkyl, and substituted heteroarylalkyl. In certain embodiments of compounds of Formula (I), $R^3$ is $-N=C(R^{10})(R^{11})$, $R^{10}$ and $R^{11}$ are independently selected from hydrogen, alkoxy, substituted alkoxy, alkylamino, substituted alkylamino, amido, substituted amido, dialkylamino, and substituted dialkylamino.

In certain embodiments of compounds of Formula (I), $R^3$ is —$NHR^{12}$, and $R^{12}$ is selected from acyloxyalkylcarbonyl, substituted acyloxyalkylcarbonyl, oxycarbonyl, substituted oxycarbonyl, and a moiety of structural Formula (II). In certain embodiments of compounds of Formula (I), $R^3$ is —$NHR^{12}$, and $R^{12}$ is selected from acyloxyalkylcarbonyl and oxycarbonyl. In certain embodiments of compounds of Formula (1), $R^3$ is —$NHR^{12}$, and $R^{12}$ is a moiety of structural Formula (II).

In certain embodiments of compounds of Formula (I), $R^4$ and $R^7$ are independently selected from hydrogen, acyl, substituted acyl, acyloxyalkylcarbonyl, substituted acyloxyalkylcarbonyl, oxycarbonyl, and substituted oxycarbonyl. In other embodiments, $R^4$ and $R^7$ are independently selected from hydrogen, acyl, and substituted acyl. In other embodiments, $R^4$ and $R^7$ are independently selected from hydrogen, acyloxyalkylcarbonyl, and substituted acyloxyalkylcarbonyl. In still other embodiments, each of $R^4$ and $R^7$ is hydrogen.

In certain embodiments of compounds of Formula (I), $R^5$ and $R^8$ are independently selected from hydrogen, alkyl, substituted alkyl, arylalkyl, substituted arylalkyl, cycloalkyl, and substituted cycloalkyl. In other embodiments, $R^5$ and $R^8$ are independently selected from hydrogen and $C_{1-4}$ alkyl. In certain embodiments of compounds of Formula (I), each of $R^5$ and $R^8$ is hydrogen.

In certain embodiments of compounds of Formula (I), $R^6$ and $R^9$ are independently selected from hydrogen, alkanyl, substituted alkanyl, aryl, substituted aryl, arylalkanyl, substituted arylalkanyl, cycloalkanyl, heteroarylalkyl, and substituted heteroarylalkanyl. In other embodiments, $R^6$ and $R^9$ are independently selected from hydrogen, alkanyl, and cycloalkanyl. In certain embodiments, $R^6$ and $R^9$ are independently selected from hydrogen, methyl, isopropyl, isobutyl, sec-butyl, tert-butyl, cyclopentyl, and cyclohexyl. In still other embodiments of compounds of Formula (I), $R^6$ and $R^9$ are independently substituted alkanyl.

In certain embodiments, $R^6$ and $R^9$ are independently selected from —$CH_2OH$, —$CH(OH)CH_3$, —$CH_2CO_2H$, —$CH_2CH_2CO_2H$, —$CH_2CONH_2$, —$CH_2CH_2CONH_2$, —$CH_2CH_2SCH_3$, —$CH_2SH$, —$CH_2(CH_2)_3NH_2$, and —$CH_2CH_2CH_2NHC(NH)NH_2$. In still other embodiments, $R^6$ and $R^9$ are independently selected from aryl, arylalkanyl, substituted arylalkanyl, and heteroarylalkanyl. In certain embodiments of compounds of Formula (I), $R^6$ and $R^9$ are independently selected from phenyl, benzyl, 4-hydroxybenzyl, 4-imidazolylmethyl, and 3-indolylmethyl.

In certain embodiments of compounds of Formula (I), $R^5$ and $R^6$ or $R^8$ and $R^9$ together with the nitrogen atom to which they are bonded form a cycloheteroalkyl or substituted cycloheteroalkyl ring. In certain embodiments, $R^5$ and $R^6$ or $R^8$ and $R^9$ together with the nitrogen atom to which they are bonded form an azetidine, pyrrolidine, or piperidine ring.

In certain embodiments of compounds of Formula (I), $R^1$ is hydrogen; $R^2$ is hydrogen; $R^3$ is —$N=C(R^{10})(R^{11})$, and $R^{10}$ and $R^{11}$ are independently selected from hydrogen, alkoxy, substituted alkoxy, alkyl, substituted alkyl, alkylamino, substituted alkylamino, amido, substituted amido, aryl, substituted aryl, arylalkyl, substituted arylalkyl, dialkylamino, substituted dialkylamino, heteroalkyl, substituted heteroalkyl, heteroaryl, substituted heteroaryl, heteroarylalkyl, and substituted heteroarylalkyl.

In certain embodiments of compounds of Formula (I), $R^1$ is

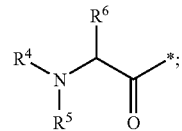

$R^2$ is hydrogen; and
$R^3$ is —$N=C(R^{10})(R^{11})$, and $R^{10}$ and $R^{11}$ are independently selected from hydrogen, alkoxy, substituted alkoxy, alkyl, substituted alkyl, alkylamino, substituted alkylamino, amido, substituted amido, aryl, substituted aryl, arylalkyl, substituted arylalkyl, dialkylamino, substituted dialkylamino, heteroalkyl, substituted heteroalkyl, heteroaryl, substituted heteroaryl, heteroarylalkyl, and substituted heteroarylalkyl.

In certain of the aforementioned embodiments, each of $R^4$ and $R^5$ is hydrogen; and $R^6$ is selected from hydrogen, methyl, isopropyl, isobutyl, sec-butyl, tert-butyl, cyclopentyl, cyclohexyl, —$CH_2OH$, —$CH(OH)CH_3$, —$CH_2CO_2H$, —$CH_2CH_2CO_2H$, —$CH_2CONH_2$, —$CH_2CH_2CONH_2$, —$CH_2CH_2SCH_3$, —$CH_2SH$, —$CH_2(CH_2)_3NH_2$, —$CH_2CH_2CH_2NHC(NH)NH_2$, phenyl, benzyl, 4-hydroxybenzyl, 4-imidazolylmethyl, and 3-indolylmethyl; or $R^5$ and $R^6$ together with the nitrogen atom to which they are bonded form an azetidine, pyrrolidine, or piperidine ring.

In certain of the aforementioned embodiments, each of $R^4$ and $R^5$ is hydrogen; and $R^6$ is selected from methyl, isopropyl, isobutyl, sec-butyl, tert-butyl, and benzyl; in certain embodiments, $R^6$ is isopropyl; and in certain embodiments wherein $R^6$ is isopropyl; the stereochemistry of the carbon to which $R^6$ is bonded is of the S-configuration.

In certain embodiments of compounds of Formula (I), $R^1$ is hydrogen; $R^2$ is

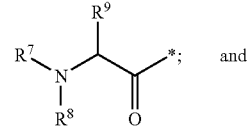

$R^3$ is —$N=C(R^{10})(R^{11})$; and $R^{10}$ and $R^{11}$ are independently selected from hydrogen, alkoxy, substituted alkoxy, alkyl, substituted alkyl, alkylamino, substituted alkylamino, amido, substituted amido, aryl, substituted aryl, arylalkyl, substituted arylalkyl, dialkylamino, substituted dialkylamino, heteroalkyl, substituted heteroalkyl, heteroaryl, substituted heteroaryl, heteroarylalkyl, and substituted heteroarylalkyl.

In certain of the aforementioned embodiments, each of $R^7$ and $R^8$ is hydrogen; and $R^9$ is selected from hydrogen, methyl, isopropyl, isobutyl, sec-butyl, tert-butyl, cyclopentyl, cyclohexyl, —$CH_2OH$, —$CH(OH)CH_3$, —$CH_2CO_2H$, —$CH_2CH_2CO_2H$, —$CH_2CONH_2$, —$CH_2CH_2CONH_2$, —$CH_2CH_2SCH_3$, —$CH_2SH$, —$CH_2(CH_2)_3NH_2$, —$CH_2CH_2CH_2NHC(NH)NH_2$, phenyl, benzyl, 4-hydroxybenzyl, 4-imidazolylmethyl, and 3-indolylmethyl; or $R^8$ and $R^9$ together with the nitrogen atom to which they are bonded form an azetidine, pyrrolidine, or piperidine ring.

In certain of the aforementioned embodiments, each of $R^7$ and $R^8$ is hydrogen; and $R^9$ is selected from methyl, isopropyl, isobutyl, sec-butyl, tert-butyl, and benzyl; in certain embodiments, $R^9$ is isopropyl; and in certain embodiments wherein $R^9$ is isopropyl; the stereochemistry of the carbon to which $R^9$ is bonded is of the S-configuration.

In certain embodiments of compounds of Formula (I), $R^3$ is —$NHR^{12}$, and $R^{12}$ is selected from acyloxyalkylcarbonyl, substituted acyloxyalkylcarbonyl, oxycarbonyl, substituted oxycarbonyl, and a moiety of structural Formula (II):

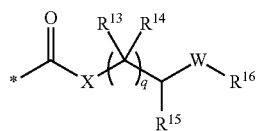

In certain of the aforementioned embodiments, $R^{12}$ is selected from an oxycarbonyl and a substituted oxycarbonyl group having the formula —$C(O)OR^{26}$, wherein $R^{26}$ is selected from $C_{1-6}$ alkyl, $C_{3-7}$ cycloalkyl, aryl, substituted aryl, arylalkyl, substituted arylalkyl, heteroaryl, substituted heteroaryl, and —$CH_2R^{27}$, wherein $R^{27}$ is selected from trifluoromethyl, cyano, $C_{1-4}$ alkanesulfonyl, benzenesulfonyl, and substituted benzenesulfonyl.

In certain of the aforementioned embodiments wherein $R^{12}$ is —$C(O)OR^{26}$, $R^{26}$ is alkyl.

In certain of the aforementioned embodiments wherein $R^{12}$ is —$C(O)OR^{26}$, $R^{26}$ is selected from $C_{3-6}$ alkanyl, $C_{2-6}$ alk-1-en-2-yl, 2-$C_{3-7}$ cycloalkyl-eth-1-en-2-yl, 2-phenyleth-1-en-2-yl, substituted 2-phenyleth-1-en-2-yl, $C_{3-7}$ cycloalkanyl, $C_{5-7}$ cycloalk-1-en-1-yl, phenyl, naphthyl, halophenyl, methoxyphenyl, cyanophenyl, carboxyphenyl, $C_{1-4}$ alkoxycarbonylphenyl, aminophenyl, halobenzyl, methoxybenzyl, cyanobenzyl, carboxybenzyl, $C_{1-4}$ alkoxycarbonylbenzyl, aminobenzyl, furyl, thienyl, pyrrolyl, imidazoyl, oxazolyl, pyridyl, pyrimidyl, pyrazinyl, and triazinyl.

In certain of the aforementioned embodiments, wherein $R^{12}$ is —$C(O)OR^{26}$; $R^{26}$ is selected from butyl, isobutyl, sec-butyl, pent-1-yl, pent-2-yl, pent-3-yl, 2-methylbut-1-yl, 3-methylbut-1-yl, hex-1-yl, hex-2-yl, hex-3-yl, 2-methylpent-1-yl, 3-methylpent-1-yl, vinyl, propen-2-yl, buten-2-yl, phenethen-2-yl, cyclopentyl, cyclohexyl, cyclopenten-1-yl, cyclohexen-1-yl, phenyl, 4-methoxyphenyl, 4-methoxybenzyl, 1,1,1-trifluoroethyl, and cyanomethyl.

In certain embodiments of a compound of Formula (I), $R^1$ is selected from hydrogen, —$C(O)R^{19}$, —$C(O)OR^{20}$, and

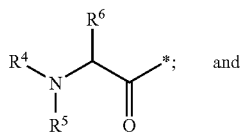 and $R^2$ is selected from hydrogen, —$C(O)R^{19}$, —$C(O)OR^{20}$, and

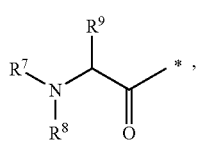

wherein each of $R^4$ and $R^5$ is hydrogen; $R^6$ is selected from hydrogen, methyl, isopropyl, isobutyl, sec-butyl, tert-butyl, cyclopentyl, cyclohexyl, —$CH_2OH$, —$CH(OH)CH_3$, —$CH_2CO_2H$, —$CH_2CH_2CO_2H$, —$CH_2CONH_2$, —$CH_2CH_2CONH_2$, —$CH_2CH_2SCH_3$, —$CH_2SH$, —$CH_2(CH_2)_3NH_2$, —$CH_2CH_2CH_2NHC(NH)NH_2$, phenyl, benzyl, 4-hydroxybenzyl, 4-imidazolylmethyl, and 3-indolylmethyl; or $R^5$ and $R^6$ together with the nitrogen atom to which they are bonded form an azetidine, pyrrolidine, or piperidine ring;

each of $R^7$ and $R^8$ is hydrogen; $R^9$ is selected from hydrogen, methyl, isopropyl, isobutyl, sec-butyl, tert-butyl, cyclopentyl, cyclohexyl, —$CH_2OH$, —$CH(OH)CH_3$, —$CH_2CO_2H$, —$CH_2CH_2CO_2H$, —$CH_2CONH_2$, —$CH_2CH_2CONH_2$, —$CH_2CH_2SCH_3$, —$CH_2SH$, —$CH_2(CH_2)_3NH_2$, —$CH_2CH_2CH_2NHC(NH)NH_2$, phenyl, benzyl, 4-hydroxybenzyl, 4-imidazolylmethyl, and r 3-indolylmethyl; or $R^8$ and $R^9$ together with the nitrogen atom to which they are bonded form an azetidine, pyrrolidine, or piperidine ring; and each of $R^{19}$ and $R^{20}$ is $C_{1-6}$ alkyl.

In certain of the aforementioned embodiments, each of $R^1$ and $R^2$ is hydrogen, $R^{12}$ is —$C(O)OR^{26}$, and $R^{26}$ is selected from butyl, isobutyl, sec-butyl, pent-1-yl, pent-2-yl, pent-3-yl, 2-methylbut-1-yl, 3-methylbut-1-yl, hex-1-yl, hex-2-yl, hex-3-yl, 2-methylpent-1-yl, 3-methylpent-1-yl, vinyl, propen-2-yl, buten-2-yl, phenethen-2-yl, cyclopentyl, cyclohexyl, cyclopenten-1-yl, cyclohexen-1-yl, phenyl, 4-methoxyphenyl, 4-methoxybenzyl, 1,1,1-trifluoroethyl, and cyanomethyl.

In certain of the aforementioned embodiments, $R^1$ is

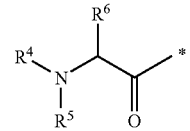

$R^2$ is hydrogen; each of $R^4$ and $R^5$ is hydrogen; $R^6$ is selected from methyl, isopropyl, isobutyl, sec-butyl, tert-butyl, and benzyl; $R^{12}$ is —$C(O)OR^{26}$; and $R^{26}$ is selected from butyl, isobutyl, sec-butyl, pent-1-yl, pent-2-yl, pent-3-yl, 2-methylbut-1-yl, 3-methylbut-1-yl, hex-1-yl, hex-2-yl, hex-3-yl, 2-methylpent-1-yl, 3-methylpent-1-yl, vinyl, propen-2-yl, buten-2-yl, phenethen-2-yl, cyclopentyl, cyclohexyl, cyclopenten-1-yl, cyclohexen-1-yl, phenyl, 4-methoxyphenyl, 4-methoxybenzyl, 1,1,1-trifluoroethyl, and cyanomethyl. In certain embodiments, $R^6$ is isopropyl, and in certain embodiments, the stereochemistry of the carbon to which $R^6$ is bonded is of the S-configuration.

In certain embodiments of compounds of Formula (I), $R^1$ is

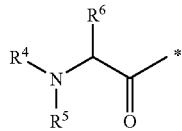

$R^2$ is hydrogen; and
$R^3$ is —$NHR^{12}$; wherein
$R^{12}$ is selected from acyloxyalkylcarbonyl, substituted acyloxyalkylcarbonyl, oxycarbonyl, substituted oxycarbonyl, and a moiety of structural Formula (II).

In certain of the aforementioned embodiments, each of $R^4$ and $R^5$ is hydrogen; and $R^6$ is selected from hydrogen, methyl, isopropyl, isobutyl, sec-butyl, tert-butyl, cyclopentyl, cyclohexyl, —$CH_2OH$, —$CH(OH)CH_3$, —$CH_2CO_2H$, —$CH_2CH_2CO_2H$, —$CH_2CONH_2$, —$CH_2CH_2CONH_2$, —$CH_2CH_2SCH_3$, —$CH_2SH$, —$CH_2(CH_2)_3NH_2$, —$CH_2CH_2CH_2NHC(NH)NH_2$, phenyl, benzyl, 4-hydroxybenzyl, 4-imidazolylmethyl, and 3-indolylmethyl; or $R^5$ and $R^6$ together with the nitrogen atom to which they are bonded form an azetidine, pyrrolidine, or piperidine ring.

In certain of the aforementioned embodiments, each of $R^4$ and $R^5$ is hydrogen; $R^6$ is selected from methyl, isopropyl, isobutyl, sec-butyl, tert-butyl, and benzyl; in certain embodiments, $R^6$ is isopropyl; and in certain embodiments wherein $R^6$ is isopropyl, the stereochemistry of the carbon to which $R^6$ is bonded is of the S-configuration.

In certain embodiments of compounds of Formula (I), $R^1$ is

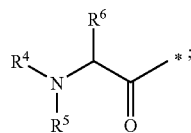

$R^2$ is hydrogen; and
$R^3$ is —$NHR^{12}$; wherein:
$R^{12}$ is —$C(O)OR^{26}$, wherein $R^{26}$ is selected from $C_{1-6}$ alkyl, $C_{3-7}$ cycloalkyl, aryl, substituted aryl, arylalkyl, substituted arylalkyl, heteroaryl, substituted heteroaryl, and —$CH_2R^{27}$, wherein $R^{27}$ is selected from trifluoromethyl, cyano, $C_{1-4}$ alkanesulfonyl, benzenesulfonyl, and substituted benzenesulfonyl.

In certain of the aforementioned embodiments, each of $R^4$ and $R^5$ is hydrogen; and $R^6$ is selected from hydrogen, methyl, isopropyl, isobutyl, sec-butyl, tert-butyl, cyclopentyl, cyclohexyl, —$CH_2OH$, —$CH(OH)CH_3$, —$CH_2CO_2H$, —$CH_2CH_2CO_2H$, —$CH_2CONH_2$, —$CH_2CH_2CONH_2$, —$CH_2CH_2SCH_3$, —$CH_2SH$, —$CH_2(CH_2)_3NH_2$, —$CH_2CH_2CH_2NHC(NH)NH_2$, phenyl, benzyl, 4-hydroxybenzyl, 4-imidazolylmethyl, and 3-indolylmethyl; or $R^5$ and $R^6$ together with the nitrogen atom to which they are bonded form an azetidine, pyrrolidine, or piperidine ring.

In certain of the aforementioned embodiments, each of $R^4$ and $R^5$ is hydrogen; $R^6$ is selected from methyl, isopropyl, isobutyl, sec-butyl, tert-butyl, and benzyl; in certain embodiments, $R^6$ is isopropyl; and in certain embodiments wherein $R^6$ is isopropyl, the stereochemistry of the carbon to which $R^6$ is bonded is of the S-configuration.

In certain embodiments of compounds of Formula (I), $R^1$ is

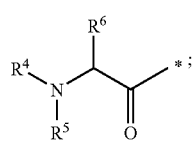

$R^2$ is hydrogen; and
$R^3$ is —$NHR^{12}$; wherein
$R^{12}$ is —$C(O)OR^{26}$ wherein $R^{26}$ is $C_{1-6}$ alkyl.

In certain of the aforementioned embodiments, each of $R^4$ and $R^5$ is hydrogen; and $R^6$ is selected from hydrogen, methyl, isopropyl, isobutyl, sec-butyl, tert-butyl, cyclopentyl, cyclohexyl, —$CH_2OH$, —$CH(OH)CH_3$, —$CH_2CO_2H$, —$CH_2CH_2CO_2H$, —$CH_2CONH_2$, —$CH_2CH_2CONH_2$, —$CH_2CH_2SCH_3$, —$CH_2SH$, —$CH_2(CH_2)_3NH_2$, —$CH_2CH_2CH_2NHC(NH)NH_2$, phenyl, benzyl, 4-hydroxybenzyl, 4-imidazolylmethyl, and 3-indolylmethyl; or $R^5$ and $R^6$ together with the nitrogen atom to which they are bonded form an azetidine, pyrrolidine, or piperidine ring.

In certain of the aforementioned embodiments, each of $R^4$ and $R^5$ is hydrogen; $R^6$ is selected from methyl, isopropyl, isobutyl, sec-butyl, tert-butyl, and benzyl; in certain embodiments, $R^6$ is isopropyl; and in certain embodiments wherein $R^6$ is isopropyl, the stereochemistry of the carbon to which $R^6$ is bonded is of the S-configuration.

In certain embodiments of compounds of Formula (I), $R^1$ is

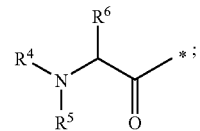

$R^2$ is hydrogen; and
$R^3$ is —$NHR^{12}$; wherein
$R^{12}$ is —$C(O)OR^{26}$, wherein $R^{26}$ is selected from butyl, isobutyl, sec-butyl, pent-1-yl, pent-2-yl, pent-3-yl, 2-methylbut-1-yl, 3-methylbut-1-yl, hex-1-yl, hex-2-yl, hex-3-yl, 2-methylpent-1-yl, 3-methylpent-1-yl, vinyl, propen-2-yl, buten-2-yl, phenethen-2-yl, cyclopentyl, cyclohexyl, cyclopenten-1-yl, cyclohexen-1-yl, phenyl, 4-methoxyphenyl, 4-methoxybenzyl, 1,1,1-trifluoroethyl, and cyanomethyl.

In certain of the aforementioned embodiments, each of $R^4$ and $R^5$ is hydrogen; and $R^6$ is selected from hydrogen, methyl, isopropyl, isobutyl, sec-butyl, tert-butyl, cyclopentyl, cyclohexyl, —$CH_2OH$, —$CH(OH)CH_3$, —$CH_2CO_2H$, —$CH_2CH_2CO_2H$, —$CH_2CONH_2$, —$CH_2CH_2CONH_2$, —$CH_2CH_2SCH_3$, —$CH_2SH$, —$CH_2(CH_2)_3NH_2$, —$CH_2CH_2CH_2NHC(NH)NH_2$, phenyl, benzyl, 4-hydroxybenzyl, 4-imidazolylmethyl, and 3-indolylmethyl; or $R^5$ and $R^6$ together with the nitrogen atom to which they are bonded form an azetidine, pyrrolidine, or piperidine ring.

In certain of the aforementioned embodiments, each of $R^4$ and $R^5$ is hydrogen; $R^6$ is selected from methyl, isopropyl, isobutyl, sec-butyl, tert-butyl, and benzyl; in certain embodiments, $R^6$ is isopropyl; and in certain embodiments wherein $R^6$ is isopropyl, the stereochemistry of the carbon to which $R^6$ is bonded is of the S-configuration.

In certain embodiments of compounds of Formula (I), $R^1$ is hydrogen; $R^2$ is

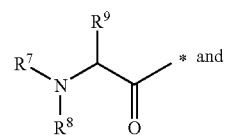

$R^3$ is —$NHR^{12}$; wherein
$R^{12}$ is selected from acyloxyalkylcarbonyl, substituted acyloxyalkylcarbonyl, oxycarbonyl, substituted oxycarbonyl, and a moiety of structural Formula (II).

In certain of the aforementioned embodiments, each of $R^4$ and $R^5$ is hydrogen; and $R^6$ is selected from hydrogen, methyl, isopropyl, isobutyl, sec-butyl, tert-butyl, cyclopentyl, cyclohexyl, —$CH_2OH$, —$CH(OH)CH_3$, —$CH_2CO_2H$, —$CH_2CH_2CO_2H$, —$CH_2CONH_2$, —$CH_2CH_2CONH_2$, —$CH_2CH_2SCH_3$, —$CH_2SH$, —$CH_2(CH_2)_3NH_2$, —$CH_2CH_2CH_2NHC(NH)NH_2$, phenyl, benzyl, 4-hydroxybenzyl, 4-imidazolylmethyl, and 3-indolylmethyl; or $R^5$ and $R^6$ together with the nitrogen atom to which they are bonded form an azetidine, pyrrolidine, or piperidine ring.

In certain of the aforementioned embodiments, each of $R^4$ and $R^5$ is hydrogen; $R^6$ is selected from methyl, isopropyl, isobutyl, sec-butyl, tert-butyl, and benzyl; in certain embodiments, $R^6$ is isopropyl; and in certain embodiments wherein $R^6$ is isopropyl, the stereochemistry of the carbon to which $R^6$ is bonded is of the S-configuration.

In certain embodiments of compounds of Formula (I), $R^1$ is

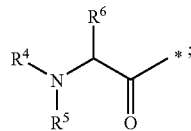

$R^2$ is hydrogen; and
$R^3$ is —$NHR^{12}$; wherein
$R^{12}$ is —$C(O)OR^{26}$, wherein $R^{26}$ is selected from $C_{16}$ alkyl, $C_{3-7}$ cycloalkyl, aryl, substituted aryl, arylalkyl, substituted arylalkyl, heteroaryl, substituted heteroaryl, and —$CH_2R^{27}$, wherein $R^{27}$ is selected from trifluoromethyl, cyano, $C_{1-4}$ alkanesulfonyl, benzenesulfonyl, and substituted benzenesulfonyl.

In certain of the aforementioned embodiments, each of $R^4$ and $R^5$ is hydrogen; and $R^6$ is selected from hydrogen, methyl, isopropyl, isobutyl, sec-butyl, tert-butyl, cyclopentyl, cyclohexyl, —$CH_2OH$, —$CH(OH)CH_3$, —$CH_2CO_2H$, —$CH_2CH_2CO_2H$, —$CH_2CONH_2$, —$CH_2CH_2CONH_2$, —$CH_2CH_2SCH_3$, —$CH_2SH$, —$CH_2(CH_2)_3NH_2$, —$CH_2CH_2CH_2NHC(NH)NH_2$, phenyl, benzyl, 4-hydroxybenzyl, 4-imidazolylmethyl, and 3-indolylmethyl; or $R^5$ and $R^6$ together with the nitrogen atom to which they are bonded form an azetidine, pyrrolidine, or piperidine ring.

In certain of the aforementioned embodiments, each of $R^4$ and $R^5$ is hydrogen; $R^6$ is selected from methyl, isopropyl, isobutyl, sec-butyl, tert-butyl, and benzyl; in certain embodiments, $R^6$ is isopropyl; and in certain embodiments wherein $R^6$ is isopropyl, the stereochemistry of the carbon to which $R^6$ is bonded is of the S-configuration.

In certain embodiments of compounds of Formula (I), $R^1$ is

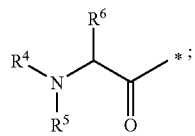

$R^2$ is hydrogen; and
$R^3$ is —$NHR^{12}$; wherein
$R^{12}$ is —$C(O)OR^{26}$, wherein $R^{26}$ is $C_{1-6}$ alkyl.

In certain of the aforementioned embodiments, each of $R^4$ and $R^5$ is hydrogen; and $R^6$ is selected from hydrogen, methyl, isopropyl, isobutyl, sec-butyl, tert-butyl, cyclopentyl, cyclohexyl, —$CH_2OH$, —$CH(OH)CH_3$, —$CH_2CO_2H$, —$CH_2CH_2CO_2H$, —$CH_2CONH_2$, —$CH_2CH_2CONH_2$, —$CH_2CH_2SCH_3$, —$CH_2SH$, —$CH_2(CH_2)_3NH_2$, —$CH_2CH_2CH_2NHC(NH)NH_2$, phenyl, benzyl, 4-hydroxybenzyl, 4-imidazolylmethyl, and 3-indolylmethyl; or $R^5$ and $R^6$ together with the nitrogen atom to which they are bonded form an azetidine, pyrrolidine, or piperidine ring.

In certain of the aforementioned embodiments, each of $R^4$ and $R^5$ is hydrogen; $R^6$ is selected from methyl, isopropyl, isobutyl, sec-butyl, tert-butyl, and benzyl; in certain embodiments, $R^6$ is isopropyl; and in certain embodiments wherein $R^6$ is isopropyl, the stereochemistry of the carbon to which $R^6$ is bonded is of the S-configuration.

In certain embodiments of compounds of Formula (I), $R^1$ is

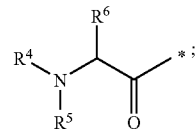

$R^2$ is hydrogen; and
$R^3$ is —$NHR^{12}$; wherein
$R^{12}$ is —$C(O)OR^{26}$, wherein
$R^{26}$ is selected from butyl, isobutyl, sec-butyl, pent-1-yl, pent-2-yl, pent-3-yl, 2-methylbut-1-yl, 3-methylbut-1-yl, hex-1-yl, hex-2-yl, hex-3-yl, 2-methylpent-1-yl, 3-methylpent-1-yl, vinyl, propen-2-yl, buten-2-yl, phenethen-2-yl, cyclopentyl, cyclohexyl, cyclopenten-1-yl, cyclohexen-1-yl, phenyl, 4-methoxyphenyl, 4-methoxybenzyl, 1,1,1-trifluoroethyl, and cyanomethyl.

In certain of the aforementioned embodiments, each of $R^4$ and $R^5$ is hydrogen; and $R^6$ is selected from hydrogen, methyl, isopropyl, isobutyl, sec-butyl, tert-butyl, cyclopentyl, cyclohexyl, —$CH_2OH$, —$CH(OH)CH_3$, —$CH_2CO_2H$, —$CH_2CH_2CO_2H$, —$CH_2CONH_2$, —$CH_2CH_2CONH_2$, —$CH_2CH_2SCH_3$, —$CH_2SH$, —$CH_2(CH_2)_3NH_2$, —$CH_2CH_2CH_2NHC(NH)NH_2$, phenyl, benzyl, 4-hydroxybenzyl, 4-imidazolylmethyl, and 3-indolylmethyl; or $R^5$ and $R^6$ together with the nitrogen atom to which they are bonded form an azetidine, pyrrolidine, or piperidine ring.

In certain of the aforementioned embodiments, each of $R^4$ and $R^5$ is hydrogen; $R^6$ is selected from methyl, isopropyl, isobutyl, sec-butyl, tert-butyl, and benzyl; in certain embodiments, $R^6$ is isopropyl; and in certain embodiments wherein $R^6$ is isopropyl, the stereochemistry of the carbon to which $R^6$ is bonded is of the S-configuration.

In certain of the aforementioned embodiments, $R^1$ is hydrogen; $R^2$ is

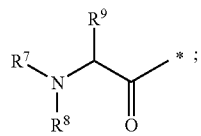

each of $R^7$ and $R^8$ is hydrogen; and $R^9$ is selected from methyl, isopropyl, isobutyl, sec-butyl, tert-butyl, and benzyl; $R^{12}$ is —$C(O)OR^{26}$; and $R^{26}$ is selected from butyl, isobutyl, sec-butyl, pent-1-yl, pent-2-yl, pent-3-yl, 2-methylbut-1-yl, 3-methylbut-1-yl, hex-1-yl, hex-2-yl, hex-3-yl, 2-methylpent-1-yl, 3-methylpent-1-yl, vinyl, propen-2-yl, buten-2-yl, phenethen-2-yl, cyclopentyl, cyclohexyl, cyclopenten-1-yl, cyclohexen-1-yl, phenyl, 4-methoxyphenyl, 4-methoxybenzyl, 1,1,1-trifluoroethyl, and cyanomethyl. In certain of the aforementioned embodiments, $R^9$ is isopropyl, and in certain embodiments wherein $R^9$ is isopropyl, the stereochemistry of the carbon to which $R^9$ is bonded is of the S-configuration.

In certain embodiments of compounds of Formula (I),
R[1] is selected from hydrogen, acyl, substituted acyl, acyloxyalkylcarbonyl, substituted acyloxyalkylcarbonyl, oxycarbonyl, substituted oxycarbonyl, and

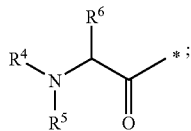

R[2] is selected from hydrogen, acyl, substituted acyl, acyloxyalkylcarbonyl, substituted acyloxyalkylcarbonyl, oxycarbonyl, substituted oxycarbonyl, and

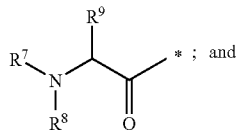

R[3] is —NHR[12], wherein R[12] is

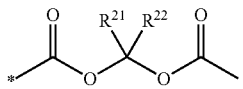

wherein R[21] and R[22] are independently selected from hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, cycloalkoxycarbonyl, substituted cycloalkoxycarbonyl, heteroaryl, substituted heteroaryl, heteroarylalkyl, and substituted heteroarylalkyl; or R[21] and R[22] together with the carbon atom to which they are bonded form a cycloalkyl, substituted cycloalkyl, cycloheteroalkyl, or substituted cycloheteroalkyl ring; and R[23] is selected from acyl, substituted acyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, and substituted heteroarylalkyl.

In certain of the aforementioned embodiments, R[21] and R[22] are independently selected from hydrogen, $C_{1-4}$ alkyl, substituted $C_{1-4}$ alkyl, $C_{1-4}$ alkoxycarbonyl, $C_{3-6}$ cycloalkyl, $C_{3-6}$ cycloalkoxycarbonyl, phenyl, substituted phenyl, $C_{7-9}$ phenylalkyl, and pyridyl; or R[21] and R[22] together with the carbon atom to which they are bonded form a $C_{3-6}$ cycloalkyl ring; and
R[23] is selected from $C_{1-6}$ alkyl, substituted $C_{1-6}$ alkyl, $C_{3-6}$ cycloalkyl, phenyl, substituted phenyl, $C_{7-9}$ phenylalkyl, pyridyl, and substituted pyridyl.

In certain of the aforementioned embodiments, R[21] is selected from hydrogen, methyl, ethyl, propyl, isopropyl, butyl, isobutyl, sec-butyl, tert-butyl, cyclopentyl, cyclohexyl, phenyl, benzyl, phenethyl, and 3-pyridyl;
R[22] is hydrogen; and
R[23] is selected from methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, 1,1-dimethoxyethyl, 1,1-diethoxyethyl, phenyl, 2-methylphenyl, 2,6-dimethylphenyl, 2-methoxyphenyl, 4-methoxyphenyl, 2,6-dimethoxyphenyl, benzyl, phenethyl, styryl, cyclopropyl, cyclobutyl, cyclopentyl, cyclohexyl, and 3-pyridyl.

In certain of the aforementioned embodiments, R[21] is selected from hydrogen, methyl, ethyl, propyl, isopropyl, butyl, isobutyl, sec-butyl, tert-butyl, cyclopentyl, cyclohexyl, phenyl, benzyl, phenethyl, and 3-pyridyl;
R[22] is hydrogen;
R[23] is selected from methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, 1,1-dimethoxyethyl, 1,1-diethoxyethyl, phenyl, 2-methylphenyl, 2,6-dimethylphenyl, 2-methoxyphenyl, 4-methoxyphenyl, 2,6-dimethoxyphenyl, benzyl, phenethyl, styryl, cyclopropyl, cyclobutyl, cyclopentyl, cyclohexyl, and 3-pyridyl; and
each of R[1] and R[2] is hydrogen.

certain of the aforementioned embodiments, R[21] is selected from hydrogen, methyl, propyl, and tert-butyl;
R[22] is hydrogen;
R[23] is selected from methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, 1,1-dimethoxyethyl, 1,1-diethoxyethyl, phenyl, 2-methylphenyl, 2,6-dimethylphenyl, 2-methoxyphenyl, 4-methoxyphenyl, 2,6-dimethoxyphenyl, benzyl, phenethyl, styryl, cyclopropyl, cyclobutyl, cyclopentyl, cyclohexyl, and 3-pyridyl; and
each of R[1] and R[2] is hydrogen.

In certain of the aforementioned embodiments, R[21] is methyl;
R[22] is hydrogen;
R[23] is selected from methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, 1,1-dimethoxyethyl, 1,1-diethoxyethyl, phenyl, 2-methylphenyl, 2,6-dimethylphenyl, 2-methoxyphenyl, 4-methoxyphenyl, 2,6-dimethoxyphenyl, benzyl, phenethyl, styryl, cyclopropyl, cyclobutyl, cyclopentyl, cyclohexyl, and 3-pyridyl; and
each of R[1] and R[2] is hydrogen.

In certain embodiments of compounds of Formula (I), R[1] is

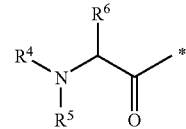

R[2] is hydrogen; and
R[3] is —NHR[12], wherein R[12] is

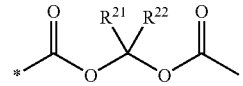

wherein R[21] is selected from hydrogen, methyl, ethyl, propyl, isopropyl, butyl, isobutyl, sec-butyl, tert-butyl, cyclopentyl, cyclohexyl, phenyl, benzyl, phenethyl, and 3-pyridyl;
R[22] is hydrogen; and
R[23] is selected from methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, 1,1-dimethoxyethyl, 1,1-diethoxyethyl, phenyl, 2-methylphenyl, 2,6-dimethylphenyl, 2-methoxyphenyl, 4-methoxyphenyl, 2,6-dimethoxyphenyl, benzyl, phenethyl, styryl, cyclopropyl, cyclobutyl, cyclopentyl, cyclohexyl, and 3-pyridyl.

In certain of the aforementioned embodiments, each of $R^4$ and $R^5$ is hydrogen; $R^6$ is selected from hydrogen, methyl, isopropyl, isobutyl, sec-butyl, tert-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl, and 3-indolylmethyl; or $R^5$ and $R^6$ together with the nitrogen atom to which they are bonded form an azetidine, pyrrolidine, or piperidine ring.

In certain of the aforementioned embodiments, each of $R^4$ and $R^5$ is hydrogen; $R^6$ is selected from methyl, isopropyl, isobutyl, sec-butyl, tert-butyl, and benzyl; in certain embodiments $R^6$ is isopropyl; and in certain embodiments wherein $R^6$ is isopropyl, the stereochemistry of the carbon to which $R^6$ is bonded is of the S-configuration.

In certain embodiments of compounds of Formula (I), $R^1$ is

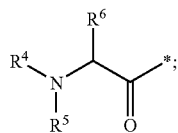

$R^2$ is hydrogen; and
$R^3$ is —NHR$^{12}$, wherein $R^{12}$ is

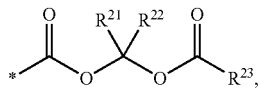

wherein $R^{21}$ is selected from hydrogen, methyl, propyl, isopropyl, and tert-butyl;

$R^{22}$ is hydrogen; and $R^{23}$ is selected from methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, 1,1-dimethoxyethyl, 1,1-diethoxyethyl, phenyl, 2-methylphenyl, 2,6-dimethylphenyl, 2-methoxyphenyl, 4-methoxyphenyl, 2,6-dimethoxyphenyl, benzyl, phenethyl, styryl, cyclopropyl, cyclobutyl, cyclopentyl, cyclohexyl, and 3-pyridyl.

In certain of the aforementioned embodiments, each of $R^4$ and $R^5$ is hydrogen; $R^6$ is selected from hydrogen, methyl, isopropyl, isobutyl, sec-butyl, tert-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl, and 3-indolylmethyl; or $R^5$ and $R^6$ together with the nitrogen atom to which they are bonded form an azetidine, pyrrolidine, or piperidine ring.

In certain of the aforementioned embodiments, each of $R^4$ and $R^5$ is hydrogen; $R^6$ is selected from methyl, isopropyl, isobutyl, sec-butyl, tert-butyl, and benzyl; in certain embodiments $R^6$ is isopropyl; and in certain embodiments wherein $R^6$ is isopropyl, the stereochemistry of the carbon to which $R^6$ is bonded is of the S-configuration.

In certain embodiments of compounds of Formula (I), $R^1$ is

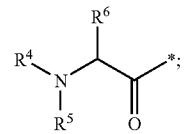

$R^2$ is hydrogen; and
$R^3$ is —NHR$^{12}$, wherein $R^{12}$ is

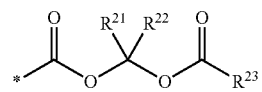

wherein $R^{21}$ methyl;

$R^{22}$ is hydrogen; and $R^{23}$ is selected from methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, 1,1-dimethoxyethyl, 1,1-diethoxyethyl, phenyl, 2-methylphenyl, 2,6-dimethylphenyl, 2-methoxyphenyl, 4-methoxyphenyl, 2,6-dimethoxyphenyl, benzyl, phenethyl, styryl, cyclopropyl, cyclobutyl, cyclopentyl, cyclohexyl, and 3-pyridyl.

In certain of the aforementioned embodiments, each of $R^4$ and $R^5$ is hydrogen; $R^6$ is selected from hydrogen, methyl, isopropyl, isobutyl, sec-butyl, tert-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl, and 3-indolylmethyl; or $R^5$ and $R^6$ together with the nitrogen atom to which they are bonded form an azetidine, pyrrolidine, or piperidine ring.

In certain of the aforementioned embodiments, each of $R^4$ and $R^5$ is hydrogen; $R^6$ is selected from methyl, isopropyl, isobutyl, sec-butyl, tert-butyl, and benzyl; in certain embodiments $R^6$ is isopropyl; and in certain embodiments wherein $R^6$ is isopropyl, the stereochemistry of the carbon to which $R^6$ is bonded is of the S-configuration.

In certain embodiments of compounds of Formula (I), $R^1$ is hydrogen; $R^2$ is

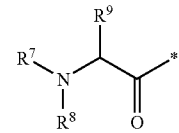

$R^3$ is —NHR$^{12}$, wherein $R^{12}$ is

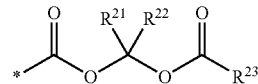

wherein $R^{21}$ is selected from hydrogen, methyl, ethyl, propyl, isopropyl, butyl, isobutyl, sec-butyl, tert-butyl, cyclopentyl, cyclohexyl, phenyl, benzyl, phenethyl, and 3-pyridyl;

$R^{22}$ is hydrogen; and $R^{23}$ is selected from methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, 1,1-dimethoxyethyl, 1,1-diethoxyethyl, phenyl, 2-methylphenyl, 2,6-dimethylphenyl, 2-methoxyphenyl, 4-methoxyphenyl, 2,6-dimethoxyphenyl, benzyl, phenethyl, styryl, cyclopropyl, cyclobutyl, cyclopentyl, cyclohexyl, and 3-pyridyl.

In certain of the aforementioned embodiments, each of $R^7$ and $R^8$ is hydrogen; $R^9$ is selected from hydrogen, methyl, isopropyl, isobutyl, sec-butyl, tert-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl, and 3-indolylmethyl; or $R^8$ and $R^9$ together with the nitrogen atom to which they are bonded form an azetidine, pyrrolidine, or piperidine ring.

In certain of the aforementioned embodiments, each of $R^7$ and $R^8$ is hydrogen; $R^9$ is selected from methyl, isopropyl, isobutyl, sec-butyl, tert-butyl, and benzyl; in certain embodiments $R^9$ is isopropyl; and in certain embodiments wherein $R^9$ is isopropyl, the stereochemistry of the carbon to which $R^9$ is bonded is of the S-configuration.

In certain embodiments of compounds of Formula (I), $R^1$ is hydrogen; $R^2$ is

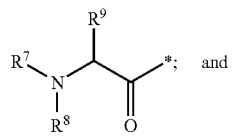

$R^3$ is —NHR$^{12}$, wherein $R^{12}$ is

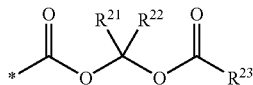

wherein $R^{21}$ is selected from hydrogen, methyl, propyl, isopropyl, and tert-butyl;

$R^{22}$ is hydrogen; and $R^{23}$ is selected from methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, 1,1-dimethoxyethyl, 1,1-diethoxyethyl, phenyl, 2-methylphenyl, 2,6-dimethylphenyl, 2-methoxyphenyl, 4-methoxyphenyl, 2,6-dimethoxyphenyl, benzyl, phenethyl, styryl, cyclopropyl, cyclobutyl, cyclopentyl, cyclohexyl, and 3-pyridyl.

In certain of the aforementioned embodiments, each of $R^7$ and $R^8$ is hydrogen; $R^9$ is selected from hydrogen, methyl, isopropyl, isobutyl, sec-butyl, tert-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl, and 3-indolylmethyl; or $R^8$ and $R^9$ together with the nitrogen atom to which they are bonded form an azetidine, pyrrolidine, or piperidine ring.

In certain of the aforementioned embodiments, each of $R^7$ and $R^8$ is hydrogen; $R^9$ is selected from methyl, isopropyl, isobutyl, sec-butyl, tert-butyl, and benzyl; in certain embodiments $R^9$ is isopropyl; and in certain embodiments wherein $R^9$ is isopropyl, the stereochemistry of the carbon to which $R^9$ is bonded is of the S-configuration.

In certain embodiments of compounds of Formula (I), $R^1$ is hydrogen; $R^2$ is

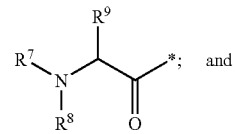

$R^3$ is —NHR$^{12}$, wherein $R^{12}$ is

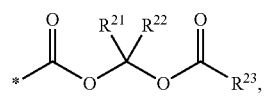

wherein $R^{21}$ is methyl;

$R^{22}$ is hydrogen; and $R^{23}$ is selected from methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, 1,1-dimethoxyethyl, 1,1-diethoxyethyl, phenyl, 2-methylphenyl, 2,6-dimethylphenyl, 2-methoxyphenyl, 4-methoxyphenyl, 2,6-dimethoxyphenyl, benzyl, phenethyl, styryl, cyclopropyl, cyclobutyl, cyclopentyl, cyclohexyl, and 3-pyridyl.

In certain of the aforementioned embodiments, each of $R^7$ and $R^8$ is hydrogen; $R^9$ is selected from hydrogen, methyl, isopropyl, isobutyl, sec-butyl, tert-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl, and 3-indolylmethyl; or $R^8$ and $R^9$ together with the nitrogen atom to which they are bonded form an azetidine, pyrrolidine, or piperidine ring.

In certain of the aforementioned embodiments, each of $R^7$ and $R^8$ is hydrogen; $R^9$ is selected from methyl, isopropyl, isobutyl, sec-butyl, tert-butyl, and benzyl; in certain embodiments $R^9$ is isopropyl; and in certain embodiments wherein $R^9$ is isopropyl, the stereochemistry of the carbon to which $R^9$ is bonded is of the S-configuration.

In certain embodiments of compounds of Formula (I), $R^3$ is —NHR$^{12}$, wherein $R^{12}$ is selected from an acyloxyalkylcarbonyl and a substituted acyloxyalkylcarbonyl group having the formula:

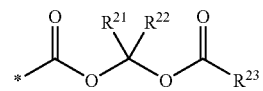

wherein $R^{21}$ and $R^{22}$ are independently selected from hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, cycloalkoxycarbonyl, substituted cycloalkoxycarbonyl, heteroaryl, substituted heteroaryl, heteroarylalkyl, and substituted heteroarylalkyl; or $R^{21}$ and $R^{22}$ together with the carbon atom to which they are bonded form a cycloalkyl, substituted cycloalkyl, cycloheteroalkyl, or substituted cycloheteroalkyl ring; and $R^{23}$ is selected from acyl, substituted acyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, and substituted heteroarylalkyl.

In certain of the aforementioned embodiments, $R^{21}$ and $R^{22}$ are independently selected from hydrogen, $C_{1-4}$ alkyl, substituted $C_{1-4}$ alkyl, $C_{1-4}$ alkoxycarbonyl, $C_{3-6}$ cycloalkyl, $C_{3-6}$ cycloalkoxycarbonyl, phenyl, substituted phenyl, $C_{7-9}$ phenylalkyl, and pyridyl; or $R^{21}$ and $R^{22}$ together with the carbon atom to which they are bonded form a $C_{3-6}$ cycloalkyl ring; and $R^{23}$ is selected from $C_{1-6}$ alkyl, substituted $C_{1-6}$ alkyl, $C_{3-6}$ cycloalkyl, phenyl, substituted phenyl, $C_{7-9}$ phenylalkyl, pyridyl, and substituted pyridyl.

In certain of the aforementioned embodiments, $R^{21}$ is selected from hydrogen, methyl, ethyl, propyl, isopropyl, butyl, isobutyl, sec-butyl, tert-butyl, cyclopentyl, cyclohexyl, phenyl, benzyl, phenethyl, and 3-pyridyl; and $R^{23}$ is hydrogen, or $R^{21}$ and $R^{22}$ together with the atom to which they are bonded form a cyclobutyl, cyclopentyl, or a cyclohexyl ring.

In certain of the aforementioned embodiments, $R^{21}$ is selected from hydrogen, methyl, ethyl, propyl, isopropyl, butyl, isobutyl, sec-butyl, tert-butyl, cyclopentyl, cyclohexyl, phenyl, benzyl, phenethyl, and 3-pyridyl; and $R^{22}$ is hydrogen.

In certain of the aforementioned embodiments, $R^{23}$ is selected from methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, 1,1-dimethoxyethyl, 1,1-diethoxyethyl, phenyl, 2-methylphenyl, 2,6-dimethylphenyl, 2-methoxyphenyl, 4-methoxyphenyl, 2,6-dimethoxyphenyl, benzyl, phenethyl, styryl, cyclopropyl, cyclobutyl, cyclopentyl, cyclohexyl, and 3-pyridyl.

In certain of the aforementioned embodiments, $R^{21}$ is selected from hydrogen, methyl, propyl, isopropyl, and tert-butyl, $R^{22}$ is hydrogen, and $R^{23}$ is selected from methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, 1,1-dimethoxyethyl, 1,1-diethoxyethyl, phenyl, 2-methylphenyl, 2,6-dimethylphenyl, 2-methoxyphenyl, 4-methoxyphenyl, 2,6-dimethoxyphenyl, benzyl, phenethyl, styryl, cyclopropyl, cyclobutyl, cyclopentyl, cyclohexyl, and 3-pyridyl.

In certain of the aforementioned embodiments, $R^{21}$ is methyl, $R^{22}$ is hydrogen, and $R^{23}$ is selected from methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, 1,1-dimethoxyethyl, 1,1-diethoxyethyl, phenyl, 2-methylphenyl, 2,6-dimethylphenyl, 2-methoxyphenyl, 4-methoxyphenyl, 2,6-dimethoxyphenyl, benzyl, phenethyl, styryl, cyclopropyl, cyclobutyl, cyclopentyl, cyclohexyl, and 3-pyridyl.

In certain embodiments of a compound of Formula (I), $R^1$ is selected from hydrogen, —C(O)$R^{19}$, —C(O)O$R^{20}$, and

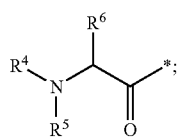

$R^2$ is selected from hydrogen, —C(O)$R^{19}$, —C(O)O$R^{20}$, and

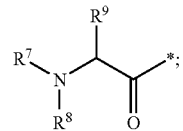

wherein each of $R^4$ and $R^5$ is hydrogen; $R^6$ is selected from hydrogen, methyl, isopropyl, isobutyl, sec-butyl, tert-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl, and 3-indolylmethyl; or $R^5$ and $R^6$ together with the nitrogen atom to which they are bonded form an azetidine, pyrrolidine, or piperidine ring;

each of $R^7$ and $R^8$ is hydrogen; $R^9$ is selected from hydrogen, methyl, isopropyl, isobutyl, sec-butyl, tert-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$N HC(NH)NH$_2$, phenyl, benzyl, 4-hydroxybenzyl, 4-imidazolylmethyl, and 3-indolylmethyl; or $R^8$ and $R^9$ together with the nitrogen atom to which they are bonded form an azetidine, pyrrolidine, or piperidine ring; and each of $R^{19}$ and $R^{20}$ is independently $C_{1-6}$ alkyl.

In certain of the aforementioned embodiments, each of $R^1$ and $R^2$ is hydrogen;

$R^{12}$ is an acyloxyalkylcarbonyl group having the formula:

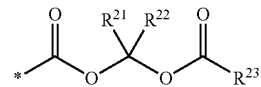

wherein $R^{21}$ is selected from hydrogen, methyl, ethyl, propyl, isopropyl, butyl, isobutyl, sec-butyl, tert-butyl, cyclopentyl, cyclohexyl, phenyl, benzyl, phenethyl, and 3-pyridyl, $R^{22}$ is hydrogen, and $R^{23}$ is selected from methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, 1,1-dimethoxyethyl, 1,1-diethoxyethyl, phenyl, 2-methylphenyl, 2,6-dimethylphenyl, 2-methoxyphenyl, 4-methoxyphenyl, 2,6-dimethoxyphenyl, benzyl, phenethyl, styryl, cyclopropyl, cyclobutyl, cyclopentyl, cyclohexyl, and 3-pyridyl.

In certain of the aforementioned embodiments, $R^{21}$ is selected from hydrogen, methyl, propyl, isopropyl, and tert-butyl; $R^{22}$ is hydrogen; and $R^{23}$ is selected from methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, 1,1-dimethoxyethyl, 1,1-diethoxyethyl, phenyl, 2-methylphenyl, 2,6-dimethylphenyl, 2-methoxyphenyl, 4-methoxyphenyl, 2,6-dimethoxyphenyl, benzyl, phenethyl, styryl, cyclopropyl, cyclobutyl, cyclopentyl, cyclohexyl, and 3-pyridyl.

In certain of the aforementioned embodiments, $R^{21}$ is methyl; $R^{22}$ is hydrogen; and $R^{23}$ is selected from methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, 1,1-dimethoxyethyl, 1,1-diethoxyethyl, phenyl, 2-methylphenyl, 2,6-dimethylphenyl, 2-methoxyphenyl, 4-methoxyphenyl, 2,6-dimethoxyphenyl, benzyl, phenethyl, styryl, cyclopropyl, cyclobutyl, cyclopentyl, cyclohexyl, and 3-pyridyl.

In certain embodiments of compounds of Formula (I), $R^1$ is

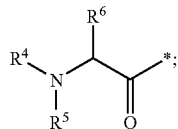

$R^2$ is hydrogen; each of $R^4$ and $R^5$ is hydrogen; $R^6$ is selected from methyl, isopropyl, isobutyl, sec-butyl, tert-butyl, and benzyl; $R^3$ is —$NHR^{12}$, wherein $R^{12}$ is an acyloxyalkylcarbonyl group having the formula:

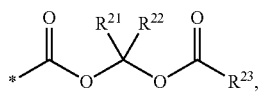

wherein $R^{21}$ is selected from hydrogen, methyl, ethyl, propyl, isopropyl, butyl, isobutyl, sec-butyl, tert-butyl, cyclopentyl, cyclohexyl, phenyl, benzyl, phenethyl, and 3-pyridyl; $R^{22}$ is hydrogen; and $R^{23}$ is selected from methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, 1,1-dimethoxyethyl, 1,1-diethoxyethyl, phenyl, 2-methylphenyl, 2,6-dimethylphenyl, 2-methoxyphenyl, 4-methoxyphenyl, 2,6-dimethoxyphenyl, benzyl, phenethyl, styryl, cyclopropyl, cyclobutyl, cyclopentyl, cyclohexyl, and 3-pyridyl.

In certain of the aforementioned embodiments, $R^{21}$ is selected from hydrogen, methyl, propyl, isopropyl, and tert-butyl, $R^{22}$ is hydrogen, and $R^{23}$ is selected from methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, 1,1-dimethoxyethyl, 1,1-diethoxyethyl, phenyl, 2-methylphenyl, 2,6-dimethylphenyl, 2-methoxyphenyl, 4-methoxyphenyl, 2,6-dimethoxyphenyl, benzyl, phenethyl, styryl, cyclopropyl, cyclobutyl, cyclopentyl, cyclohexyl, and 3-pyridyl.

In certain of the aforementioned embodiments, $R^{21}$ is methyl, $R^{22}$ is hydrogen, and $R^{23}$ is selected from methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, 1,1-dimethoxyethyl, 1,1-diethoxyethyl, phenyl, 2-methylphenyl, 2,6-dimethylphenyl, 2-methoxyphenyl, 4-methoxyphenyl, 2,6-dimethoxyphenyl, benzyl, phenethyl, styryl, cyclopropyl, cyclobutyl, cyclopentyl, cyclohexyl, and 3-pyridyl.

In certain of the aforementioned embodiments, $R^6$ is isopropyl, and in certain embodiments wherein $R^6$ is isopropyl, the stereochemistry of the carbon to which $R^6$ is bonded is of the S-configuration.

In certain embodiments of compounds of Formula (I), $R^1$ is hydrogen;

$R^2$ is

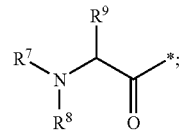

each of $R^7$ and $R^8$ is hydrogen; $R^9$ is selected from methyl, isopropyl, isobutyl, secbutyl, tert-butyl, and benzyl; $R^3$ is —$NHR^{12}$, wherein $R^{12}$ is an acyloxyalkylcarbonyl group having the formula:

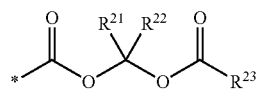

wherein $R^{21}$ is selected from hydrogen, methyl, ethyl, propyl, isopropyl, butyl, isobutyl, sec-butyl, tert-butyl, cyclopentyl, cyclohexyl, phenyl, benzyl, phenethyl, and 3-pyridyl; $R^{22}$ is hydrogen; and $R^{23}$ is selected from methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, 1,1-dimethoxyethyl, 1,1-diethoxyethyl, phenyl, 2-methylphenyl, 2,6-dimethylphenyl, 2-methoxyphenyl, 4-methoxyphenyl, 2,6-dimethoxyphenyl, benzyl, phenethyl, styryl, cyclopropyl, cyclobutyl, cyclopentyl, cyclohexyl, and 3-pyridyl.

In certain of the aforementioned embodiments, $R^{21}$ is selected from hydrogen, methyl, propyl, isopropyl, and tert-butyl; $R^{22}$ is hydrogen; and $R^{23}$ is selected from methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, 1,1-dimethoxyethyl, 1,1-diethoxyethyl, phenyl, 2-methylphenyl, 2,6-dimethylphenyl, 2-methoxyphenyl, 4-methoxyphenyl, 2,6-dimethoxyphenyl, benzyl, phenethyl, styryl, cyclopropyl, cyclobutyl, cyclopentyl, cyclohexyl, and 3-pyridyl.

In certain of the aforementioned embodiments, $R^{21}$ is methyl; $R^{22}$ is hydrogen; and $R^{23}$ is selected from methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, 1,1-dimethoxyethyl, 1,1-diethoxyethyl, phenyl, 2-methylphenyl, 2,6-dimethylphenyl, 2-methoxyphenyl, 4-methoxyphenyl, 2,6-dimethoxyphenyl, benzyl, phenethyl, styryl, cyclopropyl, cyclobutyl, cyclopentyl, cyclohexyl, and 3-pyridyl In certain of the aforementioned embodiments, $R^9$ is isopropyl, and in certain embodiments wherein $R^9$ is isopropyl, the stereochemistry of the carbon to which $R^9$ is bonded is of the S-configuration.

In certain embodiments of compounds of Formula (I), $R^1$ is selected from hydrogen, acyl, substituted acyl, acyloxyalky lcarbonyl, substituted acyloxyalkylcarbonyl, oxycarbonyl, substituted oxycarbonyl, and

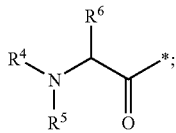

$R^2$ is selected from hydrogen, acyl, substituted acyl, acyloxyalkylcarbonyl, substituted acyloxyalkylcarbonyl, oxycarbonyl, substituted oxycarbonyl, and

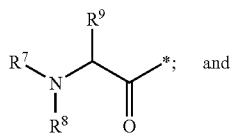

$R^3$ is —$NHR^2$, wherein $R^{12}$ is a moiety of structural Formula (II):

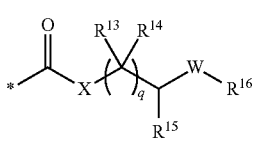

wherein
X is selected from O and $CH_2$;
q is selected from 1 and 2;
each $R^{13}$ and $R^{14}$ is independently selected from hydrogen, $C_{1-4}$ alkyl, phenyl, and substituted phenyl; or $R^{13}$ and $R^{14}$ together with the carbon atom to which they are both bonded form a $C_{3-7}$ cycloalkyl ring;
$R^{15}$ is selected from hydrogen, $C_{1-4}$ alkyl, and $CO_2R^{17}$;
W is selected from O and $NR^{18}$;
$R^{17}$ is selected from hydrogen, $C_{1-4}$ alkyl, phenyl, and substituted phenyl;
$R^{18}$ is selected from hydrogen and $C_{1-4}$ alkyl;
$R^{16}$ is selected from $C_{1-4}$ alkyl, —$C(O)R^{19}$, —$C(O)OR^{20}$,

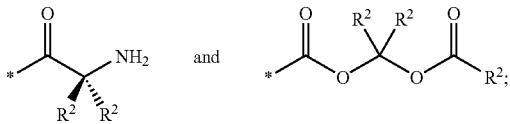

wherein $R^{19}$ is selected from hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, and substituted heteroarylalkyl;
$R^{20}$ is selected from $C_{1-6}$ alkyl, $C_{3-7}$ cycloalkyl, aryl, substituted aryl, arylalkyl, substituted arylalkyl, heteroaryl, and substituted heteroaryl;
$R^{21}$ and $R^{22}$ are independently selected from hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, cycloalkoxycarbonyl, substituted cycloalkoxycarbonyl, heteroaryl, substituted heteroaryl, heteroarylalkyl, and substituted heteroarylalkyl, or $R^{21}$ and $R^{22}$ together with the carbon atom to which they are bonded form a cycloalkyl, substituted cycloalkyl, cycloheteroalkyl, or substituted cycloheteroalkyl ring;
$R^{23}$ is selected from acyl, substituted acyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, and substituted heteroarylalkyl;
$R^{24}$ is selected from hydrogen, alkyl, substituted alkyl, alkoxy, substituted alkoxy, acyl, substituted acyl, alkoxycarbonyl, substituted alkoxycarbonyl, aryl, substituted aryl, arylalkyl, substituted arylalkyl, carbamoyl, substituted carbamoyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, and substituted heteroarylalkyl; and
$R^{25}$ is selected from hydrogen and $C_{1-4}$ alkyl; or $R^{24}$ and $R^{25}$ together with the carbon to which they are bonded form a cycloalkyl or cycloheteroalkyl ring;
with the proviso that:
when X is $CH_2$ and W is O; then $R^{16}$ is not $C_{1-4}$ alkyl.
In certain of the aforementioned embodiments, $R^{21}$ is selected from hydrogen, methyl, ethyl, propyl, isopropyl, butyl, isobutyl, sec-butyl, tert-butyl, cyclopentyl, cyclohexyl, phenyl, benzyl, phenethyl, and 3-pyridyl; and $R^{22}$ is hydrogen. In certain of the aforementioned embodiments, $R^{23}$ is selected from methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, 1,1-dimethoxyethyl, 1,1-diethoxyethyl, phenyl, 2-methylphenyl, 2,6-dimethylphenyl, 2-methoxyphenyl, 4-methoxyphenyl, 2,6-dimethoxyphenyl, benzyl, phenethyl, styryl, cyclopropyl, cyclobutyl, cyclopentyl, cyclohexyl, and 3-pyridyl.
In certain of the aforementioned embodiments, $R^{21}$ is selected from hydrogen, methyl, propyl, isopropyl, and tert-butyl; $R^{22}$ is hydrogen; and $R^{23}$ is selected from methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, 1,1-dimethoxyethyl, 1,1-diethoxyethyl, phenyl, 2-methylphenyl, 2,6-dimethylphenyl, 2-methoxyphenyl, 4-methoxyphenyl, 2,6-dimethoxyphenyl, benzyl, phenethyl, styryl, cyclopropyl, cyclobutyl, cyclopentyl, cyclohexyl, and 3-pyridyl.
In certain of the aforementioned embodiments, $R^{21}$ is methyl; $R^{22}$ is hydrogen; and $R^{23}$ is selected from methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, 1,1-dimethoxyethyl, 1,1-diethoxyethyl, phenyl, 2-methylphenyl, 2,6-dimethylphenyl, 2-methoxyphenyl, 4-methoxyphenyl, 2,6-dimethoxyphenyl, benzyl, phenethyl, styryl, cyclopropyl, cyclobutyl, cyclopentyl, cyclohexyl, and 3-pyridyl.
In certain of the aforementioned embodiments, $R^{24}$ is selected from hydrogen, methyl, isopropyl, isobutyl, sec-butyl, tert-butyl, cyclopentyl, cyclohexyl, —$CH_2OH$, —$CH(OH)CH_3$, —$CH_2CO_2H$, —$CH_2CH_2CO_2H$, —$CH_2CONH_2$, —$CH_2CH_2CONH_2$, —$CH_2CH_2SCH_3$, —$CH_2SH$, —$CH_2(CH_2)_3NH_2$, —$CH_2CH_2CH_2NHC(NH)NH_2$, phenyl, benzyl, 4-hydroxybenzyl, 4-imidazolylmethyl, and 3-indolylmethyl; and $R^{25}$ is hydrogen.

In certain embodiments of a compound of Formula (I), $R^1$ is selected from hydrogen, —C(O)$R^{19}$, —C(O)O$R^{20}$, and

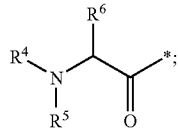

$R^2$ is selected from hydrogen, —C(O)$R^{19}$, —C(O)O$R^{20}$, and

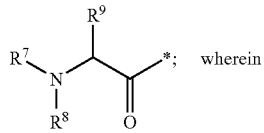 wherein each of $R^4$ and $R^5$ is hydrogen; $R^6$ is selected from hydrogen, methyl, isopropyl, isobutyl, sec-butyl, tert-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl, and 3-indolylmethyl; or $R^5$ and $R^6$ together with the nitrogen atom to which they are bonded form an azetidine, pyrrolidine, or piperidine ring;

each of $R^7$ and $R^8$ is hydrogen; $R^9$ is selected from hydrogen, methyl, isopropyl, isobutyl, sec-butyl, tert-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl, and 3-indolylmethyl; or $R^8$ and $R^9$ together with the nitrogen atom to which they are bonded form an azetidine, pyrrolidine, or piperidine ring; and each of $R^{19}$ and $R^{20}$ is independently $C_{1-6}$ alkyl.

In certain embodiments of a compound of Formula (I), $R^1$ is selected from hydrogen, acyl, substituted acyl, acyloxyalkylcarbonyl, substituted acyloxyalkylcarbonyl, oxycarbonyl, substituted oxycarbonyl, and

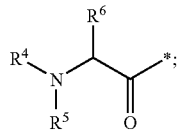

$R^2$ is selected from hydrogen, acyl, substituted acyl, acyloxyalkylcarbonyl, substituted acyloxyalkylcarbonyl, oxycarbonyl, substituted oxycarbonyl, and

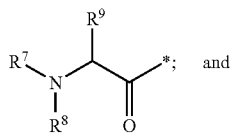 and $R^3$ is —NH$R^{12}$ and $R^{12}$ is a moiety of structural Formula (II); wherein X is O;

q is 1;

each of $R^{13}$ and $R^{14}$ is hydrogen;

$R^{15}$ is hydrogen;

W is N$R^{18}$, and $R^{18}$ is hydrogen; and $R^{16}$ is

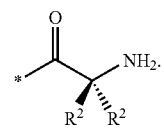

In certain of the aforementioned embodiments, $R^{24}$ is selected from hydrogen, methyl, isopropyl, isobutyl, sec-butyl, tert-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl, and 3-indolylmethyl; and $R^{25}$ is hydrogen.

In certain of the aforementioned embodiments wherein $R^{24}$ is selected from hydrogen, methyl, isopropyl, isobutyl, sec-butyl, tert-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl, and 3-indolylmethyl; and $R^{25}$ is hydrogen; and each of $R^1$ and $R^2$ is hydrogen.

In certain of the aforementioned embodiments wherein $R^{24}$ is selected from hydrogen, methyl, isopropyl, isobutyl, sec-butyl, tert-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl, and 3-indolylmethyl; and $R^{25}$ is hydrogen; $R^1$ is

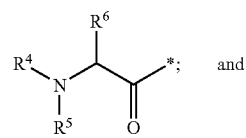 and $R^2$ is hydrogen.

In certain of the aforementioned embodiments wherein $R^{24}$ is selected from hydrogen, methyl, isopropyl, isobutyl, sec-butyl, tert-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)-

NH$_2$, phenyl, benzyl, 4-hydroxybenzyl, 4-imidazolylmethyl, and 3-indolylmethyl; R$^{25}$ is hydrogen; R$^1$ is

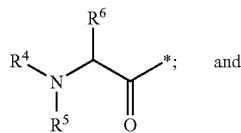

and

R$^2$ is hydrogen;
each of R$^4$ and R$^5$ is hydrogen; and R$^6$ is selected from hydrogen, methyl, isopropyl, isobutyl, sec-butyl, tert-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl, and 3-indolylmethyl; or R$^5$ and R$^6$ together with the nitrogen atom to which they are bonded form an azetidine, pyrrolidine, or piperidine ring.

In certain of the aforementioned embodiments wherein R$^{24}$ is selected from hydrogen, methyl, isopropyl, isobutyl, sec-butyl, tert-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl, and 3-indolylmethyl; R$^{25}$ is hydrogen; R$^1$ is

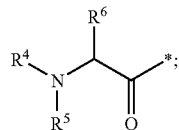

R$^2$ is hydrogen; each of R$^4$ and R$^5$ is hydrogen; and R$^6$ is selected from methyl, isopropyl, isobutyl, sec-butyl, tert-butyl, and benzyl; in certain embodiments R$^6$ is isopropyl; and in certain embodiments wherein R$^6$ is isopropyl, the stereochemistry of the carbon to which R$^6$ is bonded is of the S-configuration.

In certain of the aforementioned embodiments, R$^{24}$ is selected from hydrogen, methyl, isopropyl, isobutyl, sec-butyl, tert-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl, and 3-indolylmethyl; and R$^{25}$ is hydrogen; R$^1$ is hydrogen; and R$^2$ is

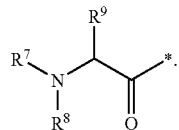

In certain of the aforementioned embodiments, R$^{24}$ is selected from hydrogen, methyl, isopropyl, isobutyl, sec-butyl, tert-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl, and 3-indolylmethyl; and R$^{25}$ is hydrogen; and R$^1$ is hydrogen; R$^2$ is

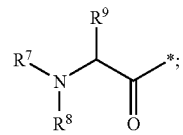

each of R$^7$ and R$^8$ is hydrogen; and R$^9$ is selected from hydrogen, methyl, isopropyl, isobutyl, sec-butyl, tert-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl, and 3-indolylmethyl; or R$^8$ and R$^9$ together with the nitrogen atom to which they are bonded form an azetidine, pyrrolidine, or piperidine ring.

In certain of the aforementioned embodiments, R$^{24}$ is selected from hydrogen, methyl, isopropyl, isobutyl, sec-butyl, tert-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl, and 3-indolylmethyl; and R$^{25}$ is hydrogen; R$^1$ is hydrogen; R$^2$ is

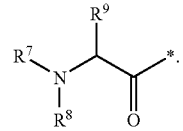

each of R$^7$ and R$^8$ is hydrogen; and R$^9$ is selected from methyl, isopropyl, isobutyl, sec-butyl, tert-butyl, and benzyl; in certain embodiments R$^9$ is isopropyl; and in certain embodiments wherein R$^9$ is isopropyl the stereochemistry of the carbon to which R$^9$ is bonded is of the S-configuration.

In certain embodiments of compounds of Formula (I), R$^1$ is selected from hydrogen, acyl, substituted acyl, acyloxyalkylcarbonyl, substituted acyloxyalkylcarbonyl, oxycarbonyl, substituted oxycarbonyl, and

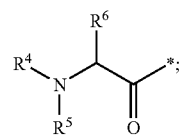

$R^2$ is selected from hydrogen, acyl, substituted acyl, acyloxyalkylcarbonyl, substituted acyloxyalkylcarbonyl, oxycarbonyl, substituted oxycarbonyl, and

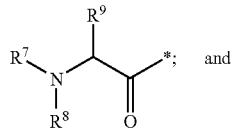

$R^3$ is —$NHR^{12}$, and $R^{12}$ is a moiety of structural Formula (II); wherein X is O;

q is 1;

each of $R^{13}$ and $R^{14}$ is hydrogen;

$R^{15}$ is —$CO_2H$;

W is $NR^{18}$, and $R^{18}$ is hydrogen; and $R^{16}$ is

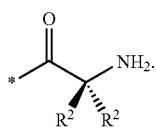

In certain of the aforementioned embodiments, each of $R^1$ and $R^2$ is hydrogen.

In certain of the aforementioned embodiments, $R^1$ is hydrogen; $R^2$ is hydrogen: $R^{24}$ is selected from hydrogen, methyl, isopropyl, isobutyl, sec-butyl, tert-butyl, cyclopentyl, cyclohexyl, —$CH_2OH$, —$CH(OH)CH_3$, —$CH_2CO_2H$, —$CH_2CH_2CO_2H$, —$CH_2CONH_2$, —$CH_2CH_2CONH_2$, —$CH_2CH_2SCH_3$, —$CH_2SH$, —$CH_2(CH_2)_3NH_2$, —$CH_2CH_2CH_2NHC(NH)NH_2$, phenyl, benzyl, 4-hydroxybenzyl, 4-imidazolylmethyl, and 3-indolylmethyl; and $R^{25}$ is hydrogen.

In certain embodiments of compounds of Formula (I), $R^1$ is selected from hydrogen, acyl, substituted acyl, acyloxyalkylcarbonyl, substituted acyloxyalkylcarbonyl, oxycarbonyl, substituted oxycarbonyl, and

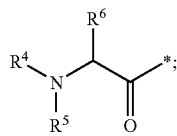

$R^2$ is selected from hydrogen, acyl, substituted acyl, acyloxyalkylcarbonyl, substituted acyloxyalkylcarbonyl, oxycarbonyl, substituted oxycarbonyl, and

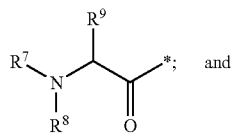

$R^3$ is —$NHR^{12}$, and $R^{12}$ is a moiety of structural Formula (II); wherein X is O;

q is 1;

each of $R^{13}$ and $R^{14}$ is hydrogen;

$R^{15}$ is hydrogen;

W is $NR^{18}$, and $R^{18}$ is methyl; and $R^{16}$ is methyl.

In certain of the aforementioned embodiments, each of $R^1$ and $R^2$ is hydrogen.

In certain of the aforementioned embodiments, $R^1$ is

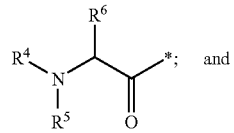

$R^2$ is hydrogen.

In certain of the aforementioned embodiments wherein $R^1$ is

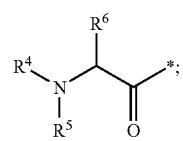

and $R^2$ is hydrogen; each of $R^4$ and $R^5$ is hydrogen; and $R^6$ is selected from hydrogen, methyl, isopropyl, isobutyl, sec-butyl, tert-butyl, cyclopentyl, cyclohexyl, —$CH_2OH$, —$CH(OH)CH_3$, —$CH_2CO_2H$, —$CH_2CH_2CO_2H$, —$CH_2CONH_2$, —$CH_2CH_2CONH_2$, —$CH_2CH_2SCH_3$, —$CH_2SH$, —$CH_2(CH_2)_3NH_2$, —$CH_2CH_2CH_2NHC(NH)NH_2$, phenyl, benzyl, 4-hydroxybenzyl, 4-imidazolylmethyl, and 3-indolylmethyl; or $R^5$ and $R^6$ together with the nitrogen atom to which they are bonded form an azetidine, pyrrolidine, or piperidine ring.

In certain of the aforementioned embodiments wherein each of $R^1$ is

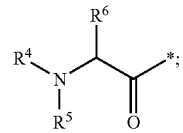

and $R^2$ is hydrogen; each of $R^4$ and $R^5$ is hydrogen; $R^6$ is selected from methyl, isopropyl, isobutyl, sec-butyl, tert-butyl, and benzyl; in certain embodiments $R^6$ is isopropyl; and in certain embodiments wherein $R^6$ is isopropyl the stereochemistry of the carbon to which $R^6$ is bonded is of the S-configuration.

In certain embodiments of compounds of Formula (I), $R^1$ is hydrogen; $R^2$ is

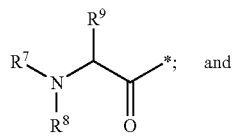

$R^3$ is —NHR$^{12}$, and R$^{12}$ is a moiety of structural Formula (II); wherein
X is O;
q is 1;
each of R$^{13}$ and R$^{14}$ is hydrogen;
R$^{15}$ is hydrogen;
W is NR$^{18}$, and R$^{18}$ is methyl; and
R$^{16}$ is methyl.

In certain of the aforementioned embodiments, each of R$^7$ and R$^8$ is hydrogen; and R$^9$ is selected from hydrogen, methyl, isopropyl, isobutyl, sec-butyl, tert-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl, and 3-indolylmethyl; or R$^8$ and R$^9$ together with the nitrogen atom to which they are bonded form an azetidine, pyrrolidine, or piperidine ring.

In certain of the aforementioned embodiments, each of R$^7$ and R$^8$ is hydrogen; R$^9$ is selected from methyl, isopropyl, isobutyl, sec-butyl, tert-butyl, and benzyl; in certain embodiments R$^9$ is isopropyl; and in certain embodiments wherein R$^9$ is isopropyl the stereochemistry of the carbon to which R$^9$ is bonded is of the S-configuration.

In certain embodiments of compounds of Formula (I), R$^1$ is selected from hydrogen, acyl, substituted acyl, acyloxyalkylcarbonyl, substituted acyloxyalkylcarbonyl, oxycarbonyl, substituted oxycarbonyl, and

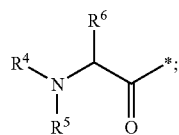

R$^2$ is selected from hydrogen, acyl, substituted acyl, acyloxyalkylcarbonyl, substituted acyloxyalkylcarbonyl, oxycarbonyl, substituted oxycarbonyl, and

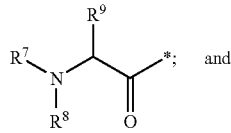

$R^3$ is —NHR$^{12}$, wherein R$^{12}$ is a moiety of structural Formula (II); wherein
X is O;
q is 1;
each of R$^{13}$ and R$^{14}$ is hydrogen;
R$^{15}$ is hydrogen;
W is O; and
R$^{16}$ is —C(O)R$^{19}$.

In certain of the aforementioned embodiments, R$^{19}$ is selected from C$_{1-6}$ alkyl, substituted C$_{1-6}$ alkyl, C$_{3-6}$ cycloalkyl, phenyl, substituted phenyl, C$_{7-9}$ phenylalkyl, pyridyl, and substituted pyridyl.

In certain of the aforementioned embodiments, R$^{19}$ is selected from methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, phenyl, 2-methylphenyl, 2,6-dimethylphenyl, 2-methoxyphenyl, 4-methoxyphenyl, 2,6-dimethoxyphenyl, benzyl, phenethyl, styryl, cyclopropyl, cyclobutyl, cyclopentyl, cyclohexyl, and 3-pyridyl.

In certain of the aforementioned embodiments wherein R$^{19}$ is selected from methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, phenyl, 2-methylphenyl, 2,6-dimethylphenyl, 2-methoxyphenyl, 4-methoxyphenyl, 2,6-dimethoxyphenyl, benzyl, phenethyl, styryl, cyclopropyl, cyclobutyl, cyclopentyl, cyclohexyl, and 3-pyridyl; and each of R$^1$ and R$^2$ is hydrogen.

In certain of the aforementioned embodiments wherein R$^{19}$ is selected from methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, phenyl, 2-methylphenyl, 2,6-dimethylphenyl, 2-methoxyphenyl, 4-methoxyphenyl, 2,6-dimethoxyphenyl, benzyl, phenethyl, styryl, cyclopropyl, cyclobutyl, cyclopentyl, cyclohexyl, and 3-pyridyl; R$^1$ is

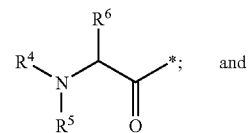

R$^2$ is hydrogen.

In certain of the aforementioned embodiments wherein R$^{19}$ is selected from methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, phenyl, 2-methylphenyl, 2,6-dimethylphenyl, 2-methoxyphenyl, 4-methoxyphenyl, 2,6-dimethoxyphenyl, benzyl, phenethyl, styryl, cyclopropyl, cyclobutyl, cyclopentyl, cyclohexyl, and 3-pyridyl; R$^1$ is

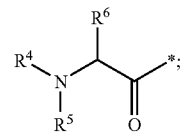

R$^2$ is hydrogen;
each of R$^4$ and R$^5$ is hydrogen; and R$^6$ is selected from hydrogen, methyl, isopropyl, isobutyl, sec-butyl, tert-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl, and 3-indolylmethyl; or R$^5$ and R$^6$ together with the nitrogen atom to which they are bonded form an azetidine, pyrrolidine, or piperidine ring.

In certain of the aforementioned embodiments wherein R$^{19}$ is selected from methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, phenyl, 2-methylphenyl, 2,6-dimethylphenyl, 2-methoxyphenyl, 4-methoxyphenyl, 2,6-dimethoxyphenyl, benzyl, phenethyl, styryl, cyclopropyl, cyclobutyl, cyclopentyl, cyclohexyl, and 3-pyridyl; $R^1$ is

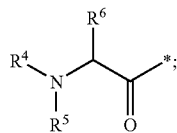

$R^2$ is hydrogen;
each of $R^4$ and $R^5$ is hydrogen; and $R^6$ is selected from methyl, isopropyl, isobutyl, sec-butyl, tert-butyl, and benzyl; in certain embodiments $R^6$ is isopropyl, and in certain embodiments wherein $R^6$ is isopropyl the stereochemistry of the carbon to which $R^6$ is bonded is of the S-configuration.

In certain of the aforementioned embodiments wherein $R^{19}$ is selected from methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, phenyl, 2-methylphenyl, 2,6-dimethylphenyl, 2-methoxyphenyl, 4-methoxyphenyl, 2,6-dimethoxyphenyl, benzyl, phenethyl, styryl, cyclopropyl, cyclobutyl, cyclopentyl, cyclohexyl, and 3-pyridyl; $R^1$ is hydrogen; and $R^2$ is

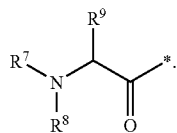

In certain of the aforementioned embodiments wherein $R^{19}$ is selected from methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, phenyl, 2-methylphenyl, 2,6-dimethylphenyl, 2-methoxyphenyl, 4-methoxyphenyl, 2,6-dimethoxyphenyl, benzyl, phenethyl, styryl, cyclopropyl, cyclobutyl, cyclopentyl, cyclohexyl, and 3-pyridyl;
$R^1$ is hydrogen; and
$R^2$ is

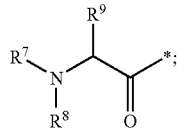

each of $R^7$ and $R^8$ is hydrogen; and $R^9$ is selected from hydrogen, methyl, isopropyl, isobutyl, sec-butyl, tert-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl, and 3-indolylmethyl; or $R^8$ and $R^9$ together with the nitrogen atom to which they are bonded form an azetidine, pyrrolidine, or piperidine ring.

In certain of the aforementioned embodiments wherein $R^{19}$ is selected from methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, phenyl, 2-methylphenyl, 2,6-dimethylphenyl, 2-methoxyphenyl, 4-methoxyphenyl, 2,6-dimethoxyphenyl, benzyl, phenethyl, styryl, cyclopropyl, cyclobutyl, cyclopentyl, cyclohexyl, and 3-pyridyl;
$R^1$ is hydrogen; and
$R^2$ is

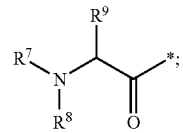

each of $R^7$ and $R^8$ is hydrogen; $R^9$ is selected from methyl, isopropyl, isobutyl, sec-butyl, tert-butyl, and benzyl; in certain embodiments $R^9$ is isopropyl; and in certain embodiments wherein $R^9$ is isopropyl the stereochemistry of the carbon to which $R^9$ is bonded is of the S-configuration.

In certain embodiments of compounds of Formula (I), $R^1$ is selected from hydrogen, acyl, substituted acyl, acyloxyalkylcarbonyl, substituted acyloxyalkylcarbonyl, oxycarbonyl, substituted oxycarbonyl, and

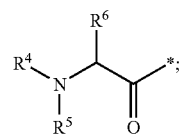

$R^2$ is selected from hydrogen, acyl, substituted acyl, acyloxyalkylcarbonyl, substituted acyloxyalkylcarbonyl, oxycarbonyl, substituted oxycarbonyl, and

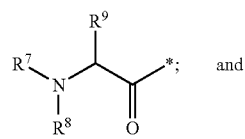

$R^3$ is —NHR$^{12}$, and R$^{12}$ is a moiety of structural Formula (II); wherein
X is O;
q is 1;
each of $R^{13}$ and $R^{14}$ is hydrogen;
$R^{15}$ is hydrogen;
W is O; and
$R^{16}$ is —C(O)OR$^{20}$.

In certain of the aforementioned embodiments, $R^{20}$ is selected from $C_{1-6}$ alkanyl, $C_{2-6}$ alk-1-en-2-yl, 2-$C_{3-7}$ cycloalkyl-eth-1-en-2-yl, 2-phenyleth-1-en-2-yl, substituted 2-phenyleth-1-en-2-yl, $C_{3-7}$ cycloalkanyl, $C_{5-7}$ cycloalk-1-en-1-yl, phenyl, naphthyl, halophenyl, methoxyphenyl, cyanophenyl, carboxyphenyl, $C_{1-4}$ alkoxycarbonylphenyl, aminophenyl, halobenzyl, methoxybenzyl, cyanobenzyl, carboxybenzyl, $C_{1-4}$ alkoxycarbonylbenzyl, aminobenzyl, furyl, thienyl, pyrrolyl, imidazoyl, oxazolyl, pyridyl, pyrimidyl, pyrazinyl, and triazinyl.

In certain of the aforementioned embodiments, $R^{20}$ is selected from methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, hex-1-yl, hex-2-yl, hex-3-yl, 2-methylpent-1-yl, 3-methylpent-1-yl, vinyl, propen-2-yl, buten-2-yl, phenethen-2-yl, cyclopentyl, cyclohexyl, cyclopenten-1-yl, cyclohexen-1-yl, phenyl, 4-methoxyphenyl, benzyl, and 4-methoxybenzyl.

In certain of the aforementioned embodiments, $R^{20}$ is selected from methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, hex-1-yl, hex-2-yl, hex-3-yl, 2-methylpent-1-yl, 3-methylpent-1-yl, vinyl, propen-2-yl, buten-2-yl, phenethen-2-yl, cyclopentyl, cyclohexyl, cyclopenten-1-yl, cyclohexen-1-yl, phenyl, 4-methoxyphenyl, benzyl, and 4-methoxybenzyl; and each of $R^1$ and $R^2$ is hydrogen.

In certain of the aforementioned embodiments, $R^{20}$ is selected from methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, hex-1-yl, hex-2-yl, hex-3-yl, 2-methylpent-1-yl, 3-methylpent-1-yl, vinyl, propen-2-yl, buten-2-yl, phenethen-2-yl, cyclopentyl, cyclohexyl, cyclopenten-1-yl, cyclohexen-1-yl, phenyl, 4-methoxyphenyl, benzyl, and 4-methoxybenzyl; $R^1$ is

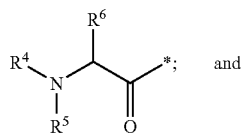

$R^2$ is hydrogen.

In certain of the aforementioned embodiments, $R^{20}$ is selected from methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, hex-1-yl, hex-2-yl, hex-3-yl, 2-methylpent-1-yl, 3-methylpent-1-yl, vinyl, propen-2-yl, buten-2-yl, phenethen-2-yl, cyclopentyl, cyclohexyl, cyclopenten-1-yl, cyclohexen-1-yl, phenyl, 4-methoxyphenyl, benzyl, and 4-methoxybenzyl; $R^1$ is

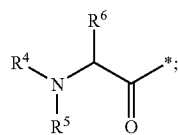

$R^2$ is hydrogen;

each of $R^4$ and $R^5$ is hydrogen; and $R^6$ is selected from hydrogen, methyl, isopropyl, isobutyl, sec-butyl, tert-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$N HC(NH)NH$_2$, phenyl, benzyl, 4-hydroxybenzyl, 4-imidazolylmethyl, and 3-indolylmethyl; or $R^5$ and $R^6$ together with the nitrogen atom to which they are bonded form an azetidine, pyrrolidine, or piperidine ring.

In certain of the aforementioned embodiments, $R^{20}$ is selected from methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, hex-1-yl, hex-2-yl, hex-3-yl, 2-methylpent-1-yl, 3-methylpent-1-yl, vinyl, propen-2-yl, buten-2-yl, phenethen-2-yl, cyclopentyl, cyclohexyl, cyclopenten-1-yl, cyclohexen-1-yl, phenyl, 4-methoxyphenyl, benzyl, and 4-methoxybenzyl; $R^1$ is

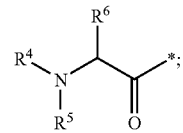

$R^2$ is hydrogen;

each of $R^4$ and $R^5$ is hydrogen; $R^6$ is selected from methyl, isopropyl, isobutyl, sec-butyl, tert-butyl, and benzyl; in certain embodiments $R^6$ is isopropyl; and in certain embodiments wherein $R^6$ is isopropyl the stereochemistry of the carbon to which $R^6$ is bonded is of the S-configuration.

In certain of the aforementioned embodiments, $R^{20}$ is selected from methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, hex-1-yl, hex-2-yl, hex-3-yl, 2-methylpent-1-yl, 3-methylpent-1-yl, vinyl, propen-2-yl, buten-2-yl, phenethen-2-yl, cyclopentyl, cyclohexyl, cyclopenten-1-yl, cyclohexen-1-yl, phenyl, 4-methoxyphenyl, benzyl, and 4-methoxybenzyl; $R^1$ is hydrogen; and $R^2$ is

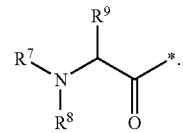

In certain of the aforementioned embodiments, $R^{20}$ is selected from methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, hex-1-yl, hex-2-yl, hex-3-yl, 2-methylpent-1-yl, 3-methylpent-1-yl, vinyl, propen-2-yl, buten-2-yl, phenethen-2-yl, cyclopentyl, cyclohexyl, cyclopenten-1-yl, cyclohexen-1-yl, phenyl, 4-methoxyphenyl, benzyl, and 4-methoxybenzyl; $R^1$ is hydrogen;

$R^2$ is

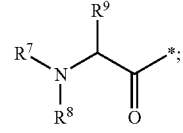

each of $R^7$ and $R^8$ is hydrogen; and $R^9$ is selected from hydrogen, methyl, isopropyl, isobutyl, sec-butyl, tert-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$N HC(NH)NH$_2$, phenyl, benzyl, 4-hydroxybenzyl, 4-imidazolylmethyl, and 3-indolylmethyl; or $R^8$ and $R^9$ together with the nitrogen atom to which they are bonded form an azetidine, pyrrolidine, or piperidine ring.

In certain of the aforementioned embodiments, $R^{20}$ is selected from methyl, ethyl, propyl, isopropyl, butyl, isobutyl, sec-butyl, tert-butyl, pent-1-yl, pent-2-yl, pent-3- yl, 2-methylbut-1-yl, 3-methylbut-1-yl, hex-1-yl, hex-2-yl, hex-3-yl, 2-methylpent-1-yl, 3-methylpent-1-yl, vinyl, propen-2-yl, buten-2-yl, phenethen-2-yl, cyclopentyl, cyclohexyl, cyclopenten-1-yl, cyclohexen-1-yl, phenyl, 4-methoxyphenyl, benzyl, and 4-methoxybenzyl; $R^1$ is hydrogen; $R^2$ is

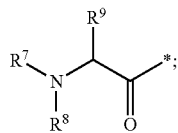

each of $R^7$ and $R^8$ is hydrogen; and $R^9$ is selected from methyl, isopropyl, isobutyl, sec-butyl, tert-butyl, and benzyl; in certain embodiments, $R^9$ is isopropyl; and in certain embodiments wherein $R^9$ is isopropyl the stereochemistry of the carbon to which $R^9$ is-bonded is of the S-configuration.

In certain embodiments of compounds of Formula (I), $R^1$ is selected from hydrogen, acyl, substituted acyl, acyloxyalkylcarbonyl, substituted acyloxyalkylcarbonyl, oxycarbonyl, substituted oxycarbonyl, and

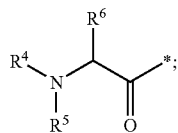

$R^2$ is selected from hydrogen, acyl, substituted acyl, acyloxyalkylcarbonyl, substituted acyloxyalkylcarbonyl, oxycarbonyl, substituted oxycarbonyl, and

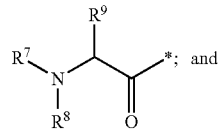

$R^3$ is —$NHR^{12}$, wherein $R^{12}$ is a moiety of structural Formula (II); wherein
X is O;
q is 1;
each of $R^{13}$ and $R^{14}$ is hydrogen;
$R^{15}$ is hydrogen;
W is $NR^{18}$, and $R^{18}$ is hydrogen; and
$R^{16}$ is —$C(O)OR^{20}$.

In certain of the aforementioned embodiments, $R^{20}$ is selected from $C_{16}$ alkanyl, $C_{2-6}$ alk-1-en-2-yl, 2-$C_{3-7}$ cycloalkyl-eth-1-en-2-yl, 2-phenyleth-1-en-2-yl, substituted 2-phenyleth-1-en-2-yl, $C_{3-7}$ cycloalkanyl, $C_{5-7}$ cycloalk-1-en-1-yl, phenyl, naphthyl, halophenyl, methoxyphenyl, cyanophenyl, carboxyphenyl, $C_{1-4}$ alkoxycarbonylphenyl, aminophenyl, halobenzyl, methoxybenzyl, cyanobenzyl, carboxybenzyl, $C_{1-4}$ alkoxycarbonylbenzyl, aminobenzyl, furyl, thienyl, pyrrolyl, imidazoyl, oxazolyl, pyridyl, pyrimidyl, pyrazinyl, and triazinyl.

In certain of the aforementioned embodiments, $R^{20}$ is selected from methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, hex-1-yl, hex-2-yl, hex-3-yl, 2-methylpent-1-yl, 3-methylpent-1-yl, vinyl, propen-2-yl, buten-2-yl, phenethen-2-yl, cyclopentyl, cyclohexyl, cyclopenten-1-yl, cyclohexen-1-yl, phenyl, 4-methoxyphenyl, benzyl, and 4-methoxybenzyl.

In certain of the aforementioned embodiments, $R^{20}$ is selected from methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, hex-1-yl, hex-2-yl, hex-3-yl, 2-methylpent-1-yl, 3-methylpent-1-yl, vinyl, propen-2-yl, buten-2-yl, phenethen-2-yl, cyclopentyl, cyclohexyl, cyclopenten-1-yl, cyclohexen-1-yl, phenyl, 4-methoxyphenyl, benzyl, and 4-methoxybenzyl; and each of $R^1$ and $R^2$ is hydrogen.

In certain embodiments of compounds of Formula (I), $R^1$ is

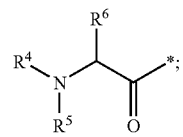

$R^2$ is hydrogen;
$R^3$ is —$NHR^{12}$, wherein $R^{12}$ is a moiety of structural Formula (II); wherein
X is O;
q is 1;
each of $R^{13}$ and $R^{14}$ is hydrogen;
$R^{15}$ is hydrogen;
W is $NR^{18}$, and $R^{18}$ is hydrogen; and
$R^{16}$ is —$C(O)OR^{20}$ wherein
$R^{20}$ is selected from methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, hex-1-yl, hex-2-yl, hex-3-yl, 2-methylpent-1-yl, 3-methylpent-1-yl, vinyl, propen-2-yl, buten-2-yl, phenethen-2-yl, cyclopentyl, cyclohexyl, cyclopenten-1-yl, cyclohexen-1-yl, phenyl, 4-methoxyphenyl, benzyl, and 4-methoxybenzyl.

In certain of the aforementioned embodiments, $R^{20}$ is selected from methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, hex-1-yl, hex-2-yl, hex-3-yl, 2-methylpent-1-yl, 3-methylpent-1-yl, vinyl, propen-2-yl, buten-2-yl, phenethen-2-yl, cyclopentyl, cyclohexyl, cyclopenten-1-yl, cyclohexen-1-yl, phenyl, 4-methoxyphenyl, benzyl, and 4-methoxybenzyl; $R^1$ is

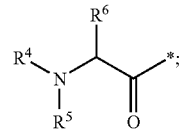

$R^2$ is hydrogen; each of $R^4$ and $R^5$ is hydrogen; and $R^6$ is selected from hydrogen, methyl, isopropyl, isobutyl, sec-butyl, tert-butyl, cyclopentyl, cyclohexyl, —$CH_2OH$, —$CH(OH)CH_3$, —$CH_2CO_2H$, —$CH_2CH_2CO_2H$, —$CH_2CONH_2$, —$CH_2CH_2CONH_2$, —$CH_2CH_2SCH_3$, —$CH_2SH$, —$CH_2(CH_2)_3NH_2$, —$CH_2CH_2CH_2NHC(NH)NH_2$, phenyl, benzyl, 4-hydroxybenzyl, 4-imidazolylmethyl, and 3-indolylmethyl; or $R^5$ and $R^6$ together with the nitrogen atom to which they are bonded form an azetidine, pyrrolidine, or piperidine ring.

In certain of the aforementioned embodiments, $R^{20}$ is selected from methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, hex-1-yl, hex-2-yl, hex-3-yl, 2-methylpent-1-yl, 3-methylpent-1-yl, vinyl, propen-2-yl, buten-2-yl, phenethen-2-yl, cyclopentyl, cyclohexyl, cyclopenten-1-yl, cyclohexen-1-yl, phenyl, 4-methoxyphenyl, benzyl, and 4-methoxybenzyl; $R^1$ is

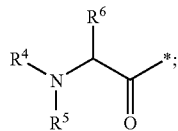

$R^2$ is hydrogen; each of $R^4$ and $R^5$ is hydrogen; $R^6$ is selected from methyl, isopropyl, isobutyl, sec-butyl, tert-butyl, and benzyl; in certain embodiments $R^6$ is isopropyl; and in certain embodiments wherein $R^6$ is isopropyl, the stereochemistry of the carbon to which $R^6$ is bonded is of the S-configuration.

In certain embodiments of compounds of Formula (I), $R^1$ is hydrogen; $R^2$ is

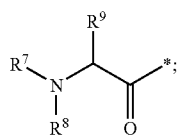

$R^3$ is —$NHR^{12}$, wherein $R^{12}$ is a moiety of structural Formula (II); wherein X is O;

q is 1;

each of $R^{13}$ and $R^{14}$ is hydrogen;

$R^{15}$ is hydrogen;

W is $NR^{18}$, and $R^{18}$ is hydrogen; and $R^{16}$ is —$C(O)OR^{20}$ wherein $R^{20}$ is selected from methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, hex-1-yl, hex-2-yl, hex-3-yl, 2-methylpent-1-yl, 3-methylpent-1-yl, vinyl, propen-2-yl, buten-2-yl, phenethen-2-yl, cyclopentyl, cyclohexyl, cyclopenten-1-yl, cyclohexen-1-yl, phenyl, 4-methoxyphenyl, benzyl, and 4-methoxybenzyl.

In certain of the aforementioned embodiments, each of $R^7$ and $R^8$ is hydrogen; and $R^9$ is selected from hydrogen, methyl, isopropyl, isobutyl, sec-butyl, tert-butyl, cyclopentyl, cyclohexyl, —$CH_2OH$, —$CH(OH)CH_3$, —$CH_2CO_2H$, —$CH_2CH_2CO_2H$, —$CH_2CONH_2$, —$CH_2CH_2CONH_2$, —$CH_2CH_2SCH_3$, —$CH_2SH$, —$CH_2(CH_2)_3NH_2$, —$CH_2CH_2CH_2NHC(NH)NH_2$, phenyl, benzyl, 4-hydroxybenzyl, 4-imidazolylmethyl, and 3-indolylmethyl; or $R^8$ and $R^9$ together with the nitrogen atom to which they are bonded form an azetidine, pyrrolidine, or piperidine ring.

In certain of the aforementioned embodiments, each of $R^7$ and $R^8$ is hydrogen; $R^9$ is selected from methyl, isopropyl, isobutyl, sec-butyl, tert-butyl, and benzyl; in certain embodiments, $R^9$ is isopropyl; and in certain embodiments wherein $R^9$ is isopropyl, the stereochemistry of the carbon to which $R^9$ is bonded is of the S-configuration.

In certain embodiments of compounds of Formula (I), $R^1$ is selected from hydrogen, acyl, substituted acyl, acyloxyalkylcarbonyl, substituted acyloxyalkylcarbonyl, oxycarbonyl, substituted oxycarbonyl, and

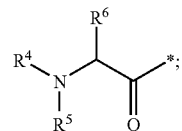

$R^2$ is selected from hydrogen, acyl, substituted acyl, acyloxyalkylcarbonyl, substituted acyloxyalkylcarbonyl, oxycarbonyl, substituted oxycarbonyl, and

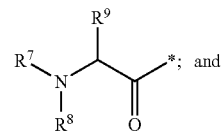

$R^3$ is —$NHR^{12}$, wherein $R^{12}$ is a moiety of structural Formula (II); wherein X is $CH_2$;

q is 1;

each of $R^{13}$ and $R^{14}$ is hydrogen;

$R^{15}$ is hydrogen;

W is O; and $R^{16}$ is —$C(O)R^{19}$.

In certain of the aforementioned embodiments, $R^{19}$ is selected from $C_{1-6}$ alkyl, substituted $C_{1-6}$ alkyl, $C_{3-6}$ cycloalkyl, phenyl, substituted phenyl, $C_{7-9}$ phenylalkyl, pyridyl, and substituted pyridyl.

In certain of the aforementioned embodiments, $R^{19}$ is selected from methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, phenyl, 2-methylphenyl, 2,6-dimethylphenyl, 2-methoxyphenyl, 4-methoxyphenyl, 2,6-dimethoxyphenyl, benzyl, phenethyl, styryl, cyclopropyl, cyclobutyl, cyclopentyl, cyclohexyl, and 3-pyridyl.

In certain of the aforementioned embodiments, $R^{19}$ is selected from methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, phenyl, 2-methylphenyl, 2,6-dimethylphenyl, 2-methoxyphenyl, 4-methoxyphenyl, 2,6-dimethoxyphenyl, benzyl, phenethyl, styryl, cyclopropyl, cyclobutyl, cyclopentyl, cyclohexyl, and 3-pyridyl; and each of $R^1$ and $R^2$ is hydrogen.

In certain of the aforementioned embodiments, $R^{19}$ is selected from methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, phenyl, 2-methylphenyl, 2,6-dimethylphenyl, 2-methoxyphenyl, 4-methoxyphenyl, 2,6-dimethoxyphenyl, benzyl, phenethyl, styryl, cyclopropyl, cyclobutyl, cyclopentyl, cyclohexyl, and 3-pyridyl; $R^1$ is

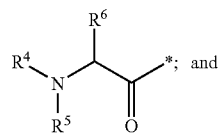

$R^2$ is hydrogen.

In certain of the aforementioned embodiments, $R^{19}$ is selected from methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, phenyl, 2-methylphenyl, 2,6-dimethylphenyl, 2-methoxyphenyl, 4-methoxyphenyl, 2,6-dimethoxyphenyl, benzyl, phenethyl, styryl, cyclopropyl, cyclobutyl, cyclopentyl, cyclohexyl, and 3-pyridyl; $R^1$ is

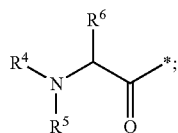

$R^2$ is hydrogen;

each of $R^4$ and $R^5$ is hydrogen; and $R^6$ is selected from hydrogen, methyl, isopropyl, isobutyl, sec-butyl, tert-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$CH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl, and 3-indolylmethyl; or $R^5$ and $R^6$ together with the nitrogen atom to which they are bonded form an azetidine, pyrrolidine, or piperidine ring.

In certain of the aforementioned embodiments, $R^{19}$ is selected from methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, phenyl, 2-methylphenyl, 2,6-dimethylphenyl, 2-methoxyphenyl, 4-methoxyphenyl, 2,6-dimethoxyphenyl, benzyl, phenethyl, styryl, cyclopropyl, cyclobutyl, cyclopentyl, cyclohexyl, and 3-pyridyl; $R^1$ is

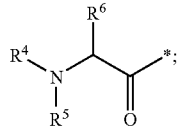

$R^2$ is hydrogen;

each of $R^4$ and $R^5$ is hydrogen; $R^6$ is selected from methyl, isopropyl, isobutyl, sec-butyl, tert-butyl, and benzyl; in certain embodiments $R^6$ is isopropyl; and in certain embodiments wherein $R^6$ is isopropyl, the stereochemistry of the carbon to which $R^6$ is bonded is of the S-configuration.

In certain embodiments of compounds of Formula (I), $R^1$ is hydrogen; $R^2$ is

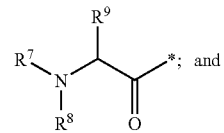

$R^3$ is —NHR$^{12}$, wherein $R^{12}$ is a moiety of structural Formula (II); wherein X is CH$_2$;

q is 1;

each of $R^{13}$ and $R^{14}$ is hydrogen;

$R^{15}$ is hydrogen;

W is O; and $R^{16}$ is —C(O)R$^{19}$ wherein $R^{19}$ is selected from methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, phenyl, 2-methylphenyl, 2,6-dimethylphenyl, 2-methoxyphenyl, 4-methoxyphenyl, 2,6-dimethoxyphenyl, benzyl, phenethyl, styryl, cyclopropyl, cyclobutyl, cyclopentyl, cyclohexyl, and 3-pyridyl.

In certain of the aforementioned embodiments, each of $R^7$ and $R^8$ is hydrogen; and $R^9$ is selected from hydrogen, methyl, isopropyl, isobutyl, sec-butyl, tert-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$N$_2$, —CH$_2$CH$_2$CH$_2$NHC(NH)NH$_2$, phenyl, benzyl, 4-hydroxybenzyl, 4-imidazolylmethyl, and 3-indolylmethyl; or $R^8$ and $R^9$ together with the nitrogen atom to which they are bonded form an azetidine, pyrrolidine, or piperidine ring.

In certain of the aforementioned embodiments, each of $R^7$ and $R^8$ is hydrogen; $R^9$ is selected from methyl, isopropyl, isobutyl, sec-butyl, tert-butyl, and benzyl; in certain embodiments $R^9$ is isopropyl; and in certain embodiments wherein $R^9$ is isopropyl, the stereochemistry of the carbon to which $R^9$ is bonded is of the S-configuration.

In certain embodiments of compounds of Formula (I), $R^1$ is selected from hydrogen, acyl, substituted acyl, acyloxyalkylcarbonyl, substituted acyloxyalkylcarbonyl, oxycarbonyl, substituted oxycarbonyl, and

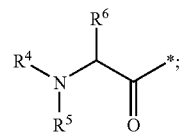

$R^2$ is selected from hydrogen, acyl, substituted acyl, acyloxyalkylcarbonyl, substituted acyloxyalkylcarbonyl, oxycarbonyl, substituted oxycarbonyl, and

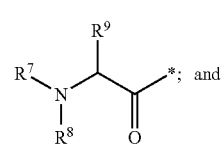

$R^3$ is —$NHR^{12}$, wherein $R^{12}$ is a moiety of structural Formula (II); wherein X is $CH_2$;

q is 1;

each of $R^{13}$ and $R^{14}$ is hydrogen;

$R^{15}$ is hydrogen;

W is O; and $R^{16}$ is —$C(O)OR^{20}$.

In certain of the aforementioned embodiments, $R^{20}$ is selected from $C_{1-6}$ alkanyl, $C_{2-6}$ alk-1-en-2-yl, 2-$C_{3-7}$ cycloalkyl-eth-1-en-2-yl, 2-phenyleth-1-en-2-yl, substituted 2-phenyleth-1-en-2-yl, $C_{3-7}$ cycloalkanyl, $C_{5-7}$ cycloalk-1-en-1-yl, phenyl, naphthyl, halophenyl, methoxyphenyl, cyanophenyl, carboxyphenyl, $C_{1-4}$ alkoxycarbonylphenyl, aminophenyl, halobenzyl, methoxybenzyl, cyanobenzyl, carboxybenzyl, $C_{1-4}$ alkoxycarbonylbenzyl, aminobenzyl, furyl, thienyl, pyrrolyl, imidazoyl, oxazolyl, pyridyl, pyrimidyl, pyrazinyl, and triazinyl.

In certain of the aforementioned embodiments, $R^{20}$ is selected from methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, hex-1-yl, hex-2-yl, hex-3-yl, 2-methylpent-1-yl, 3-methylpent-1-yl, vinyl, propen-2-yl, buten-2-yl, phenethen-2-yl, cyclopentyl, cyclohexyl, cyclopenten-1-yl, cyclohexen-1-yl, phenyl, 4-methoxyphenyl, benzyl, and 4-methoxybenzyl.

In certain of the aforementioned embodiments, $R^{20}$ is selected from methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, hex-1-yl, hex-2-yl, hex-3-yl, 2-methylpent-1-yl, 3-methylpent-1-yl, vinyl, propen-2-yl, buten-2-yl, phenethen-2-yl, cyclopentyl, cyclohexyl, cyclopenten-1-yl, cyclohexen-1-yl, phenyl, 4-methoxyphenyl, benzyl, and 4-methoxybenzyl; and each of $R^1$ and $R^2$ is hydrogen.

In certain embodiments of compounds of Formula (I), $R^1$ is

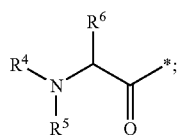

$R^2$ is hydrogen;

$R^3$ is —$NHR^{12}$, wherein $R^{12}$ is a moiety of structural Formula (II); wherein X is $CH_2$;

q is 1;

each of $R^{13}$ and $R^{14}$ is hydrogen;

$R^{15}$ is hydrogen;

W is O; and

R is —$C(O)OR^{20}$.

In certain of the aforementioned embodiments, each of $R^4$ and $R^5$ is hydrogen; and $R^6$ is selected from hydrogen, methyl, isopropyl, isobutyl, sec-butyl, tert-butyl, cyclopentyl, cyclohexyl, —$CH_2OH$, —$CH(OH)CH_3$, —$CH_2CO_2H$, —$CH_2CH_2CO_2H$, —$CH_2CONH_2$, —$CH_2CH_2CONH_2$, —$CH_2CH_2SCH_3$, —$CH_2SH$, —$CH_2(CH_2)_3NH_2$, —$CH_2CH_2CH_2NHC(NH)NH_2$, phenyl, benzyl, 4-hydroxybenzyl, 4-imidazolylmethyl, and 3-indolylmethyl; or $R^5$ and $R^6$ together with the nitrogen atom to which they are bonded form an azetidine, pyrrolidine, or piperidine ring.

In certain of the aforementioned embodiments, each of $R^4$ and $R^5$ is hydrogen; $R^6$ is selected from methyl, isopropyl, isobutyl, sec-butyl, tert-butyl, and benzyl; in certain embodiments $R^6$ is isopropyl; and in certain embodiments wherein $R^6$ is isopropyl, the stereochemistry of the carbon to which $R^6$ is bonded is of the S-configuration.

In certain embodiments of compounds of Formula (I), $R^1$ is hydrogen; $R^2$ is

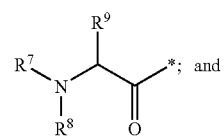

$R^3$ is —$NHR^{12}$, wherein $R^{12}$ is a moiety of structural Formula (II); wherein X is $CH_2$;

q is 1;

each of $R^{13}$ and $R^{14}$ is hydrogen;

$R^{15}$ is hydrogen;

W is O; and $R^{16}$ is —$C(O)OR^{20}$.

In certain of the aforementioned embodiments, each of $R^7$ and $R^8$ is hydrogen; and $R^9$ is selected from hydrogen, methyl, isopropyl, isobutyl, sec-butyl, tert-butyl, cyclopentyl, cyclohexyl, —$CH_2OH$, —$CH(OH)CH_3$, —$CH_2CO_2H$, —$CH_2CH_2CO_2H$, —$CH_2CONH_2$, —$CH_2CH_2CONH_2$, —$CH_2CH_2SCH_3$, —$CH_2SH$, —$CH_2(CH_2)_3NH_2$, —$CH_2CH_2CH_2NHC(NH)NH_2$, phenyl, benzyl, 4-hydroxybenzyl, 4-imidazolylmethyl, and 3-indolylmethyl; or $R^8$ and $R^9$ together with the nitrogen atom to which they are bonded form an azetidine, pyrrolidine, or piperidine ring.

In certain of the aforementioned embodiments, each of $R^7$ and $R^8$ is hydrogen; $R^9$ is selected from methyl, isopropyl, isobutyl, sec-butyl, tert-butyl, and benzyl; in certain embodiments $R^9$ is isopropyl; and in certain embodiments wherein $R^9$ is isopropyl, the stereochemistry of the carbon to which $R^9$ is bonded is of the S-configuration.

In certain embodiments of compounds of Formula (I), $R^1$ is selected from hydrogen, acyl, substituted acyl, acyloxyalkylcarbonyl, substituted acyloxyalkylcarbonyl, oxycarbonyl, substituted oxycarbonyl, and

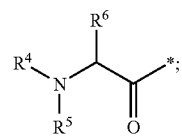

$R^2$ is selected from hydrogen, acyl, substituted acyl, acyloxyalkylcarbonyl, substituted acyloxyalkylcarbonyl, oxycarbonyl, substituted oxycarbonyl, and

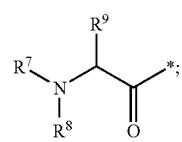

$R^3$ is —$NHR^{12}$, wherein $R^{12}$ is a moiety of structural Formula (II); wherein
X is $CH_2$;
q is 1;
each of $R^{13}$ and $R^{14}$ is hydrogen;
$R^{15}$ is hydrogen;
W is $NR^{18}$, wherein $R^{18}$ is hydrogen; and
$R^{16}$ is —$C(O)OR^{20}$.

In certain of the aforementioned embodiments, $R^{20}$ is selected from $C_{1-6}$ alkanyl, $C_{2-6}$ alk-1-en-2-yl, 2-$C_{3-7}$ cycloalkyl-eth-1-en-2-yl, 2-phenyleth-1-en-2-yl, substituted 2-phenyleth-1-en-2-yl, $C_{3-7}$ cycloalkanyl, $C_{5-7}$ cycloalk-1-en-1-yl, phenyl, naphthyl, halophenyl, methoxyphenyl, cyanophenyl, carboxyphenyl, $C_{1-4}$ alkoxycarbonylphenyl, aminophenyl, halobenzyl, methoxybenzyl, cyanobenzyl, carboxybenzyl, $C_{1-4}$ alkoxycarbonylbenzyl, aminobenzyl, furyl, thienyl, pyrrolyl, imidazoyl, oxazolyl, pyridyl, pyrimidyl, pyrazinyl, and triazinyl.

In certain of the aforementioned embodiments, $R^{20}$ is selected from methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, hex-1-yl, hex-2-yl, hex-3-yl, 2-methylpent-1-yl, 3-methylpent-1-yl, vinyl, propen-2-yl, buten-2-yl, phenethen-2-yl, cyclopentyl, cyclohexyl, cyclopenten-1-yl, cyclohexen-1-yl, phenyl, 4-methoxyphenyl, benzyl, and 4-methoxybenzyl.

In certain of the aforementioned embodiments, $R^{20}$ is selected from methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, hex-1-yl, hex-2-yl, hex-3-yl, 2-methylpent-1-yl, 3-methylpent-1-yl, vinyl, propen-2-yl, buten-2-yl, phenethen-2-yl, cyclopentyl, cyclohexyl, cyclopenten-1-yl, cyclohexen-1-yl, phenyl, 4-methoxyphenyl, benzyl, and 4-methoxybenzyl; and each of $R^1$ and $R^2$ is hydrogen.

In certain embodiments of compounds of Formula (I), $R^1$ is

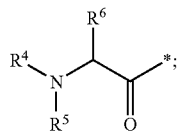

$R^2$ is hydrogen; and
$R^3$ is —$NHR^{12}$, wherein $R^{12}$ is a moiety of structural Formula (II); wherein
X is $CH_2$;
q is 1;
each of $R^{13}$ and $R^{14}$ is hydrogen;
$R^{15}$ is hydrogen;
W is $NR^{18}$, wherein $R^{18}$ is hydrogen; and
$R^{16}$ is —$C(O)OR^{20}$.

In certain of the aforementioned embodiments, each of $R^4$ and $R^5$ is hydrogen; and $R^6$ is selected from hydrogen, methyl, isopropyl, isobutyl, sec-butyl, tert-butyl, cyclopentyl, cyclohexyl, —$CH_2OH$, —$CH(OH)CH_3$, —$CH_2CO_2H$, —$CH_2CH_2CO_2H$, —$CH_2CONH_2$, —$CH_2CH_2CONH_2$, —$CH_2CH_2SCH_3$, —$CH_2SH$, —$CH_2(CH_2)_3NH_2$, —$CH_2CH_2CH_2NHC(NH)NH_2$, phenyl, benzyl, 4-hydroxybenzyl, 4-imidazolylmethyl, and 3-indolylmethyl; or $R^5$ and $R^6$ together with the nitrogen atom to which they are bonded form an azetidine, pyrrolidine, or piperidine ring.

In certain of the aforementioned embodiments, each of $R^4$ and $R^5$ is hydrogen; $R^6$ is selected from methyl, isopropyl, isobutyl, sec-butyl, tert-butyl, and benzyl; in certain embodiments, $R^6$ is isopropyl; and in certain embodiments wherein $R^6$ is isopropyl, the stereochemistry of the carbon to which $R^6$ is bonded is of the S-configuration.

In certain embodiments of compounds of Formula (I), $R^1$ is hydrogen; $R^2$ is

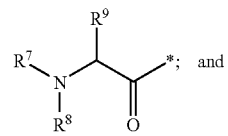

$R^3$ is —$NHR^{12}$, wherein $R^{12}$ is a moiety of structural Formula (II); wherein
X is $CH_2$;
q is 1;
each of $R^{13}$ and $R^{14}$ is hydrogen;
$R^{15}$ is hydrogen;
W is $NR^{18}$, wherein $R^{18}$ is hydrogen; and
$R^{16}$ is —$C(O)OR^{20}$.

In certain of the aforementioned embodiments, each of $R^7$ and $R^8$ is hydrogen; and $R^9$ is selected from hydrogen, methyl, isopropyl, isobutyl, sec-butyl, tert-butyl, cyclopentyl, cyclohexyl, —$CH_2OH$, —$CH(OH)CH_3$, —$CH_2CO_2H$, —$CH_2CH_2CO_2H$, —$CH_2CONH_2$, —$CH_2CH_2CONH_2$, —$CH_2CH_2SCH_3$, —$CH_2SH$, —$CH_2(CH_2)_3NH_2$, —$CH_2CH_2CH_2NHC(NH)NH_2$, phenyl, benzyl, 4-hydroxybenzyl, 4-imidazolylmethy, and 3-indolylmethyl; or $R^8$ and $R^9$ together with the nitrogen atom to which they are bonded form an azetidine, pyrrolidine, or piperidine ring.

In certain of the aforementioned embodiments, each of $R^7$ and $R^8$ is hydrogen; and $R^9$ is selected from methyl, isopropyl, isobutyl, sec-butyl, tert-butyl, and benzyl; in certain embodiments, $R^9$ is isopropyl; and in certain embodiments wherein $R^9$ is isopropyl, the stereochemistry of the carbon to which $R^9$ is bonded is of the S-configuration.

In certain embodiments of compounds of Formula (I), $R^1$ is selected from hydrogen, acyl, substituted acyl, acyloxyalkylcarbonyl, substituted acyloxyalkylcarbonyl, oxycarbonyl, substituted oxycarbonyl, and

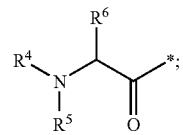

$R^2$ is selected from hydrogen, acyl, substituted acyl, acyloxyalkylcarbonyl, substituted acyloxyalkylcarbonyl, oxycarbonyl, substituted oxycarbonyl, and

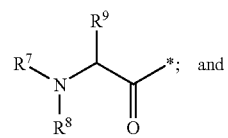

$R^3$ is —$NHR^{12}$, wherein $R^{12}$ is a moiety of structural Formula (II); wherein
X is O;
q is 1;
each of $R^{13}$ and $R^{14}$ is hydrogen;

$R^{15}$ is hydrogen;
W is $NR^{18}$ wherein $R^{18}$ is selected from hydrogen and methyl; and
$R^{16}$ is

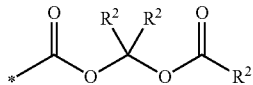

wherein $R^{21}$ is selected from hydrogen, methyl, ethyl, propyl, isopropyl, tert-butyl, cyclopentyl, cyclohexyl, and phenyl; $R^{22}$ is hydrogen; and $R^{23}$ is selected from methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, 1,1-dimethoxyethyl, 1,1-diethoxyethyl, phenyl, 2-methylphenyl, 2,6-dimethylphenyl, 2-methoxyphenyl, 4-methoxyphenyl, 2,6-dimethoxyphenyl, benzyl, phenethyl, styryl, cyclopropyl, cyclobutyl, cyclopentyl, cyclohexyl, and 3-pyridyl.

In certain of the aforementioned embodiments, $R^{23}$ is selected from methyl, propyl, isopropyl, tert-butyl, phenyl, 2-methylphenyl, 2,6-dimethylphenyl, 2-methoxyphenyl, 4-methoxyphenyl, 2,6-dimethoxyphenyl, benzyl, cyclopentyl, and cyclohexyl.

In certain of the aforementioned embodiments, $R^{23}$ is selected from methyl, propyl, isopropyl, tert-butyl, phenyl, 2-methylphenyl, 2,6-dimethylphenyl, 2-methoxyphenyl, 4-methoxyphenyl, 2,6-dimethoxyphenyl, benzyl, cyclopentyl, and cyclohexyl; each of $R^{21}$ and $R^{23}$ is tert-butyl; and each of $R^{18}$ and $R^{22}$ is hydrogen.

In certain of the aforementioned embodiments, $R^{23}$ is selected from methyl, propyl, isopropyl, tert-butyl, phenyl, 2-methylphenyl, 2,6-dimethylphenyl, 2-methoxyphenyl, 4-methoxyphenyl, 2,6-dimethoxyphenyl, benzyl, cyclopentyl, and cyclohexyl; and each of $R^1$ and $R^2$ is hydrogen.

In certain of the aforementioned embodiments, $R^{23}$ is selected from methyl, propyl, isopropyl, tert-butyl, phenyl, 2-methylphenyl, 2,6-dimethylphenyl, 2-methoxyphenyl, 4-methoxyphenyl, 2,6-dimethoxyphenyl, benzyl, cyclopentyl, and cyclohexyl; each of $R^{21}$ and $R^{23}$ is tert-butyl; each of $R^{18}$ and $R^{22}$ is hydrogen; and each of $R^1$ and $R^2$ is hydrogen.

In certain embodiments of compounds of Formula (I), $R^1$ is

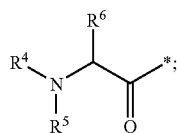

$R^2$ is hydrogen; and
$R^3$ is $-NHR^{12}$, wherein $R^{12}$ is a moiety of structural Formula (II); wherein
X is O;
q is 1;
each of $R^{13}$ and $R^{14}$ is hydrogen;
$R^{15}$ is hydrogen;
W is $NR^{18}$ wherein $R^{18}$ is selected from hydrogen and methyl; and
$R^{16}$ is

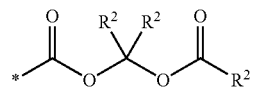

wherein $R^{21}$ is selected from hydrogen, methyl, ethyl, propyl, isopropyl, tert-butyl, cyclopentyl, cyclohexyl, and phenyl; $R^{22}$ is hydrogen; and $R^{23}$ is selected from methyl, propyl, isopropyl, tert-butyl, phenyl, 2-methylphenyl, 2,6-dimethylphenyl, 2-methoxyphenyl, 4-methoxyphenyl, 2,6-dimethoxyphenyl, benzyl, cyclopentyl, and cyclohexyl.

In certain of the aforementioned embodiments, each of $R^4$ and $R^5$ is hydrogen; and $R^6$ is selected from hydrogen, methyl, isopropyl, isobutyl, sec-butyl, tert-butyl, cyclopentyl, cyclohexyl, $-CH_2OH$, $-CH(OH)CH_3$, $-CH_2CO_2H$, $-CH_2CH_2CO_2H$, $-CH_2CONH_2$, $-CH_2CH_2CONH_2$, $-CH_2CH_2SCH_3$, $-CH_2SH$, $-CH_2(CH_2)_3NH_2$, $-CH_2CH_2CH_2NHC(NH)NH_2$, phenyl, benzyl, 4-hydroxybenzyl, 4-imidazolylmethyl, and 3-indolylmethyl; or $R^5$ and $R^6$ together with the nitrogen atom to which they are bonded form an azetidine, pyrrolidine, or piperidine ring.

In certain of the aforementioned embodiments, each of $R^4$ and $R^5$ is hydrogen; and $R^6$ is selected from methyl, isopropyl, isobutyl, sec-butyl, tert-butyl, and benzyl; in certain embodiments, $R^6$ is isopropyl; and in certain embodiments wherein $R^6$ is isopropyl, the stereochemistry of the carbon to which $R^6$ is bonded is of the S-configuration.

In certain embodiments of compounds of Formula (I), $R^1$ is

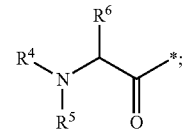

$R^2$ is hydrogen; and
$R^3$ is $-NHR^{12}$, wherein $R^{12}$ is a moiety of structural Formula (II); wherein
X is O;
q is 1;
each of $R^{13}$ and $R^{14}$ is hydrogen;
$R^{15}$ is hydrogen;
W is $NR^{18}$ wherein $R^{18}$ is selected from hydrogen and methyl; and
$R^{16}$ is

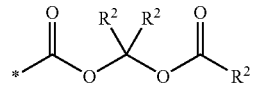

wherein $R^{21}$ is selected from hydrogen, methyl, ethyl, propyl, isopropyl, tert-butyl, cyclopentyl, cyclohexyl, and phenyl; $R^{22}$ is hydrogen; and $R^{23}$ is selected from methyl, propyl, isopropyl, tert-butyl, phenyl, 2-methylphenyl, 2,6-dimethylphenyl, 2-methoxyphenyl, 4-methoxyphenyl, 2,6-dimethoxyphenyl, benzyl, cyclopentyl, and cyclohexyl; each of $R^{21}$ and $R^{23}$ is tert-butyl; and each of $R^{18}$ and $R^{22}$ is hydrogen.

In certain of the aforementioned embodiments, each of $R^4$ and $R^5$ is hydrogen; and $R^6$ is selected from hydrogen, methyl, isopropyl, isobutyl, sec-butyl, tert-butyl, cyclopentyl, cyclohexyl, $-CH_2OH$, $-CH(OH)CH_3$, $-CH_2CO_2H$, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl, and 3-indolylmethyl; or R$^5$ and R$^6$ together with the nitrogen atom to which they are bonded form an azetidine, pyrrolidine, or piperidine ring.

In certain of the aforementioned embodiments, each of R$^4$ and R$^5$ is hydrogen; and R$^6$ is selected from methyl, isopropyl, isobutyl, sec-butyl, tert-butyl, and benzyl; in certain embodiments, R$^6$ is isopropyl; and in certain embodiments wherein R$^6$ is isopropyl, the stereochemistry of the carbon to which R$^6$ is bonded is of the S-configuration.

In certain of the aforementioned embodiments, R$^1$ is hydrogen; R$^2$ is

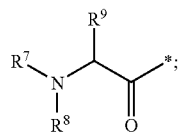

each of R$^7$ and R$^8$ is hydrogen; and R$^9$ is selected from hydrogen, methyl, isopropyl, isobutyl, sec-butyl, tert-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl, and 3-indolylmethyl; or R$^8$ and R$^9$ together with the nitrogen atom to which they are bonded form an azetidine, pyrrolidine, or piperidine ring.

In certain embodiments, R$^9$ is selected from methyl, isopropyl, isobutyl, sec-butyl, tert-butyl, and benzyl. In certain embodiments, R$^9$ is isopropyl, and in certain embodiments, the stereochemistry of the carbon to which R$^9$ is bonded is of the S-configuration.

In certain embodiments of compounds of Formula (I), R$^1$ is hydrogen; R$^2$ is

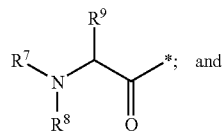

R$^3$ is —NHR$^{12}$, wherein R$^{12}$ is a moiety of structural Formula (II); wherein
X is O;
q is 1;
each of R$^{13}$ and R$^{14}$ is hydrogen;
R$^{15}$ is hydrogen;
W is NR$^{18}$ wherein R$^{18}$ is selected from hydrogen and methyl; and
R$^{16}$ is

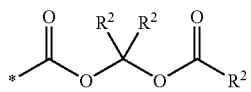

wherein R$^{21}$ is selected from hydrogen, methyl, ethyl, propyl, isopropyl, tert-butyl, cyclopentyl, cyclohexyl, and phenyl;
R$^{22}$ is hydrogen; and
R$^{23}$ is selected from methyl, propyl, isopropyl, tert-butyl, phenyl, 2-methylphenyl, 2,6-dimethylphenyl, 2-methoxyphenyl, 4-methoxyphenyl, 2,6-dimethoxyphenyl, benzyl, cyclopentyl, and cyclohexyl.

In certain of the aforementioned embodiments, each of R$^4$ and R$^5$ is hydrogen; and R$^6$ is selected from hydrogen, methyl, isopropyl, isobutyl, sec-butyl, tert-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl, and 3-indolylmethyl; or R$^5$ and R$^6$ together with the nitrogen atom to which they are bonded form an azetidine, pyrrolidine, or piperidine ring.

In certain of the aforementioned embodiments, each of R$^4$ and R$^5$ is hydrogen; and R$^6$ is selected from methyl, isopropyl, isobutyl, sec-butyl, tert-butyl, and benzyl; in certain embodiments, R$^6$ is isopropyl; and in certain embodiments wherein R$^6$ is isopropyl, the stereochemistry of the carbon to which R$^6$ is bonded is of the S-configuration.

In certain embodiments of compounds of Formula (I), R$^1$ is hydrogen;
R$^2$ is

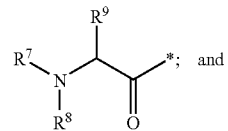

R$^3$ is —NHR$^{12}$, wherein R$^{12}$ is a moiety of structural Formula (II); wherein
X is O;
q is 1;
each of R$^{13}$ and R$^{14}$ is hydrogen;
R$^{15}$ is hydrogen;
W is NR$^{18}$ wherein R$^{18}$ is selected from hydrogen and methyl; and
R$^{16}$ is

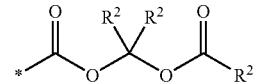

wherein R$^{21}$ is selected from hydrogen, methyl, ethyl, propyl, isopropyl, tert-butyl, cyclopentyl, cyclohexyl, and phenyl;
R$^{22}$ is hydrogen;
R$^{23}$ is selected from methyl, propyl, isopropyl, tert-butyl, phenyl, 2-methylphenyl, 2,6-dimethylphenyl, 2-methoxyphenyl, 4-methoxyphenyl, 2,6-dimethoxyphenyl, benzyl, cyclopentyl, and cyclohexyl; each of R$^{21}$ and R$^{23}$ is tert-butyl; and each of R$^{18}$ and R$^{22}$ is hydrogen.

In certain of the aforementioned embodiments, each of R$^4$ and R$^5$ is hydrogen; and R$^6$ is selected from hydrogen, methyl, isopropyl, isobutyl, sec-butyl, tert-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl, and 3-indolylmethyl; or R$^5$ and R$^6$ together with the nitrogen atom to which they are bonded form an azetidine, pyrrolidine, or piperidine ring.

In certain of the aforementioned embodiments, each of $R^4$ and $R^5$ is hydrogen; and $R^6$ is selected from methyl, isopropyl, isobutyl, sec-butyl, tert-butyl, and benzyl; in certain embodiments, $R^6$ is isopropyl; and in certain embodiments wherein $R^6$ is isopropyl, the stereochemistry of the carbon to which $R^6$ is bonded is of the S-configuration.

In certain embodiments of compounds of Formula (I), $R^{21}$ and $R^{22}$ are both not hydrogen. In compounds of Formula (I) wherein each of $R^{21}$ and $R^{22}$ is hydrogen, an in vivo metabolite is formaldehyde. It is desirable that compounds administered to patients to produce potentially toxic or otherwise undesired metabolites such as formaldehyde.

Certain compounds of structural Formula (I) may be administered orally and are transported across cells (i.e., enterocytes) lining the lumen of the gastrointestinal tract either by active transport, passive diffusion or by a mixture of both active and passive processes. Previous studies have characterized multiple cellular transport mechanisms for nucleoside analog drugs and their derivatives (for a review, see Balimane et al., *Adv. Drug Delivery Rev.* 1999, 39, 183-209), including equilibrative and concentrative nucleoside transporters (ENT's and CNT's respectively). Certain compounds of structural Formula (I) are substrates for one or more of the nucleoside transporters that transport β-D-ribofuranosyl cytidine derivatives (i.e. ENT1, ENT2, CNT1 and CNT3). Methods for determining whether compounds of Formula (I) serve as substrates for ENT and CNT transporters are disclosed in Example 3 herein.

Other compounds of structural Formula (I) are substrates for the proton-coupled intestinal peptide transport system (PEPT1) (Leibach et al., *Annu. Rev. Nutr.* 1996, 16, 99-119), which typically mediates the cellular uptake of small intact peptides consisting of two or three amino acids that are derived from the digestion of dietary proteins. In the intestine, where small peptides are not effectively absorbed by passive diffusion, PEPT1 may act as a vehicle for their effective uptake across the apical membrane of the gastric mucosa. Methods for determining whether compounds of Formula (I) serve as substrates for the PEPT1 transporter are disclosed in Example 2 herein. In vitro systems, which use cells engineered to heterologously express the transport system, or cell-lines that endogenously express the transporter (e.g., Caco-2 cells) may be used to assay transport of compounds of Formula (I) by the PEPT1 transporter.

Regardless of the method of transport across the gastrointestinal (GI) mucosa, preferred compounds of Formula (I) are prodrugs of β-D-2'-C-methyl-ribofuranosyl cytidine (1) that are sufficiently stable in the intestinal lumen and during transit across the enterocyte barrier that little or no compound (1) is liberated within the intestinal cells themselves. This limits direct exposure of sensitive GI cells to toxic levels of (1). Masking enterocyte toxicity may be accomplished by appending an appropriate promoiety at either the N-4 nitrogen, or the 5'-O or 3'-O positions of (1), or a combination of such modifications. However, once the prodrug has entered the portal circulation and is delivered to the liver, cleavage of compound (1) via enzymatic, chemical, or a combination of enzymatic and chemical means should occur in order that a therapeutically effective concentration of (1) is provided to virally infected cells (hepatocytes). Cleavage of the prodrug may also occur within the systemic circulation (e.g., plasma). In vitro assay methods for evaluating the stability of compounds of Formula (I) in the presence of cellular homogenates and other tissue preparations are disclosed in Example 4.

Synthesis of Compounds

The compounds disclosed herein may be obtained, for example, via synthetic methods illustrated in FIGS. 1-8. Additional synthetic methods are disclosed in U.S. Application Publication No. 2004/0142857 and Sommadossi et al., U.S. Application Publication No. 2004/0077587, each of which is incorporated by reference herein in its entirety. Starting materials useful for preparing compounds and intermediates thereof are commercially available or can be prepared by well-known synthetic methods (Harrison et al., "Compendium of Synthetic Organic Methods", Vols. 1-8 (John Wiley and Sons, 1971-1996); "Beilstein Handbook of Organic Chemistry," Beilstein Institute of Organic Chemistry, Frankfurt, Germany; Feiser et al., "Reagents for Organic Synthesis," Volumes 1-17, Wiley Interscience; Trost et al., "Comprehensive Organic Synthesis," Pergamon Press, 1991; "Theilheimer's Synthetic Methods of Organic Chemistry," Volumes 1-45, Karger, 1991; March, "Advanced Organic Chemistry," Wiley Interscience, 1991; Larock "Comprehensive Organic Transformations," VCH Publishers, 1989; Paquette, "Encyclopedia of Reagents for Organic Synthesis," John Wiley & Sons, 1995). Other methods for synthesis of the compounds provided by the present disclosure and/or starting materials are either described in the art or will be readily apparent to the skilled artisan. Alternatives to the reagents and/or protecting groups illustrated below may be found in the references provided above and in other compendiums well known to the skilled artisan. Accordingly, the synthetic methods and strategy presented herein are illustrative rather than comprehensive.

FIG. 1 illustrates a general synthetic route to monosubstituted (3' or 5' substituted) 2'-C-methyl-ribofuranosyl cytidine analogs. β-D-2'-C-methyl-ribofuranosyl cytidine (1) is treated with trimethylsilyl chloride (TMSCI) in pyridine to provide tetrasilyl derivative (III), which upon reaction with 1-(allyloxycarbonyl-oxy)-1H-benzotriazole (Alloc-OBT) yields allyl carbamate (IV). It should be noted that other methods of selectively protecting an amine group in the presence of hydroxy groups are known to the skilled artisan and may be used in lieu of the illustrated route to generate protected amine derivatives analogous to (IV). Compound (IV) may be treated with an acylating, acyloxyalkylcarbonylating, oxycarbonylating, or aminoacylating agent (or substituted variations thereof) to provide a mixture of alcohols (V) and (VI). Methods for effecting monofunctionalization of (IV) with the above agents are well-known to the skilled artisan and numerous examples thereof may be found in the chemical arts. Removal of the amine protecting group (e.g., with a palladium catalyst such as $Pd(PPh_3)_4$) followed by separation (e.g., via HPLC) provides 3'-monosubstituted 2'-C-methyl-ribofuranosyl cytidine analog (VII) and 5'-monosubstituted 2'-C-methyl-ribofuranosyl cytidine analog (VIII).

Figure 2:
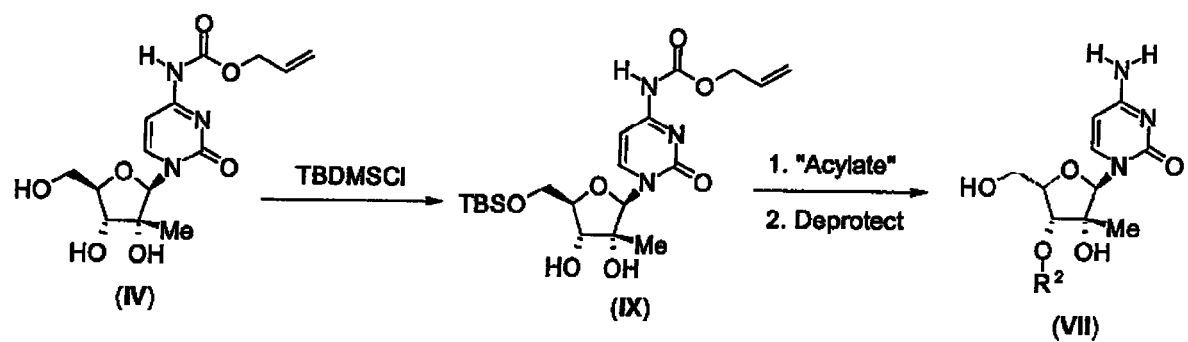
FIG. 2 illustrates a general synthetic route to 3'-substituted 2'-C-methyl-ribofuranosyl cytidine analogs.

FIG. 2 illustrates a general synthetic route to 3'-substituted 2'-C-methyl-ribofuranosyl cytidine analogs. The primary hydroxyl group in nucleoside (IV) is selectively protected (e.g., tert-butyldimethylsilyl chloride, imidazole) to yield the free 3'-hydroxyl compound (IX), which may be reacted with an appropriate acylating, acyloxyalkylcarbonylating, oxycarbonylating, or aminoacylating agent (or substituted variations thereof) and then deprotected (e.g., trifluoroacteic acid or tetra-n-butylammonium fluoride then palladium catalysis) to provide the 3'-substituted 2'-C-methyl-ribofuranosyl cytidine analog (VII).

Figure 3:
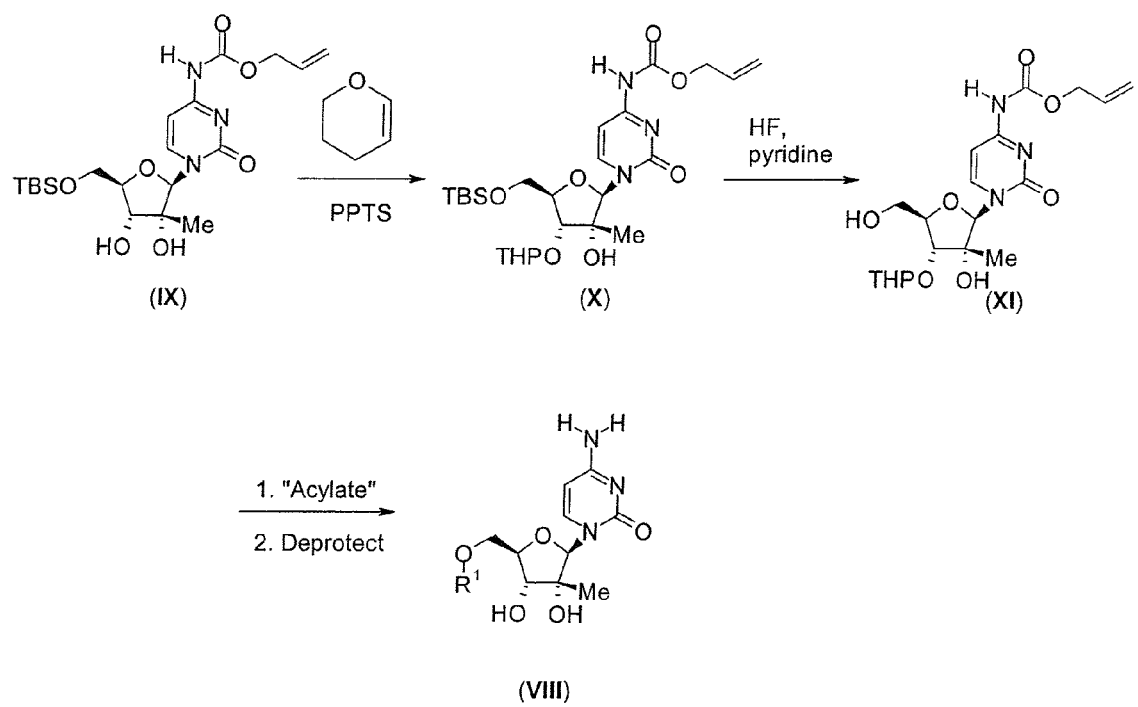
FIG. 3 illustrates a general synthetic route to 5'-substituted 2'-C-methyl-ribofuranosyl cytidine analogs.

FIG. 3 illustrates a general synthetic route to 5'-substituted 2'-C-methyl-ribofuranosyl cytidine analogs. The orthogonally protected nucleoside (X) is derived from compound (IX) by treatment with dihydropyran in the presence of an acid catalyst. Selective removal of the 5'-hydroxyl protecting group (e.g., HF, pyridine) to yield (XI), followed by reaction with a suitable acylating, acyloxyalkylcarbonylating, oxycarbonylating, or aminoacylating agent (or substituted variations thereof) and removal of the 3'-hydroxyl and nitrogen protecting groups provides the 5'-substituted 2'-C-methyl-ribofuranosyl cytidine analog (VIII).

Figure 4:
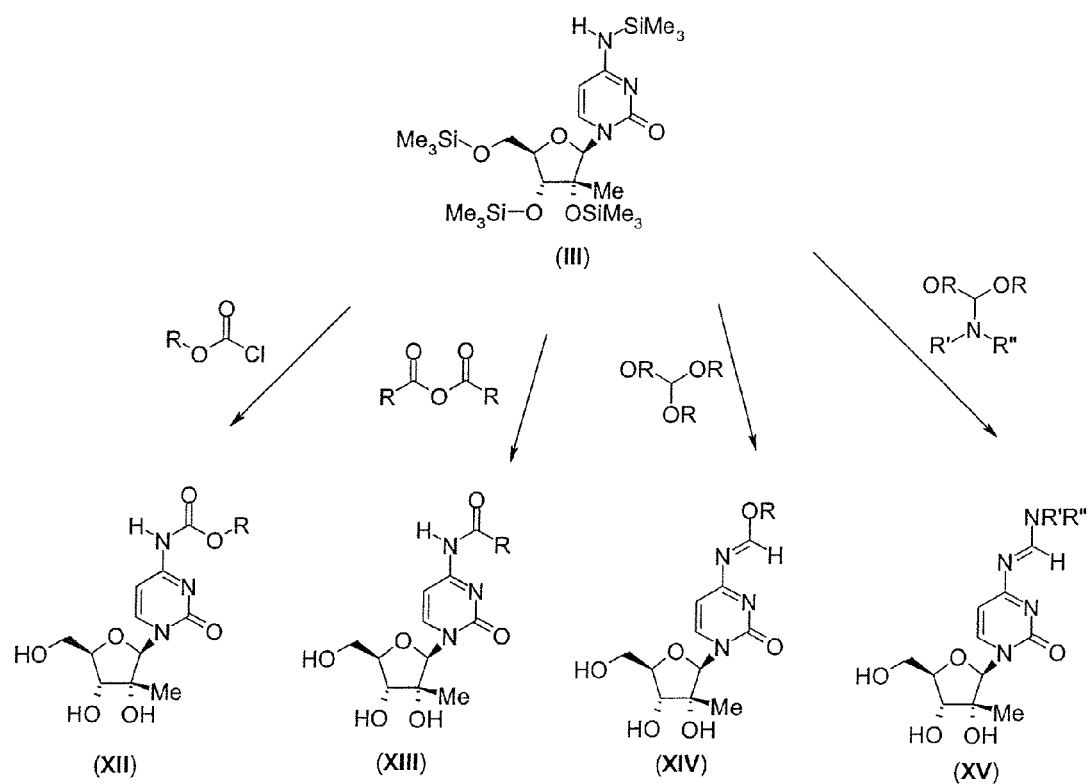
FIG. 4 illustrates some synthetic routes to N-4 substituted 2'-C-methyl-ribofuranosyl cytidine analogs.

FIG. 4 illustrates some synthetic routes to N-4 substituted 2'-C-methyl-ribofuranosyl cytidine analogs. A per-silylated nucleoside (III) is reacted with an alkoxycarbonyl derivative, an anhydride, an orthoester, or a formamide acetal to provide carbamate (XII), amide (XIII), imidate (XIV), and amidine (XV) derivatives, respectively. Carbamate derivatives (XII) may also be obtained via treatment of (III) with phosgene (or a phosgene equivalent) followed by reaction with an alcohol compound.

Figure 5:
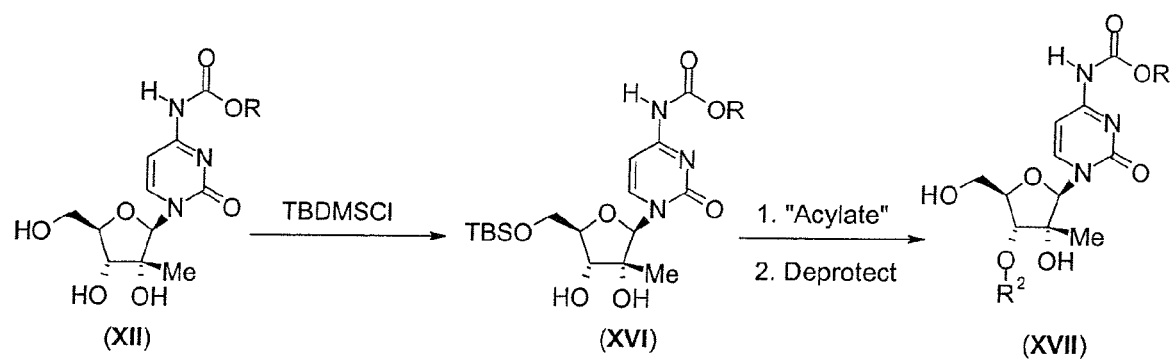
FIG. 5 illustrates a general synthetic route to 3'- and N-4 disubstituted 2'-C-methyl-ribofuranosyl cytidine analogs.

FIG. 5 illustrates a general synthetic route to 2'-C-methyl-ribofuranosyl cytidine analogs substituted at the 3' and N-4 positions. The carbamate nucleoside derivative (XII) is selectively protected at the 5'-hydroxyl (e.g., with tert-butyldimethylsilyl chloride, imidazole) to afford compound (XVI), which may be further reacted with an appropriate acylating, acyloxyalkylcarbonylating, oxycarbonylating, or aminoacylating agent (or substituted variations thereof) and then deprotected (e.g., trifluoroacteic acid or tetra-n-butyl ammonium fluoride) to yield the substituted 2'-C-methyl-ribofuranosyl cytidine analog (XVII).

Figure 6:
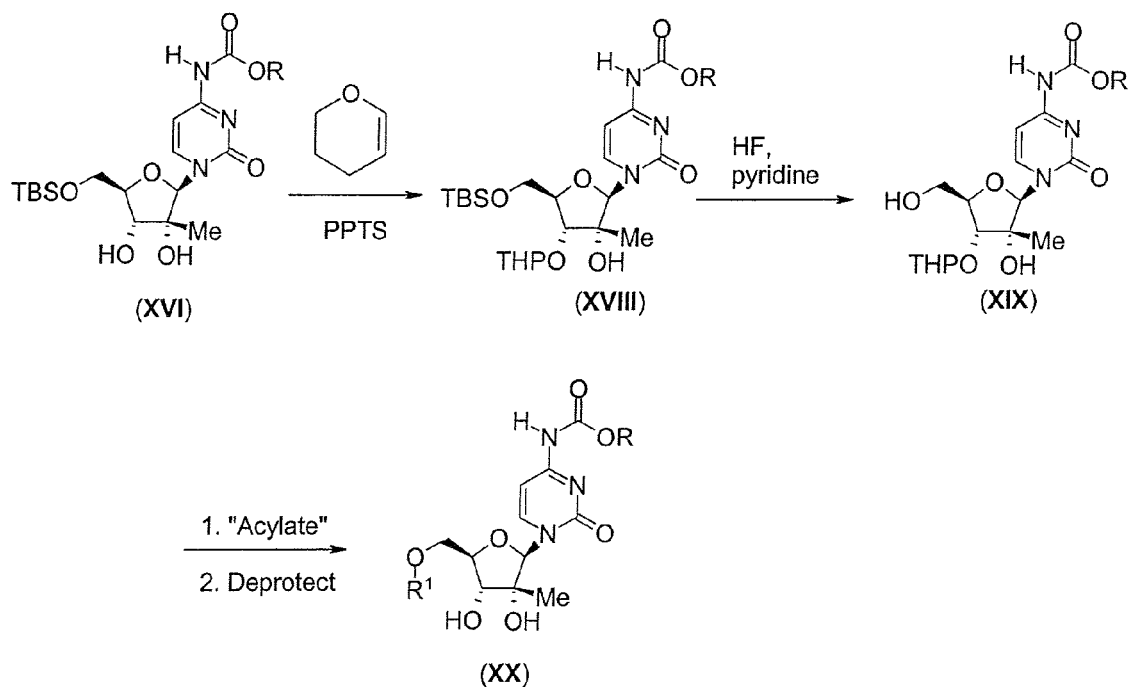
FIG. 6 illustrates a general synthetic route to 5'- and N-4 disubstituted 2'-C-methyl-ribofuranosyl cytidine analogs.

FIG. 6 illustrates a general synthetic route to 2'-C-methyl-ribofuranosyl cytidine analogs substituted at the 5' and N-4 positions. The orthogonally protected nucleoside derivative (XVIII) is prepared from compound (XVI) by treatment with dihydropyran in the presence of an acid catalyst. Selective removal of the 5'-hydroxyl protecting group (e.g., HF, pyridine) to yield (XIX), followed by reaction with a suitable acylating, acyloxyalkylcarbonylating, oxycarbonylating, or aminoacylating agent (or substituted variations thereof and removal of the 3'-hydroxyl protecting group (e.g., gaseous HCl) provides the substituted 2'-C-methyl-ribofuranosyl cytidine analog (XX).

Figure 7:
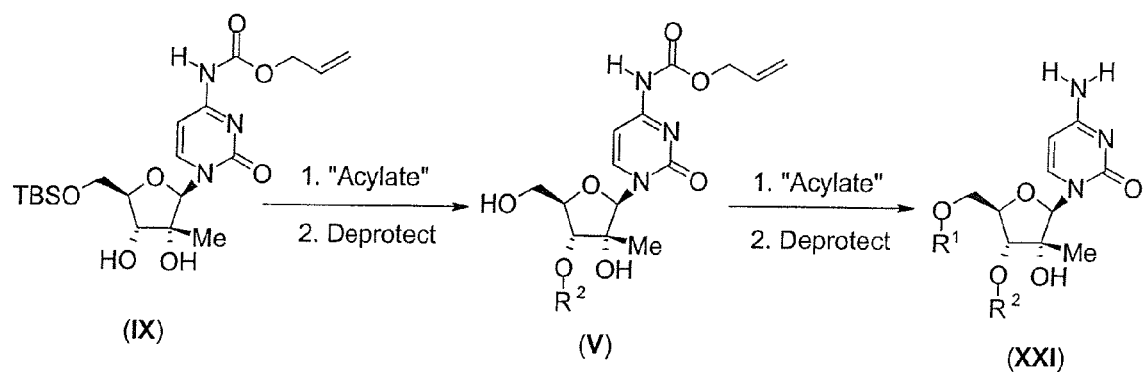
FIG. 7 illustrates a general synthetic route to 3'- and 5'-disubstituted 2'-C-methyl-ribofuranosyl cytidine analogs.

FIG. 7 illustrates a general synthetic route to 2'-C-methyl-ribofuranosyl cytidine analogs selectively substituted at the 3' and 5' positions. Compound (IX) is reacted with a suitable acylating, acyloxyalkylcarbonylating, oxycarbonylating, or aminoacylating agent (or substituted variations thereof) to provide compound (V) after removal of the 5'-hydroxyl protecting group. Further treatment with a suitable acylating, acyloxyalkylcarbonylating, oxycarbonylating, or aminoacylating agent (or substituted variations thereof followed by removal of N-4 protecting group provides the substituted 2'-C-methyl-ribofuranosyl cytidine analog (XXI).

Figure 8:
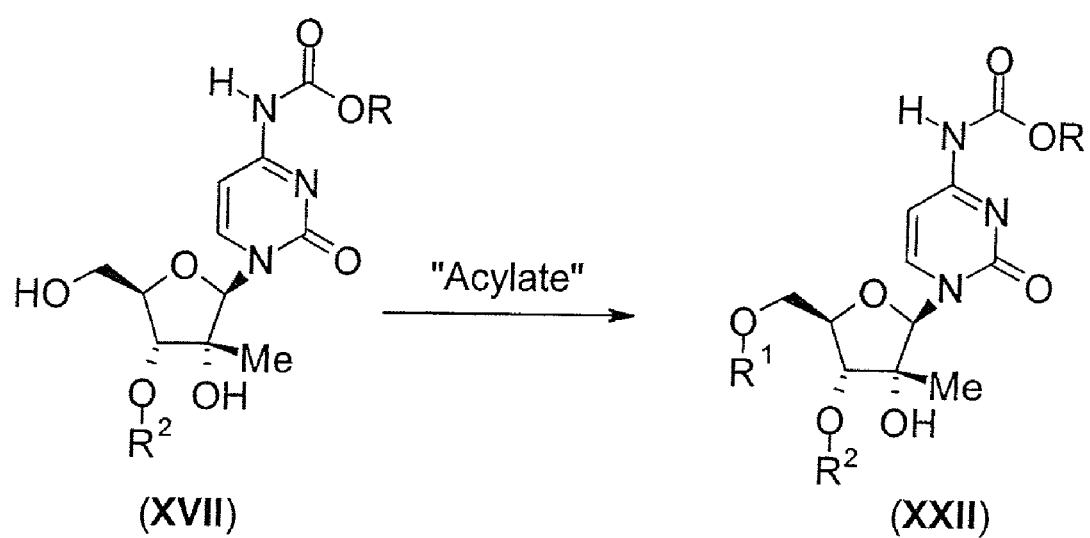
FIG. 8 illustrates a general synthetic route to trisubstituted 2'-C-methyl-ribofuranosyl cytidine analogs.

FIG. 8 illustrates a general synthetic route to 2'-C-methyl-ribofuranosyl cytidine analogs selectively substituted at the 3', 5' and N-4 positions. Disubstituted nucleoside derivative (XVII) is reacted with a suitable acylating, acyloxyalkylcarbonylating, oxycarbonylating, or aminoacylating agent (or substituted variations thereof) to provide the triply substituted 2'-C-methyl-ribofuranosyl cytidine analog (XXII).

Therapeutic Uses

Compounds and pharmaceutical compositions provided by the present disclosure may be used to treat a variety of viral diseases. In certain embodiments, a compound and/or a pharmaceutical composition thereof is administered to a patient, such as a human, suffering from a viral disease.

Patients, including humans, infected with pestivirus, flavivirus, HCV, or another organism replicating through a RNA-dependent RNA viral polymerase, or affected by any other disorder described herein, can be treated by administering to the patient a therapeutically effective amount of a compound of Formula (I) in the presence of a pharmaceutically acceptable carrier or diluent. The active materials may be administered by any appropriate route, for example, orally, parenterally, intravenously, intradermally, subcutaneously, or topically, in liquid or solid form.

Accordingly, it is well with the capability of those of skill in the art to assay and use compounds and/or pharmaceutical compositions thereof provided by the present disclosure to treat the above diseases or disorders.

Therapeutic/Prophylactic Administration

Compounds and/or pharmaceutical compositions thereof provided by the present disclosure may be advantageously used in human medicine. As described herein, compounds and/or pharmaceutical compositions thereof provided by the present disclosure are useful for the treatment of various diseases or disorders.

When used to treat the above disease or disorders compounds and/or compositions may be administered or applied singly, in combination with other agents. The compounds and/or compositions may also be administered or applied singly, in combination with other pharmaceutically active agents, including other compounds.

The current disclosure provides methods of treatment and prophylaxis by administration to a patient of a therapeutically effective amount of a compound or composition. The patient may be an animal, such as a mammal, and in particular a human.

Compounds and/or compositions provided by the present disclosure, which comprise one or more compounds, are preferably administered orally. The compounds and/or compositions may also be administered by any other convenient route, for example, by infusion or bolus injection, by absorption through epithelial or mucocutaneous linings (e.g., oral mucosa, rectal and intestinal mucosa, etc.). Administration can be systemic or local. Various delivery systems are known, (e.g., encapsulation in liposomes, microparticles, microcapsules, capsules, etc.) that can be used to administer a compound and/or composition. Methods of administration include, but are not limited to, intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin.

In certain embodiments, compounds and/or compositions provided by the present disclosure can be delivered via sustained release systems, preferably oral sustained release systems. In certain embodiments, a pump may be used (see Langer, supra; Sefton, 1987, *CRC Crit Ref Biomed Eng.* 14, 201; and Saudek et al., 1989, *N. Engl. J Med.* 321, 574).

In other embodiments, polymeric materials can be used (see "Medical Applications of Controlled Release," Langer and Wise (eds.), CRC Pres., Boca Raton, Fla. (1974); "Controlled Drug Bioavailability," Drug Product Design and Performance, Smolen and Ball (eds.), Wiley, New York (1984); Ranger and Peppas, 1983, *J Macromol. Sci. Rev. Macromol Chem.* 23, 61; see also Levy et al., 1985, *Science* 228, 190; During et al., 1989, *Ann. Neurol.* 25, 351; Howard et al., 1989, *J. Neurosurg.* 71, 105). In certain embodiments, polymeric materials are used for oral sustained release delivery. Examples of useful polymers include sodium carboxymethylcellulose, hydroxypropylcellulose, hydroxypropylmethylcellulose, and hydroxyethylcellulose, and in certain embodiments, hydroxypropylmethylcellulose. Other preferred cellulose ethers have been described (Alderman, *Int. J. Pharm. Tech. & Prod. Mfr.*, 1984, 5(3), 1-9). Factors affecting drug release are well known to the skilled artisan and have been described in the art (Bamba et al., *Int. J. Pharm.*, 1979, 2, 307).

In other embodiments, enteric-coated preparations can be used for oral sustained release administration. Examples of useful coating materials include polymers with a pH-dependent solubility (i.e., pH-controlled release), polymers with a slow or pH-dependent rate of swelling, dissolution or erosion (i.e., time-controlled release), polymers that are degraded by enzymes (i.e., enzyme-controlled release) and polymers that form firm layers that are destroyed by an increase in pressure (i.e., pressure-controlled release).

In still other embodiments, osmotic delivery systems can be used for oral sustained release administration (Verma et al., *Drug Dev. Ind. Pharm.*, 2000, 26, 695-708). In certain embodiments, OROS™ osmotic devices can be used for oral sustained release delivery devices (Theeuwes et al., U.S. Pat. No. 3,845,770; and Theeuwes et al., U.S. Pat. No. 3,916,899).

In yet other embodiments, a controlled-release system can be placed in proximity of the target of a compounds and/or compositions thereof provided by the present disclosure, thus requiring only a fraction of the systemic dose (see, e.g., Goodson, in "Medical Applications of Controlled Release," supra, vol. 2, pp. 115-138 (1984)). Other controlled-release systems discussed in Langer, 1990, *Science* 249, 1527-1533 may also be used.

Compounds and/or compositions provided by the present disclosure provide □-D-2'-C-methyl-ribofuranosyl cytidine upon in vivo administration to a patient. The promoiety or promoieties of the compounds may be cleaved either chemically and/or enzymatically. One or more enzymes present in the stomach, intestinal lumen, intestinal tissue, blood, liver, brain or any other suitable tissue of a mammal may enzymatically cleave the promoiety or promoieties of the compounds. As orally administered NM 283 (2) is known to cause gastrointestinal side-effects (e.g., nausea, vomiting, diarrhea) it is preferred that β-D-2'-C-methyl-ribofuranosyl cytidine prodrugs are absorbed across the GI mucosa largely intact before being converted to the active antiviral drug within the liver, blood, plasma, brain, or any other suitable tissue of the subject.

If the promoiety or promoieties of compounds provided by the present disclosure are cleaved after absorption by the gastrointestinal tract, these 2'-C-methyl-ribofuranosyl cytidine analogs may have the opportunity to be absorbed into the systemic circulation from the large intestine. In this situation, the compounds and/or compositions may be administered as sustained release systems. In certain embodiments, the compounds and/or compositions are delivered by oral sustained release administration. Delivery from a sustained release system may allow the drug to be administered in such a way that reduces the side-effect profile associated with high peak plasma concentrations of the drug following bolus injection. In certain embodiments, compounds and/or compositions provided by the present disclosure are administered no more than once per day.

Pharmaceutical Compositions

Pharmaceutical compositions provided by the present disclosure typically contain a therapeutically effective amount of one or more compounds provided by the present disclosure, preferably in purified form, together with a suitable amount of a pharmaceutically acceptable vehicle, so as to provide the form for proper administration to a patient. When administered to a patient, the compounds and pharmaceutically acceptable vehicles are preferably sterile. Water is a preferred vehicle when the compound is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Pharmaceutical compositions provided by the present disclosure, if desired, can also contain minor amounts of wetting or emulsifying agents, and/or pH buffering agents. In addition, auxiliary, stabilizing, thickening, lubricating, and/or coloring agents may be used.

Pharmaceutical compositions comprising a compound provided by the present disclosure may be manufactured by means of conventional mixing, dissolving, granulating, dragee-making, levigating, emulsifying, encapsulating, entrapping, or lyophilizing processes. Pharmaceutical compositions may be formulated in conventional manner using one or more physiologically acceptable carriers, diluents, excipients, and/or auxiliaries, which facilitate processing of compounds into preparations, which can be used pharmaceutically. Proper formulation is dependent upon the route of administration chosen.

Present pharmaceutical compositions provided by the present disclosure can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In certain embodiments, a pharmaceutically acceptable form is a capsule (see e.g., Grosswald et al., U.S. Pat. No. 5,698,155). Other examples of suitable pharmaceutical forms have been described in the art (see Remington's Pharmaceutical Sciences, Philadelphia College of Pharmacy and Science, 17th Edition, 1985).

For topical administration a compound provided by the present disclosure may be formulated as solutions, gels, ointments, creams, suspensions, etc. as is well-known in the art. For transmucosal administration, penetrants appropriate to the barrier to be permeated are used in the formulation. Such penetrants are generally known in the art. Systemic formulations include those designed for administration by injection, e.g., subcutaneous, intravenous, intramuscular, intrathecal, or intraperitoneal injection, as well as those designed for transdermal, transmucosal, oral or pulmonary administration. Systemic formulations may be made in combination with a further active agent that improves mucociliary clearance of airway mucus or reduces mucous viscosity. Examples of active agents that improve mucociliary clearance of airway mucus or reduce mucous viscosity include, but are not limited to, sodium channel blockers, antibiotics, N-acetyl cysteine, homocysteine, and phospholipids.

Pharmaceutical compositions for oral delivery may be in the form of tablets, lozenges, aqueous or oily suspensions, granules, powders, emulsions, capsules, syrups, or elixirs, for example. Orally administered pharmaceutical compositions may contain one or more optional agents, for example, sweetening agents such as fructose, aspartame or saccharin; flavoring agents such as peppermint, oil of wintergreen, or cherry coloring agents and preserving agents, to provide a pharmaceutically palatable preparation. Moreover, when in tablet or pill form, a pharmaceutical composition may be coated to delay disintegration and absorption in the gastrointestinal tract, thereby providing a sustained action over an extended period of time. Selectively permeable membranes surrounding an osmotically active driving compound are also suitable for orally administered compounds. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

For oral liquid preparations such as, for example, suspensions, elixirs and solutions, suitable carriers, excipients or diluents include water, saline, alkyleneglycols (e.g., propylene glycol), polyalkylene glycols (e.g., polyethylene glycol) oils, alcohols, slightly acidic buffers between pH 4 and pH 6 (e.g., acetate, citrate, ascorbate at between about 5.0 mM to about 50.0 mM), etc. Additionally, flavoring agents, preservatives, coloring agents, bile salts, acylcarnitines and the like may be added.

For buccal administration, the pharmaceutical compositions may take the form of tablets, lozenges, etc. formulated in conventional manner.

In addition to the formulations described, a compound may also be formulated as a depot preparation. Such long acting formulations may be administered by implantation (for example subcutaneously or intramuscularly) or by intramuscular injection. Thus, for example, a compound may be formulated with suitable polymeric or hydrophobic materials (for example as an emulsion in an acceptable oil) or ion exchange resins, or as sparingly soluble derivatives, for example, as a sparingly soluble salt.

When a compound is acidic or basic, it may be included in any of the above-described formulations as the free acid or free base, a pharmaceutically acceptable salt, a solvate, or hydrate. Pharmaceutically acceptable salts substantially retaining the activity of the free acid or base may be prepared by reaction with bases or acids and tend to be more soluble in aqueous and other protic solvents than the corresponding free acid or base form.

Therapeutic Doses

Compounds and/or pharmaceutical compositions provided by the present disclosure will generally be used in an amount effective to achieve the intended purpose. For use to treat the above diseases or disorders the compounds and/or pharmaceutical compositions thereof, are administered or applied in a therapeutically effective amount.

In certain embodiments, a dose of a compound of Formula (I) for treatment of infection with a pestivirus, flavivirus, or HCV will be in the range from about 1 to about 100 mg/kg of body weight per day, in certain embodiments, from about 1 to about 20 mg/kg of body weight per day, and in certain embodiments, from about 0.1 to about 100 mg per kilogram body weight per day. Lower doses may also be therapeutically effective, for example doses ranging from about 0.5 to about 100 mg, from about 0.5 to about 50 mg, from about 0.5 to about 10 mg, and in certain embodiments from about 0.5 to about 5 mg per kilogram body weight per day. Even lower doses may be useful, and thus for example, can range from about 0.1 to about 0.5 mg per kilogram body weight per day. The effective dosage range of pharmaceutically acceptable salts and prodrugs can be calculated based on the weight of the parent nucleoside to be delivered. If the salt or prodrug exhibits activity in itself, the effective dosage can be estimated as above using the weight of the salt or prodrug, or by other means known to those skilled in the art.

Compounds and pharmaceutical compositions provided by the present disclosure can be conveniently administered in unit any suitable dosage form, including but not limited to one containing about 7 to about 3000 mg, and in certain embodiments about 70 to about 1400 mg of active agent per unit dosage form. In certain embodiments, an oral dosage form containing from about 50 to about 1000 mg of the active agent is convenient, included in one or multiple dosage forms containing 50, 100, 200, 250, 300, 400, 500, 600, 700, 800, 900, or 1000 mg of active agent. Lower doses may also be used, for example from about 10 to about 100, and from about 1 to about 50 mg of active agent per unit dosage form. Also contemplated are doses of about 0.1 to about 50 mg, from about 0.1 to about 20 mg, and in certain embodiments, from about 0.1 to about 10.0 mg of active agent per unit dosage from. Furthermore, lower doses may be utilized in the case of administration by a non-oral route, as, for example, by injection or inhalation.

Ideally the active agent should be administered at a dose sufficient to achieve peak plasma concentrations of the active agent from about 0.2 to about 70 μM, and in certain embodiments, from about 1.0 to about 10 μM.

The appropriate concentration of active compound in a pharmaceutical composition provided by the present disclosure will depend on absorption, inactivation, and excretion rates of the drug as well as other factors known to those of skill in the art. It is to be noted that dosage values will also vary with the severity of the condition to be alleviated. It is to be further understood that for any particular patient, specific dosage regimens may be adjusted over time according to the individual need and the professional judgment of the person administering or supervising the administration of the compositions, and that the concentration ranges set forth herein are exemplary only and are not intended to limit the scope or practice of the claimed compositions. The active agents may be administered at once, or may be divided into a number of smaller doses to be administered at varying intervals of time, with or without other anti-viral agents.

A preferred mode of administration of the active compound is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

In certain embodiments, a therapeutically effective dose of a compound provided by the present disclosure and/or pharmaceutical composition thereof will provide therapeutic benefit without causing substantial toxicity. Toxicity of compounds provided by the present disclosure and/or pharmaceutical compositions thereof may be determined using standard pharmaceutical procedures and may be readily ascertained by the skilled artisan. The dose ratio between toxic and therapeutic effect is the therapeutic index. A compound and/or pharmaceutical composition thereof will preferably exhibit particularly high therapeutic indices in treating disease and disorders. The dosage of a compound provided by the present disclosure and/or pharmaceutical composition thereof described herein will preferably be within a range of circulating concentrations that include an effective dose with minimal toxicity. β-D-2'-C-Methyl-ribofuranosyl cytidine may exert toxic effects on the gastrointestinal tract via accumulation as the cytotoxic triphosphate metabolite within enterocytes. Oral administration of a β-D-2'-C-methyl-ribofuranosyl cytidine prodrug that is substantially stable within enterocytes, but which is capable of conversion to the parent drug following absorption can reduce intestinal cell exposure to β-D-2'-C-methyl-ribofuranosyl cytidine.

Combination Therapy

In certain embodiments provided by the present disclosure, the compounds and/or pharmaceutical compositions thereof can be used in combination therapy with at least one other therapeutic agent. A compound provided by the present disclosure and/or pharmaceutical composition thereof and the additional therapeutic agent can act additively or, in certain embodiments, synergistically. In certain embodiments, a compound and/or a pharmaceutical composition thereof is administered concurrently with the administration of another therapeutic agent. In other embodiments, a compound and/or pharmaceutical composition thereof is administered prior or subsequent to administration of another therapeutic agent.

Compounds provided by the present disclosure can be administered in combination or in alternation with another anti-flavivirus or pestivirus agent, or in particular an anti-HCV agent. In combination therapy, effective dosages of two or more agents are administered together, whereas in alternation or sequential-step therapy, an effective dosage of each agent is administered serially or sequentially. The dosages given will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions. Appropriate second antiviral agents may be selected from interferon, ribavirin, interleukin, an NS3 protease inhibitor, cysteine protease inhibitor, thiazolidine derivative, thiazolidine, benzanilide, phenanthrenequinone, a helicase inhibitor, a polymerase inhibitor, a nucleotide analogue, gliotoxin, cerulenin, antisense phosphorothioate oligodeoxynucleotides, inhibitor of IRES-dependent translation, and a ribozyme. In preferred embodiments, an anti-HCV (or anti-pestivirus or anti-flavivirus) compound that exhibits an $EC_{50}$ of about 10 to about 15 μM, and in certain embodiments less than about 1 to about 5 μM, is desirable.

It has been recognized that drug-resistant variants of flaviviruses, pestiviruses, or HCV can emerge after prolonged treatment with an antiviral agent. Drug resistance most typically occurs by mutation of a gene that encodes for an enzyme used in viral replication. The efficacy of a drug against the viral infection can be prolonged, augmented, or restored by administering a compound provided by the present disclosure in combination or alternation with a second, and perhaps third, antiviral compound that induces a different mutation from that caused by the principle drug. Alternatively, the pharmacokinetics, biodistribution, or other parameters of a compound of the present disclosure can be altered by such combination or alternation therapy. In general, combination therapy is preferred over alternation therapy because it induces multiple simultaneous stresses on the virus.

EXAMPLES

Reference is now made to the following examples, which describe in detail preparation of compounds and methods for assaying for biological activity. It will be apparent to those skilled in the art that many modifications, both to materials and methods, may be practiced without departing from the scope of the disclosure.

Example 1

Compound Synthesis

Following the protocols disclosed in U.S. Application Publication No. 2004/0142857, the following compounds are synthesized:

β-1-(4-allyloxycarbonylamino-2-oxo-1H-pyrimidin-1-yl)-2-C-methyl-ribofuranose;

β-1-(4-benzyloxycarbonylamino-2-oxo-1H-pyrimidin-1-yl)-2-C-methyl-ribofuranose;

β-1-(4-ethoxycarbonylamino-2-oxo-1H-pyrimidin-1-yl)-2-C-methyl-ribofuranose;

β-1-(4-ethoxycarbonylamino-2-oxo-1H-pyrimidin-1-yl)-5-O-(tert-butyldimethylsilyl)-2-C-methyl-ribofuranose;

β-1-(4-ethoxycarbonylamino-2-oxo-1H-pyrimidin-1-yl)-3-O-(N-tert-butyloxycarbonyl-L-valinyl)-5-O-(tert-butydimethylsilyl)-2-C-methyl-ribofuranose;

β-1-(4-ethoxycarbonylamino-2-oxo-1H-pyrimidin-1-yl)-3-O-(L-valinyl)-2-C-methyl-ribofuranose;

β-1-(4-ethoxycarbonylamino-2-oxo-1H-pyrimidin-1-yl)-3-O-(tetrahydropyranyl)-5-O-(tert-butyldimethylsilyl)-2-C-methyl-ribofuranose;

β-1-(4-ethoxycarbonylamino-2-oxo-1H-pyrimidin-1-yl)-3-O-(tetrahydropyranyl)-2-C-methyl-ribofuranose;

β-1-(4-ethoxycarbonylamino-2-oxo-1H-pyrimidin-1-yl)-3-O-(tetrahydropyranyl)-5-O-(N-tert-butoxycarbonyl-L-valinyl)-2-C-methyl-ribofuranose;

β-1-(4-ethoxycarbonylamino-2-oxo-1H-pyrimidin-1-yl)-5-O-(L-valinyl)-2-C-methyl-ribofuranose;

β-1-(4-allyloxycarbonylamino-2-oxo-1H-pyrimidin-1-yl)-5-O-(tert-butyldimethylsilyl)-2-C-methyl-ribofuranose;

β-1-(4-Pentyloxycarbonylamino-2-oxo-1H-pyrimidin-1-yl)-2-C-methyl-ribofuranose;

β-1-(4-Amino-2-oxo-1H-pyrimidin-1-yl)-5-O-(pentyloxycarbonyl)-2-C-methyl-ribofuranose;

β1-(4-Amino-2-oxo-1H-pyrimidin-1-yl)-3-O-(pentyloxycarbonyl)-2-C-methyl-ribofuranose;

β-1-(4-Pentyloxycarbonylamino-2-oxo-1H-pyrimidin-1-yl)-3-O-(pentyloxycarbonyl)-2-C-methyl-ribofuranose;

β-1-(4-Pentyloxycarbonylamino-2-oxo-1H-pyrimidin-1-yl)-5-O-(pentyloxycarbonyl)-2-C-methyl-ribofuranose;

β-1-(4-Amino-2-oxo-1H-pyrimidin-1-yl)-3-O-(pentyloxycarbonyl)-5-O-(pentyloxycarbonyl)-2-C-methyl-ribofuranose;

β-1-(4-Pentyloxycarbonylamino-2-oxo-1H-pyrimidin-1-yl)-3-O-(pentyloxycarbonyl)-5-O-(pentyloxycarbonyl)-2-C-methyl-ribofuranose;

β-1-(4-amino-2-oxo-1H-pyrimidin-1-yl)-3,5-O-di-(tert-butyldimethylsilyl)-2-C-methyl-ribofuranose;

β-1-(4-Phenyloxycarbonylamino-2-oxo-1H-pyrimidin-1-yl)-2-C-methyl-ribofuranose;

β-1-(4-(4-Methoxyphenyl)oxycarbonylamino-2-oxo-1H-pyrimidin-1-yl)-2-C-methyl-ribofuranose;

β-1-(4-(1,1,1-Trifluoroethyl)oxycarbonylamino-2-oxo-1H-pyrimidin-1-yl)-2-C-methyl-ribofuranose;

β-1-(4-(4-Methoxybenzyl)oxycarbonylamino-2-oxo-1H-pyrimidin-1-yl)-2-C-methyl-ribofuranose;

β-1-(4-(Propen-2-yl)oxycarbonylamino-2-oxo-1H-pyrimidin-1-yl)-2-C-methyl-ribofuranose;

β-1-(4-(2-Carboxy-2-methyl)ethoxycarbonylamino-2-oxo-1H-pyrimidin-1-yl)-2-C-methyl-ribofuranose;

β-1-(4-Pentyloxycarbonylamino-2-oxo-1H-pyrimidin-1-yl)-5-O-acetyl-2-C-methyl-ribofuranose;

β-1-(4-Pentyloxycarbonylamino-2-oxo-1H-pyrimidin-1-yl)-3-O-acetyl-2-C-methyl-ribofuranose;

β-1-(4-Acetoxymethoxycarbonylamino-2-oxo-1H-pyrimidin-1-yl)-2-C-methyl-ribofuranose;

β-1-(4-(1-Isobutanoyloxyethoxy)carbonylamino-2-oxo-1H-pyrimidin-1-yl)-2-C-methyl-ribofuranose;

β-1-(4-(2,6-Dimethylbenzoyl)oxymethoxycarbonylamino-2-oxo-1H-pyrimidin-1-yl)-2-C-methyl-ribofuranose;

β-1-(4-(2-Methylbenzoyl)oxymethoxycarbonylamino-2-oxo-1H-pyrimidin-1-yl)-2-C-methyl-ribofuranose;

β-1-(4-Acetoxymethoxycarbonylamino-2-oxo-1H-pyrimidin-1-yl)-5-O-(L-valinyl)-2-C-methyl-ribofuranose;

β-1-{[4-((2S)-((2S)-Aminopropionylamino)-2-carboxy)ethoxycarbonylamino]-2-oxo-1H-pyrimidin-1-yl}-2-C-methyl-ribofuranose;

β-1-{[4-((2S)-((2S)-Amino-3,3-dimethylbutyroylamino)-2-carboxy)ethoxycarbonylamino]-2-oxo-1H-pyrimidin-1-yl}-2-C-methyl-ribofuranose;

β-1-{[4-((2S)-(Aminoacetylamino)-2-carboxy)ethoxycarbonylamino]-2-oxo-1H-pyrimidin-1-yl}-2-C-methyl-ribofuranose;

β-1-{[4-((2S)-((2S)-Aminophenacetylamino)-2-carboxy)ethoxycarbonylamino]-2-oxo-1H-pyrimidin-1-yl}-2-C-methyl-ribofuranose;

β-1-{[4-((2S)-(2-Amino-2-methylpropionylamino)-2-carboxy)ethoxycarbonylamino]-2-oxo-1H-pyrimidin-1-yl}-2-C-methyl-ribofuranose;

β-1-{[4-((2S)-(1-Amino-cyclohexanecarbonylamino)-2-carboxy)ethoxycarbonylamino]-2-oxo-1H-pyrimidin-1-yl}-2-C-methyl-ribofuranose;

β-1-(4-(2-Acetoxyethoxy)carbonylamino-2-oxo-1H-pyrimidin-1-yl)-2-C-methyl-ribofuranose;

β-1-(4-(2-Pivaloyloxyethoxy)carbonylamino-2-oxo-1H-pyrimidin-1-yl)-2-C-methyl-ribofuranose;

β-1-(4-(2-Cyclohexanecarboxyethoxy)carbonylamino-2-oxo-1H-pyrimidin-1-yl)-2-C-methyl-ribofuranose;

β-1-{[4-(2-((2S)-Amino-3-methylbutyroylamino)-ethoxycarbonylamino]-2-oxo-1H-pyrimidin-1-yl}-2-C-methyl-ribofuranose;

β-1-{[4-(2-((2S)-Amino-3-phenylpropionylamino)-ethoxycarbonylamino]-2-oxo-1H-pyrimidin-1-yl}-2-C-methyl-ribofuranose;

β-1-{[4-(2-(Phenyloxycarbonylamino)-ethoxycarbonylamino]-2-oxo-1H-pyrimidin-1-yl}-2-C-methyl-ribofuranose;

β-1-{[4-(3-(Benzyloxycarbonylamino)-propoxycarbonylamino]-2-oxo-1H-pyrimidin-1-yl}-2-C-methyl-ribofuranose;

β-1-[4-(2-Dimethylamino-ethoxycarbonylamino)-2-oxo-1H-pyrimidin-1-yl]-2-C-methyl-ribofuranose;

β-1-[4-(4-Acetoxybutyroylamino)-2-oxo-1H-pyrimidin-1-yl]-2-C-methyl-ribofuranose;

β-1-[4-(4-Pivaloyloxybutyroylamino)-2-oxo-1H-pyrimidin-1-yl]-2-C-methyl-ribofuranose;

β-1-{[4-(2-((1-Pivaloyloxy-2,2-dimethylpropyl)oxycarbonylamino)-ethoxycarbonylamino]-2-oxo-1H-pyrimidin-1-yl}-2-C-methyl-ribofuranose;

β-1-{[4-(2-((Isobutanoyloxymethyl)oxycarbonylamino)-ethoxycarbonylamino]-2-oxo-1H-pyrimidin-1-yl}-2-C-methyl-ribofuranose;

β-1-{[4-(2-((Acetoxymethyl)oxycarbonylamino)-ethoxycarbonylamino]-2-oxo-1H-pyrimidin-1-yl}-2-C-methyl-ribofuranose;

β-1-{[4-(2-((1-Isobutanoyloxyethyl)oxycarbonylamino)-ethoxycarbonylamino]-2-oxo-1H-pyrimidin-1-yl}-2-C-methyl-ribofuranose;

β-1-{[4-(2-((1-Acetoxy-2-methylpropyl)oxycarbonylamino)-ethoxycarbonylamino]-2-oxo-1H-pyrimidin-1-yl}-2-C-methyl-ribofuranose;

β-1-{[4-(2-((1-Isobutanoyloxy-2-methylpropyl)oxycarbonylamino)-ethoxycarbonylamino]-2-oxo-1H-pyrimidin-1-yl}-2-C-methyl-ribofuranose;

β-1-{[4-(2-((1-Pivaloyloxy-2-methylpropyl)oxycarbonylamino)-ethoxycarbonylamino]-2-oxo-1H-pyrimidin-1-yl}-2-C-methyl-ribofuranose;

β-1-{[4-(2-((1-Pivaloyloxyethyl)oxycarbonylamino)-ethoxycarbonylamino]-2-oxo-1H-pyrimidin-1-yl}-2-C-methyl-ribofuranose;

β-1-{[4-(2-((1-Acetoxyethyl)oxycarbonylamino)-ethoxycarbonylamino]-2-oxo-1H-pyrimidin-1-yl}-2-C-methyl-ribofuranose;

β-1-{[4-(2-((Acetoxymethyl)oxycarbonylmethylamino)-ethoxycarbonylamino]-2-oxo-1H-pyrimidin-1-yl}-2-C-methyl-ribofuranose;

β-1-{[4-(2-((1-Isobutanoyloxyethyl)oxycarbonylmethylamino)-ethoxycarbonylamino]-2-oxo-1H-pyrimidin-1-yl}-2-C-methyl-ribofuranose;

β-1-{[4-(2-((1-Acetoxy-2-methylpropyl)oxycarbonylmethylamino)-ethoxycarbonylamino]-2-oxo-1H-pyrimidin-1-yl}-2-C-methyl-ribofuranose;

β-1-{[4-(2-((1-Isobutanoyloxy-2-methylpropyl)oxycarbonylmethylamino)-ethoxycarbonylamino]-2-oxo-1H-pyrimidin-1-yl}-2-C-methyl-ribofuranose;

β-1-{[4-(2-((1-Pivaloyloxy-2-methylpropyl)oxycarbonylmethylamino)-ethoxycarbonylamino]-2-oxo-1H-pyrimidin-1-yl}-2-C-methyl-ribofuranose;

β-1-{[4-(2-((1-Pivaloyloxyethyl)oxycarbonylmethylamino)-ethoxycarbonylamino]-2-oxo-1H-pyrimidin-1-yl}-2-C-methyl-ribofuranose;

β-1-{[4-(2-((1-Acetoxyethyl)oxycarbonylmethylamino)-ethoxycarbonylamino]-2-oxo-1H-pyrimidin-1-yl}-2-C-methyl-ribofuranose;

β-1-{[4-(2-((1-(2,6-Dimethylbenzoyl)oxymethyl)oxycarbonylmethylamino)-ethoxycarbonylamino]-2-oxo-1H-pyrimidin-1-yl}-2-C-methyl-ribofuranose;

β-1-{[4-(2-((1-(2,6-Dimethylbenzoyl)oxy-2-methylpropyl)oxycarbonylmethylamino)-ethoxycarbonylamino]-2-oxo-1H-pyrimidin-1-yl}-2-C-methyl-ribofuranose; and β-1-{[4-(2-((1-(2-Methylbenzoyl)oxy-2-methylpropyl)oxycarbonylmethylamino)-ethoxycarbonylamino]-2-oxo-1H-pyrimidin-1-yl}-2-C-methyl-ribofuranose.

Example 2

In Vitro Compound Transport Assays With PEPT1 and PEPT2-Expressing Cell Lines (a) Inhibition of Radiolabeled Gly-Sar Uptake Rat and human PEPT1 and PEPT2 expressing CHO cell lines are prepared as described in International Application WO 2001/20331. Amino acid ester conjugates of β-D-2'-C-methyl-ribofuranosyl cytidine are evaluated for interaction with the peptide transporters using a radiolabeled substrate uptake assay in a competitive inhibition format, as described in International Publication No. WO 2001/20331. Transport-induced currents are also measured in *Xenopus* oocytes transfected with rat and human PEPT1 and PEPT2.

(b) Analysis of Electrogenic Transport in *Xenopus* Oocytes

RNA preparation: Rat and human PEPT1 and PEPT2 transporter cDNAs are subcloned into a modified pGEM plasmid that contains 5' and 3' untranslated sequences from the *Xenopus* ☐ actin gene. These sequences increase RNA stability and protein expression. Plasmid cDNA is linearized and used as a template for in vitro transcription (Epicentre Technologies transcription kit, 4:1 methylated:non-methylated GTP).

*Xenopus* oocyte isolation. *Xenopus laevis* frogs are anesthetized by immersion in Tricaine (1.5 g/mL in deionized water) for 15 minutes. Oocytes are removed and digested in frog Ringer solution (90 mM NaCl, 2 mM KCl, 1 mM $MgCl_2$, 10 mM NaHEPES, pH 7.45, no $CaCl_2$) with 1 mg/mL collagenase (Worthington Type 3) for 80-100 minutes with shaking. The oocytes are washed 6 times, and the buffer changed to frog Ringer solution containing $CaCl_2$ (1.8 mM). Remaining follicle cells are removed if necessary. Cells are incubated at 16° C., and each oocyte injected with 10-20 µg RNA in 45 µL of solution.

Electrophysiology measurements. Transport currents are measured 1-4 days after injection, using a standard two-electrode electrophysiology set-up (Geneclamp 500 amplifier, Digidata 1320/PCLAMP software and ADInstruments hardware and software are used for signal acquisition). Electrodes (2-4 mΩ) are microfabricated using a Sutter Instrument puller and filled with 3M KCl. The bath is directly grounded (transporter currents are less than 0.3 µA). Bath flow is controlled by an automated perfusion system (ALA Scientific Instruments, solenoid valves).

For transporter pharmacology, oocytes are clamped at −60 to −90 mV, and continuous current measurements acquired using PowerLab Software and an ADInstruments digitizer. Current signals are low pass filtered at 20 Hz and acquired at 4-8 Hz. All bath and drug-containing solutions are frog Ringers solution containing $CaCl_2$. Drugs are applied for 10-30 seconds until the induced current reaches a new steady-state level, followed by a control solution until baseline currents return to levels that preceded drug application. The difference current (baseline subtracted from peak current during drug application) reflects the net movement of charge resulting from electrogenic transport and is directly proportional to transport rate. Recordings are made from a single oocyte for up to 60 minutes, enabling 30-40 separate compounds to be tested per oocyte. Compound-induced currents are saturable and gave half-maximal values at substrate concentrations comparable to radiolabel competition experiments. To compare results between oocytes expressing different levels of transport activity, a saturating concentration of glycyl-sarcosine (1 mM) is used as a common reference to normalize results from test compounds. Using this normalization procedure $I_{max}$ (i.e. maximal induced current) for different compounds tested on different oocytes can be compared.

Preferred compounds elicit PEPT-specific currents significantly above background (at least 1% of $I_{max}$ for Gly-Sar) when tested at 1 mM on oocytes expressing either PEPT1 or PEPT2, confirming that these compounds serve as substrates for one or both of these transporters.

Example 3

In Vitro Compound Transport Assays with CNT1, CNT2, CNT3, ENT1 and ENT2 Expressing Cells (a) Analysis of Electrogenic Transport in *Xenopus* Oocytes RNA preparation: Human CNT1, CNT2 and CNT3 transporter cDNAs are subcloned into a modified pGEM plasmid that contains 5' and 3' untranslated sequences from the *Xenopus* actin gene. These sequences increase RNA stability and protein expression. Plasmid cDNA is linearized and used as template for in vitro transcription (Epicentre Technologies transcription kit, 4:1 methylated:non-methylated GTP).

*Xenopus* oocyte isolation. *Xenopus laevis* frogs are anesthetized by immersion in Tricaine (1.5 g/mL in deionized water) for 15 minutes. Oocytes are removed and digested in frog Ringer solution (90 mM NaCl, 2 mM KCl, 1 mM $MgCl_2$, 10 mM NaHEPES, pH 7.45, no $CaCl_2$) with 1 mg/mL collagenase (Worthington Type 3) for 80-100 minutes with shaking. The oocytes are washed 6 times, and the buffer changed to frog Ringer solution containing $CaCl_2$ (1.8 mM). Remaining follicle cells are removed if necessary. Cells are incubated at 16° C., and each oocyte injected with 10-20 µg RNA in 45 µL of solution.

Electrophysiology measurements. Transport currents are measured 1-4 days after injection, using a standard two-electrode electrophysiology set-up (Geneclamp 500 amplifier, Digidata 1320/PCLAMP software and ADInstruments hardware and software are used for signal acquisition). Electrodes (2-4 mΩ) are microfabricated using a Sutter Instrument puller and filled with 3M KCl. The bath is directly grounded (transporter currents are less than 0.3 µA). Bath flow is controlled by an automated perfusion system (ALA Scientific Instruments, solenoid valves).

For transporter pharmacology, oocytes are clamped at −60 to −90 mV, and continuous current measurements acquired using PowerLab Software and an ADInstruments digitizer. Current signals are low pass filtered at 20 Hz and acquired at 4-8 Hz. All bath and drug-containing solutions are frog Ringers solution containing $CaCl_2$. Drugs are applied for 10-30 seconds until the induced current reaches a new steady-state level, followed by a control solution until baseline currents return to levels that preceded drug application. The difference current (baseline subtracted from peak current during drug application) reflects the net movement of charge resulting from electrogenic transport and is directly proportional to transport rate. Recordings are made from a single oocyte for up to 60 minutes, enabling 30-40 separate compounds to be tested per oocyte. Compound-induced currents are saturable and gave half-maximal values at substrate concentrations comparable to radiolabel competition experiments. To compare results between oocytes expressing different levels of transport activity, a saturating concentration of uridine or guanosine (1 mM) is used as a common reference to normalize results from test compounds. Using this normalization procedure $I_{max}$ (i.e. maximal induced current) for different compounds tested on different oocytes could be compared. Compound-induced currents are determined to be specific by comparing responses to those observed in the absence of $Na^+$ (required for CNT transport) or in control oocytes not expressing a CNT transporter. Preferred compounds elicit CNT1 and/or CNT3-specific currents significantly above background (at least 5% of $I_{max}$ for uridine) when tested at 1 mM on oocytes expressing either CNT1 or CNT3, confirming that these compounds serve as substrates for one or both of these transporters.

(b) Mass Spectroscopy Analysis of Active Transport of Compounds Into Oocytes Expressing CNT1, CNT2, CNT3, ENT1 or ENT2

Transporters are expressed in oocytes as described above (a). Experiments are performed 3-5 days following injection. Oocytes are incubated with 0.1-3 mM of compounds for 10-30 minutes in frog Ringers solution (90 mM NaCl, 2 mM KCl, 1 mM $MgCl_2$, 2 mM $CaCl_2$, 10 mM NaHEPES, pH 7.45, and 1% BSA). Experiments are performed at room temperature. For each compound, 4-7 oocytes are incubated for each transporter or non-expressing control. Following incubation, oocytes are rapidly washed 4 times in frog Ringers solution, and placed one oocyte per well in a 96 well plate. Oocytes are homogenized in 0.15 mL solution containing 50% ethanol:

water or 50% methanol:water. Precipitated protein or cellular matter is pelleted by spinning plates at 3000 RPM for 5 minutes. The solvent layer containing the extracted compounds is removed from the wells.

The concentration of each compound in the oocyte extract is determined by analytical LC/MS/MS. Briefly, concentrations of test compound are determined using an API 2000 LC/MS/MS instrument equipped with an Agilent 1100 binary pump and a CTC HTS-PAL autosampler. The column is a Phenomenex hydro-RP 4.6×50 mm column. The mobile phase is water with 0.1% formic acid, 0.005% heptafluorobutyric acid (A) and acetonitrile with 0.1% formic acid, 0.005% heptafluorobutyric acid (B). The gradient condition is: 5% B for 0.5 min, then to 95% B in 2.5 min, then maintained at 95% B for 1 min. The mobile phase is returned to 5% B for 2 min. A TurbolonSpray source is used on the API 2000. The analysis is done in positive ion mode and an MRM transition of each analyte is first optimized using the standard solution. 10 µL of the samples are injected onto LC/MS/MS system for analysis. The peaks are integrated using Analyst 1.2 quantification software. Specific uptake is determined by comparison of average uptake in oocytes expressing transporters with uptake in non-expressing oocytes. Significant uptake over background into cells expressing ENT1, ENT2, CNT1, or CNT3 are observed for preferred compounds.

Example 4

Standard Methods for Determination of Enzymatic Cleavage of Prodrugs in Vitro

The stability of β-D-2'-C-methyl-ribofuranosyl cytidine prodrugs is evaluated in one or more in vitro systems using a variety of tissue preparations following methods known in the art. Tissues are obtained from commercial sources (e.g., Pel-Freez Biologicals, Rogers, Ariz., or GenTest Corporation, Woburn, Mass.). Experimental conditions used for the in vitro studies are described in Table 1 below. Each preparation is incubated with test compound at 37° C. for one hour. Aliquots (50 µL) are removed at 0, 30, and 60 min and quenched with 0.1% trifluoroacetic acid in acetonitrile. Samples are then centrifuged and analyzed by LC/MS/MS. Stability of prodrugs towards specific enzymes (e.g., peptidases, etc.) are also assessed in vitro by incubation with the purified enzyme:

Pancreatin Stability: Stability studies are conducted by incubating prodrug (5 µM) with 1% (w/v) pancreatin (Sigma, P-1625, from porcine pancreas) in 0.025 M Tris buffer containing 0.5 M NaCl (pH 7.5) at 37° C. for 60 min. The reaction is stopped by addition of 2 volumes of methanol. After centrifugation at 14,000 RPM for 10 min, the supernatant is removed and analyzed by LC/MS/MS.

Caco-2 Homogenate S9 Stability: Caco-2 cells are grown for 21 days prior to harvesting. Culture medium is removed and cell monolayers are rinsed and scraped into ice-cold 10 mM sodium phosphate/0.15 M potassium chloride, pH 7.4. Cells are lysed by sonication at 4° C. using a probe sonicator. Lysed cells are then transferred into 1.5 mL centrifuge vials and centrifuged at 9000 g for 20 min at 4° C. The resulting supernatant (Caco-2 cell homogenate S9 fraction) is aliquoted into 0.5 mL vials and stored at −80° C. until used.

For stability studies, prodrug (5 µM) is incubated in Caco-2 homogenate S9 fraction (0.5 mg protein per mL) for 60 min at 37° C. Concentrations of intact prodrug and released β-D-2'-C-methyl-ribofuranosyl cytidine are determined at zero time and 60 minutes using LC/MS/MS.

Preferred prodrugs demonstrate minimal cleavage to produce free β-D-2'-C-methyl-ribofuranosyl cytidine within a 60 minute period in Caco-2 cells (representative of human enterocytes), and efficient conversion to drug in either liver S-9 or plasma.

TABLE 1

Standard Conditions for Prodrug In Vitro Metabolism Studies

| Preparation | Substrate Concentration | Cofactors* |
| --- | --- | --- |
| Mouse Plasma | 2.0 µM | None |
| Human Plasma | 2.0 µM | None |
| Mouse Liver S9 (0.5 mg/mL) | 2.0 µM | NADPH |
| Human Liver S9 (0.5 mg/mL) | 2.0 µM | NADPH |
| Caco-2 Homogenate | 5.0 µM | None |
| Pancreatin | 5.0 µM | None |

*NADPH generating system, e.g., 1.3 mM NADP+, 3.3 mM glucose-6-phosphate, 0.4 U/mL glucose-6-phosphate dehydrogenase, 3.3 mM magnesium chloride and 0.95 mg/mL potassium phosphate, pH 7.4.

Finally, it should be noted that there are alternative ways of implementing the present disclosure. Accordingly, the present embodiments are to be considered as illustrative and not restrictive and the disclosure is not to be limited to the details given herein, but may be modified within the scope and equivalents of the appended claims.

What is claimed is:

1. A compound of structural Formula (I):

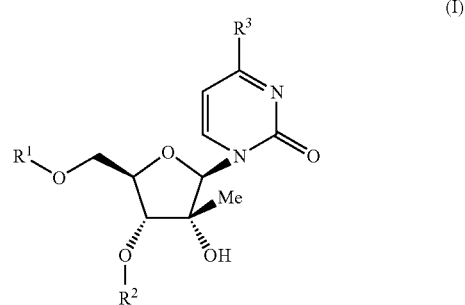

or a pharmaceutically acceptable salt thereof, wherein:

$R^1$ is selected from hydrogen, acyl, substituted acyl, acyloxyalkylcarbonyl, substituted acyloxyalkylcarbonyl, oxycarbonyl, substituted oxycarbonyl, and

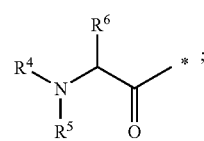

$R^2$ is selected from hydrogen, acyl, substituted acyl, acyloxyalkylcarbonyl, substituted acyloxyalkylcarbonyl, oxycarbonyl, substituted oxycarbonyl, and

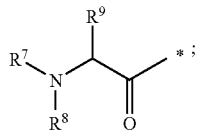

$R^3$ is selected from) —N=C($R^{10}$)($R^{11}$) and —NH$R^{12}$;

$R^4$ and $R^7$ are independently selected from hydrogen, alkyl, substituted alkyl, acyl, substituted acyl, acyloxyalkylcarbonyl, substituted acyloxyalkylcarbonyl, arylalkyl, substituted arylalkyl, oxycarbonyl, and substituted oxycarbonyl;

$R^5$ and $R^8$ are independently selected from hydrogen, alkyl, substituted alkyl, arylalkyl, substituted arylalkyl, cycloalkyl, and substituted cycloalkyl;

$R^6$ and $R^9$ are independently selected from hydrogen, alkyl, substituted alkyl, alkoxy, substituted alkoxy, acyl, substituted acyl, alkoxycarbonyl, substituted alkoxycarbonyl, aryl, substituted aryl, arylalkyl, substituted arylalkyl, carbamoyl, substituted carbamoyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, and substituted heteroarylalkyl;

or $R^5$ and $R^6$ together with the nitrogen atom to which they are bonded form a cycloheteroalkyl or substituted cycloheteroalkyl ring;

or $R^8$ and $R^9$ together with the nitrogen atom to which they are bonded form a cycloheteroalkyl or substituted cycloheteroalkyl ring;

$R^{10}$ and $R^{11}$ are independently selected from hydrogen, acyl, substituted acyl, alkyl, substituted alkyl, alkoxy, substituted alkoxy, alkylamino, substituted alkylamino, amido, substituted amido, aryl, substituted aryl, arylalkyl, substituted arylalkyl, cycloalkyl, substituted cycloalkyl, cycloheteroalkyl, substituted cycloheteroalkyl, dialkylamino, substituted dialkylamino, heteroalkyl, substituted heteroalkyl, heteroaryl, substituted heteroaryl, heteroarylalkyl, and substituted heteroarylalkyl;

$R^{12}$ is selected from acyloxyalkylcarbonyl, substituted acyloxyalkylcarbonyl, oxycarbonyl, substituted oxycarbonyl, and a moiety of structural Formula (II):

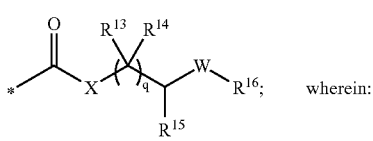

(II)

X is selected from O and CH$_2$;

q is selected from 1 and 2;

each $R^{13}$ and $R^{14}$ are independently selected from hydrogen, C$_{1-4}$ alkyl, phenyl, and substituted phenyl; or $R^{13}$ and $R^{14}$ together with the carbon atom to which they are both bonded form a C$_{3-7}$ cycloalkyl ring;

$R^{15}$ is selected from hydrogen, C$_{1-4}$ alkyl, and —CO$_2$R$^{17}$;

W is selected from O and NR$^{18}$;

$R^{17}$ is selected from hydrogen, C$_{1-4}$ alkyl, phenyl, and substituted phenyl;

$R^{18}$ is selected from hydrogen and C$_{1-4}$ alkyl;

$R^{16}$ is selected from C$_{1-4}$ alkyl, —C(O)R$^{19}$, —C(O)OR$^{20}$,

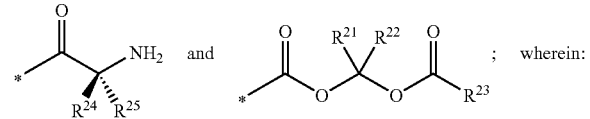

; wherein:

$R^{19}$ is selected from hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, and substituted heteroarylalkyl;

$R^{20}$ is selected from C$_{1-6}$ alkyl, C$_{3-7}$ cycloalkyl, aryl, substituted aryl, arylalkyl, substituted arylalkyl, heteroaryl, and substituted heteroaryl;

$R^{21}$ and $R^{22}$ are independently selected from hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, cycloalkoxycarbonyl, substituted cycloalkoxycarbonyl, heteroaryl, substituted heteroaryl, heteroarylalkyl, and substituted heteroarylalkyl; or $R^{21}$ and $R^{22}$ together with the carbon atom to which they are bonded form a cycloalkyl, substituted cycloalkyl, cycloheteroalkyl, or substituted cycloheteroalkyl ring;

$R^{23}$ is selected from acyl, substituted acyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, and substituted heteroarylalkyl;

$R^{24}$ is selected from hydrogen, alkyl, substituted alkyl, alkoxy, substituted alkoxy, acyl, substituted acyl, alkoxycarbonyl, substituted alkoxycarbonyl, aryl, substituted aryl, arylalkyl, substituted arylalkyl, carbamoyl, substituted carbamoyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, and substituted heteroarylalkyl; and $R^{25}$ is selected from hydrogen and C$_{1-4}$ alkyl; or $R^{24}$ and $R^{25}$ together with the carbon to which they are bonded form a cycloalkyl or cycloheteroalkyl ring;

wherein "substituted" is a group, wherein one or more hydrogen atoms are independently replaced with halogen, —OH, —CN, —CF$_3$, =O, —NO$_2$, C$_{1-3}$ alkoxy, C$_{1-3}$ alkyl, —COOR$^{64}$ wherein R$^{64}$ is selected from hydrogen and C$_{1-3}$ alkyl, and —NR$^{65}$$_2$ wherein each R$^{65}$ is independently selected from hydrogen and C$_{1-3}$ alkyl;

with the provisos that:

$R^3$ is not phenylcarbonylamino; and when $R^3$ is —NHR$^{12}$ wherein R$^{12}$ is a moiety of structural Formula (II), X is CH$_2$, and W is O; then R$^{16}$ is not C$_{1-4}$ alkyl.

2. The compound of claim 1, wherein $R^1$ is selected from hydrogen, acyl, substituted acyl, acyloxyalkylcarbonyl, substituted acyloxyalkylcarbonyl, oxycarbonyl, and substituted oxycarbonyl.

3. The compound of claim 1, wherein $R^2$ is selected from hydrogen, acyl, substituted acyl, acyloxyalkylcarbonyl, substituted acyloxyalkylcarbonyl, oxycarbonyl, and substituted oxycarbonyl.

4. The compound of claim 1, wherein $R^3$ is —N=C($R^{10}$)($R^{11}$), wherein $R^{10}$ and $R^{11}$ are independently selected from hydrogen, alkoxy, substituted alkoxy, alkyl, substituted alkyl, alkylamino, substituted alkylamino, amido, substituted amido, aryl, substituted aryl, arylalkyl, substituted arylalkyl, dialkylamino, substituted dialkylamino, heteroalkyl, substituted heteroalkyl, heteroaryl, substituted heteroaryl, heteroarylalkyl, and substituted heteroarylalkyl.

5. The compound of claim 1, wherein $R^3$ is —NH$R^{12}$, and $R^{12}$ is selected from acyloxyalkylcarbonyl, substituted acyloxyalkylcarbonyl, oxycarbonyl, substituted oxycarbonyl, and a moiety of structural Formula (II).

6. The compound of claim 1, wherein $R^4$ and $R^7$ are independently selected from hydrogen, acyl, substituted acyl, acyloxyalkylcarbonyl, substituted acyloxyalkylcarbonyl, oxycarbonyl, and substituted oxycarbonyl.

7. The compound of claim 1, wherein $R^5$ and $R^8$ are independently selected from hydrogen, alkyl, substituted alkyl, arylalkyl, substituted arylalkyl, cycloalkyl, and substituted cycloalkyl.

8. The compound of claim 1, wherein $R^6$ and $R^9$ are independently selected from hydrogen, alkanyl, substituted alkanyl, aryl, substituted aryl, arylalkanyl, substituted arylalkanyl, cycloalkanyl, heteroarylalkanyl, and substituted heteroarylalkanyl.

9. The compound of claim 1, wherein $R^5$ and $R^6$, or $R^8$ and $R^9$, together with the atoms to which they are bonded form a cycloheteroalkyl or substituted cycloheteroalkyl ring.

10. The compound of claim 1, wherein $R^1$ is hydrogen; $R^2$ is hydrogen; $R^3$ is —N=C($R^{10}$)($R^{11}$), wherein $R^{10}$ and $R^{11}$ are independently selected from hydrogen, alkoxy, substituted alkoxy, alkyl, substituted alkyl, alkylamino, substituted alkylamino, amido, substituted amido, aryl, substituted aryl, arylalkyl, substituted arylalkyl, dialkylamino, substituted dialkylamino, heteroalkyl, substituted heteroalkyl, heteroaryl, substituted heteroaryl, heteroarylalkyl, and substituted heteroarylalkyl.

11. The compound of claim 1, wherein:
$R^1$ is

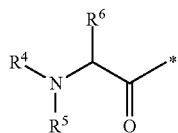

and $R^2$ is hydrogen; or
$R^1$ is hydrogen and $R^2$ is

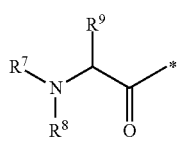

and
$R^3$ is —N=C($R^{10}$)($R^{11}$), wherein:
$R^{10}$ and $R^{11}$ are independently selected from hydrogen, alkoxy, substituted alkoxy, alkyl, substituted alkyl, alkylamino, substituted alkylamino, amido, substituted amido, aryl, substituted aryl, arylalkyl, substituted arylalkyl, dialkylamino, substituted dialkylamino, heteroalkyl, substituted heteroalkyl, heteroaryl, substituted heteroaryl, heteroarylalkyl, and substituted heteroarylalkyl.

12. The compound of claim 11, wherein:
each of $R^4$ and $R^5$ is hydrogen;
$R^6$ is selected from hydrogen, methyl, isopropyl, isobutyl, sec-butyl, tert-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl, and 3-indolylmethyl; or $R^5$ and $R^6$ together with the nitrogen atom to which they are bonded form an azetidine, pyrrolidine, or piperidine ring;
each of $R^7$ and $R^8$ is hydrogen; and
$R^9$ is selected from hydrogen, methyl, isopropyl, isobutyl, sec-butyl, tert-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl, and 3-indolylmethyl; or $R^8$ and $R^9$ together with the nitrogen atom to which they are bonded form an azetidine, pyrrolidine or piperidine ring.

13. The compound of claim 1, wherein:
$R^1$ is hydrogen;
$R^2$ is hydrogen; and
$R^3$ is —NH$R^{12}$, wherein $R^{12}$ is selected from acyloxyalkylcarbonyl, substituted acyloxyalkylcarbonyl, oxycarbonyl, substituted oxycarbonyl, and a moiety of structural Formula (II).

14. The compound of claim 13, wherein
$R^{12}$ is —C(O)O$R^{26}$;
$R^{26}$ is selected from C$_{1-6}$ alkyl, C$_{3-7}$ cycloalkyl, aryl, substituted aryl, arylalkyl, substituted arylalkyl, heteroaryl, substituted heteroaryl, and CH$_2$$R^{27}$; wherein
$R^{27}$ is selected from trifluoromethyl, cyano, C$_{1-4}$ alkanesulfonyl, benzenesulfonyl, and substituted benzenesulfonyl.

15. The compound of claim 1, wherein:
$R^1$ is

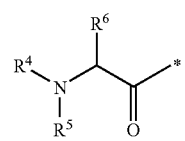

and $R^2$ is hydrogen; or
$R^1$ is hydrogen and $R^2$ is

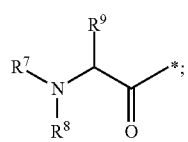

and $R^3$ is —$NHR^{12}$; wherein
$R^{12}$ is selected from acyloxyalkylcarbonyl, substituted acyloxyalkylcarbonyl, oxycarbonyl, substituted oxycarbonyl, and a moiety of structural Formula (II).

16. The compound of claim 15, wherein:
each of $R^4$ and $R^5$ is hydrogen;
$R^6$ is selected from hydrogen, methyl, isopropyl, isobutyl, sec-butyl, tert-butyl, cyclopentyl, cyclohexyl, —$CH_2OH$, —$CH(OH)CH_3$, —$CH_2CO_2H$, —$CH_2CH_2CO_2H$, —$CH_2CONH_2$, —$CH_2CH_2CONH_2$, —$CH_2CH_2SCH_3$, —$CH_2SH$, —$CH_2(CH_2)_3NH_2$, —$CH_2CH_2CH_2NHC(NH)NH_2$, phenyl, benzyl, 4-hydroxybenzyl, 4-imidazolylmethyl, and 3-indolylmethyl; or $R^5$ and $R^6$ together with the nitrogen atom to which they are bonded form an azetidine, pyrrolidine, or piperidine ring;
each of $R^7$ and $R^8$ is hydrogen; and
$R^9$ is selected from hydrogen, methyl, isopropyl, isobutyl, sec-butyl, tert-butyl, cyclopentyl, cyclohexyl, —$CH_2OH$, —$CH(OH)CH_3$, —$CH_2CO_2H$, —$CH_2CH_2CO_2H$, —$CH_2CONH_2$, —$CH_2CH_2CONH_2$, —$CH_2CH_2SCH_3$, —$CH_2SH$, —$CH_2(CH_2)_3NH_2$, —$CH_2CH_2CH_2NHC(NH)NH_2$, phenyl, benzyl, 4-hydroxybenzyl, 4-imidazolylmethyl, and 3-indolylmethyl; or $R^8$ and $R^9$ together with the nitrogen atom to which they are bonded form an azetidine, pyrrolidine, or piperidine ring.

17. The compound of claim 1, wherein:
$R^1$ is selected from hydrogen, acyl, substituted acyl, acyloxyalkylcarbonyl, substituted acyloxyalkylcarbonyl, oxycarbonyl, substituted oxycarbonyl, and

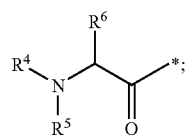

$R^2$ is selected from hydrogen, acyl, substituted acyl, acyloxyalkylcarbonyl, substituted acyloxyalkylcarbonyl, oxycarbonyl, substituted oxycarbonyl, and
$R^3$ is —$NHR^{12}$; wherein $R^{12}$ is

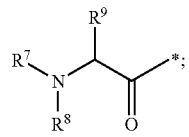

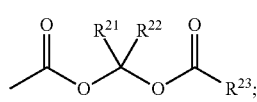

wherein:
$R^{21}$ and $R^{22}$ are independently selected from hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, cycloalkoxycarbonyl, substituted cycloalkoxycarbonyl, heteroaryl, substituted heteroaryl, heteroarylalkyl, and substituted heteroarylalkyl; or $R^{21}$ and $R^{22}$ together with the carbon atom to which they are bonded form a cycloalkyl, substituted cycloalkyl, cycloheteroalkyl, or substituted cycloheteroalkyl ring; and
$R^{23}$ is selected from acyl, substituted acyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, and substituted heteroarylalkyl.

18. The compound of claim 17, wherein:
$R^{21}$ and $R^{22}$ are independently selected from hydrogen, $C_{1-4}$ alkyl, substituted $C_{1-4}$ alkyl, $C_{1-4}$ alkoxycarbonyl, $C_{3-6}$ cycloalkyl, $C_{3-6}$ cycloalkoxycarbonyl, phenyl, substituted phenyl, $C_{7-9}$ phenylalkyl, and pyridyl; or $R^{21}$ and $R^{22}$ together with the carbon atom to which they are bonded form a $C_{3-6}$ cycloalkyl ring; and
$R^{23}$ is selected from $C_{1-6}$ alkyl, substituted $C_{1-6}$ alkyl, $C_{3-6}$ cycloalkyl, phenyl, substituted phenyl, $C_{7-9}$ phenylalkyl, pyridyl, and substituted pyridyl.

19. The compound of claim 17, wherein:
$R^{21}$ is selected from hydrogen, methyl, ethyl, propyl, isopropyl, butyl, isobutyl, sec-butyl, tert-butyl, cyclopentyl, cyclohexyl, phenyl, benzyl, phenethyl, and 3-pyridyl;
$R^{22}$ is hydrogen; and
$R^{23}$ is selected from methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, 1,1-dimethoxyethyl, 1,1-diethoxyethyl, phenyl, 2-methylphenyl, 2,6-dimethylphenyl, 2-methoxyphenyl, 4-methoxyphenyl, 2,6-dimethoxyphenyl, benzyl, phenethyl, styryl, cyclopropyl, cyclobutyl, cyclopentyl, cyclohexyl, and 3-pyridyl.

20. The compound of claim 19, wherein each of $R^1$ and $R^2$ is hydrogen.

21. The compound of claim 20, wherein $R^{21}$ is selected from hydrogen, methyl, propyl, isopropyl, and tert-butyl.

22. The compound of claim 19, wherein:
$R^1$ is

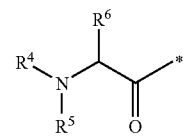

and $R^2$ is hydrogen; or
$R^1$ is hydrogen and $R^2$ is

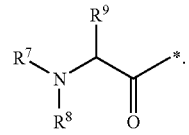

23. The compound of claim 22, wherein:
each of $R^4$ and $R^5$ is hydrogen;
$R^6$ is selected from hydrogen, methyl, isopropyl, isobutyl, sec-butyl, tert-butyl, cyclopentyl, cyclohexyl, —$CH_2OH$, —$CH(OH)CH_3$, —$CH_2CO_2H$, —$CH_2CH_2CO_2H$, —$CH_2CONH_2$, —$CH_2CH_2CONH_2$, —$CH_2CH_2SCH_3$, —$CH_2SH$, —$CH_2(CH_2)_3NH_2$, —$CH_2CH_2CH_2NHC(NH)NH_2$, phenyl, benzyl, 4-hydroxybenzyl, 4-imidazolylmethyl, and 3-indolylmethyl;

or R⁵ and R⁶ together with the nitrogen atom to which they are bonded form an azetidine, pyrrolidine, or piperidine ring;

each of R⁷ and R⁸ is hydrogen; and

R⁹ is selected from hydrogen, methyl, isopropyl, isobutyl, sec-butyl, tert-butyl, cyclopentyl, cyclohexyl, —CH₂OH, —CH(OH)CH₃, —CH₂CO₂H, —CH₂CH₂CO₂H, —CH₂CONH₂, —CH₂CH₂CONH₂, —CH₂CH₂SCH₃, —CH₂SH, —CH₂(CH₂)₃NH₂, —CH₂CH₂CH₂NHC(NH)NH₂, phenyl, benzyl, 4-hydroxybenzyl, 4-imidazolylmethyl, and 3-indolylmethyl; or R⁸ and R⁹ together with the nitrogen atom to which they are bonded form an azetidine, pyrrolidine, or piperidine ring.

24. The compound of claim 22, wherein R²¹ is selected from hydrogen, methyl, propyl, isopropyl, and tert-butyl.

25. The compound of claim 1, wherein:

R¹ is selected from hydrogen, acyl, substituted acyl, acyloxyalkylcarbonyl, substituted acyloxyalkylcarbonyl, oxycarbonyl, substituted oxycarbonyl, and

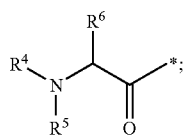

R² is selected from hydrogen, acyl, substituted acyl, acyloxyalkylcarbonyl, substituted acyloxyalkylcarbonyl, oxycarbonyl, substituted oxycarbonyl, and

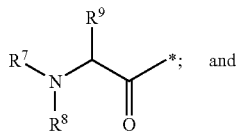

R³ is —NHR¹², wherein R¹² is a moiety of structural Formula (II):

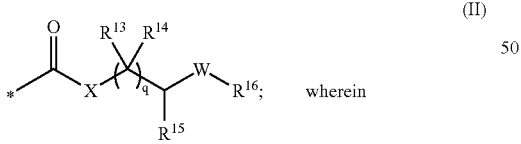

(II)

X is selected from O and CH₂;

q is selected from 1 and 2;

each R¹³ and R¹⁴ is independently selected from hydrogen, C₁₋₄ alkyl, phenyl, and substituted phenyl; or R¹³ and R¹⁴ together with the carbon atom to which they are both bonded form a C₃₋₇ cycloalkyl ring;

R¹⁵ is selected from hydrogen, C₁₋₄ alkyl, and —CO₂R¹⁷;

W is selected from O and NR¹⁸;

R¹⁷ is selected from hydrogen, C₁₋₄ alkyl, phenyl, and substituted phenyl;

R¹⁸ is selected from hydrogen and C₁₋₄ alkyl; and

R¹⁶ is selected from C₁₋₄ alkyl, —C(O)R¹⁹, —C(O)OR²⁰,

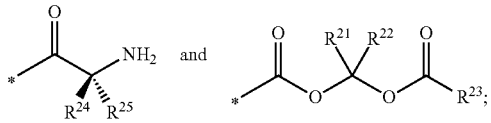

wherein:

R¹⁹ is selected from hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, and substituted heteroarylalkyl;

R²⁰ is selected from C₁₋₆ alkyl, C₃₋₇ cycloalkyl, aryl, substituted aryl, arylalkyl, substituted arylalkyl, heteroaryl, and substituted heteroaryl;

R²¹ and R²² are independently selected from hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, cycloalkoxycarbonyl, substituted cycloalkoxycarbonyl, heteroaryl, substituted heteroaryl, heteroarylalkyl, and substituted heteroarylalkyl; or R²¹ and R²² together with the carbon atom to which they are bonded form a cycloalkyl, substituted cycloalkyl, cycloheteroalkyl, or substituted cycloheteroalkyl ring;

R²³ is selected from acyl, substituted acyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, and substituted heteroarylalkyl;

R²⁴ is selected from hydrogen, alkyl, substituted alkyl, alkoxy, substituted alkoxy, acyl, substituted acyl, alkoxycarbonyl, substituted alkoxycarbonyl, aryl, substituted aryl, arylalkyl, substituted arylalkyl, carbamoyl, substituted carbamoyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, and substituted heteroarylalkyl; and R²⁵ is selected from hydrogen and C₁₋₄ alkyl; or R²⁴ and R²⁵ together with the carbon to which they are bonded form a cycloalkyl or cycloheteroalkyl ring;

with the proviso that:

when X is CH₂ and W is O; then R¹⁶ is not C₁₋₄ alkyl.

26. The compound of claim 25, wherein R²¹ is selected from hydrogen, methyl, ethyl, propyl, isopropyl, butyl, isobutyl, sec-butyl, tert-butyl, cyclopentyl, cyclohexyl, phenyl, benzyl, phenethyl, and 3-pyridyl; and R²² is hydrogen.

27. The compound of claim 25, wherein R²³ is selected from methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, 1,1-dimethoxyethyl, 1,1-diethoxyethyl, phenyl, 2-methylphenyl, 2,6-dimethylphenyl, 2-methoxyphenyl, 4-methoxyphenyl, 2,6-dimethoxyphenyl, benzyl, phenethyl, styryl, cyclopropyl, cyclobutyl, cyclopentyl, cyclohexyl, and 3-pyridyl.

28. The compound of claim 25, wherein R²⁴ is selected from hydrogen, methyl, isopropyl, isobutyl, sec-butyl, tert-butyl, cyclopentyl, cyclohexyl, —CH₂OH, —CH(OH)CH₃, —CH₂CO₂H, —CH₂CH₂CO₂H, —CH₂CONH₂, —CH₂CH₂CONH₂, —CH₂CH₂SCH₃, —CH₂SH, —CH₂

(CH₂)₃NH₂, —CH₂CH₂CH₂NHC(NH)NH₂, phenyl, benzyl, 4-hydroxybenzyl, 4-imidazolylmethyl, and 3-indolylmethyl.

29. The compound of claim 28, wherein R²⁵ is hydrogen.

30. The compound of claim 25, wherein:
X is O;
q is 1;
each of R¹³ and R¹⁴ is hydrogen;
R¹⁵ is hydrogen;
W is NR¹⁸, wherein R¹⁸ is hydrogen; and
R₁₆ is

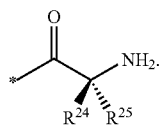

31. The compound of claim 30, wherein:
R²⁴ is selected from hydrogen, methyl, isopropyl, isobutyl, sec-butyl, tert-butyl, cyclopentyl, cyclohexyl, —CH₂OH, —CH(OH)CH₃, —CH₂CO₂H, —CH₂CH₂CO₂H, —CH₂CONH₂, —CH₂CH₂CONH₂, —CH₂CH₂SCH₃, —CH₂SH, —CH₂(CH₂)₃NH₂, —CH₂CH₂CH₂NHC(NH)NH₂, phenyl, benzyl, 4-hydroxybenzyl, 4-imidazolylmethyl, and 3-indolylmethyl; and
R²⁵ is hydrogen.

32. The compound of claim 31, wherein each of R¹ and R² is hydrogen.

33. The compound of claim 31, wherein:
R¹ is

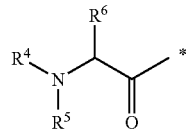

and R² is hydrogen; or
R¹ is hydrogen and R² is

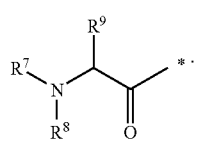

34. The compound of claim 33, wherein:
each of R⁴ and R⁵ is hydrogen;
R⁶ is selected from hydrogen, methyl, isopropyl, isobutyl, sec-butyl, tert-butyl, cyclopentyl, cyclohexyl, —CH₂OH, —CH(OH)CH₃, —CH₂CO₂H, —CH₂CH₂CO₂H, —CH₂CONH₂, —CH₂CH₂CONH₂, —CH₂CH₂SCH₃, —CH₂SH, —CH₂(CH₂)₃NH₂, —CH₂CH₂CH₂NHC(NH)NH₂, phenyl, benzyl, 4-hydroxybenzyl, 4-imidazolylmethyl, and 3-indolylmethyl; or R⁵ and R⁶ together with the nitrogen atom to which they are bonded form an azetidine, pyrrolidine, or piperidine ring;
each of R⁷ and R⁸ is hydrogen; and
R⁹ is selected from hydrogen, methyl, isopropyl, isobutyl, sec-butyl, tert-butyl, cyclopentyl, cyclohexyl, —CH₂OH, —CH(OH)CH₃, —CH₂CO₂H, —CH₂CH₂CO₂H, —CH₂CONH₂, —CH₂CH₂CONH₂, —CH₂CH₂SCH₃, —CH₂SH, —CH₂(CH₂)₃NH₂, —CH₂CH₂CH₂NHC(NY)NH₂, phenyl, benzyl, 4-hydroxybenzyl, 4-imidazolylmethyl, and 3-indolylmethyl; or R⁸ and R⁹ together with the nitrogen atom to which they are bonded form an azetidine, pyrrolidine or piperidine ring.

35. The compound of claim 25, wherein:
X is O;
q is 1;
each of R¹³ and R¹⁴ is hydrogen;
R¹⁵ is selected from hydrogen and —CO₂H;
W is selected from O and NR¹⁸ wherein R¹⁸ is selected from hydrogen and methyl; and
R¹⁶ is selected from

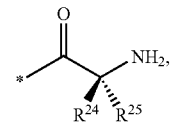

methyl, —C(O)R¹⁹, and —C(O)OR²⁰.

36. The compound of claim 35, wherein:
R¹ is hydrogen;
R² is hydrogen;
R²⁴ is selected from hydrogen, methyl, isopropyl, isobutyl, sec-butyl, tert-butyl, cyclopentyl, cyclohexyl, —CH₂OH, —CH(OH)CH₃, —CH₂CO₂H, —CH₂CH₂CO₂H, —CH₂CONH₂, —CH₂CH₂CONH₂, —CH₂CH₂SCH₃, —CH₂SH, —CH₂(CH₂)₃NH₂, —CH₂CH₂CH₂NHC(NH)NH₂, phenyl, benzyl, 4-hydroxybenzyl, 4-imidazolylmethyl, and 3-indolylmethyl; and
R²⁵ is hydrogen.

37. The compound of claim 35, wherein each of R¹ and R² is hydrogen.

38. The compound of claim 35, wherein:
R¹ is

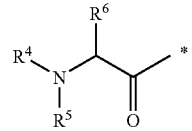

and R² is hydrogen; or
R¹ is hydrogen and R² is

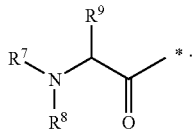

39. The compound of claim 38, wherein:
each of R⁴ and R⁵ is hydrogen;
R⁶ is selected from hydrogen, methyl, isopropyl, isobutyl, sec-butyl, tert-butyl, cyclopentyl, cyclohexyl, —CH₂OH, —CH(OH)CH₃, —CH₂CO₂H, —CH₂CH₂CO₂H, —CH₂CONH₂, —CH₂CH₂CONH₂, —CH₂CH₂SCH₃, —CH₂SH, —CH₂(CH₂)₃NH₂, —CH₂CH₂CH₂NHC(NH)NH₂, phenyl, benzyl, 4-hydroxybenzyl, 4-imidazolylmethyl, and 3-indolylmethyl; or $R^5$ and $R^6$ together with the nitrogen atom to which they are bonded form an azetidine, pyrrolidine, or piperidine ring;

each of $R^7$ and $R^8$ is hydrogen; and $R^9$ is selected from hydrogen, methyl, isopropyl, isobutyl, sec-butyl, tert-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl, and 3-indolylmethyl; or $R^8$ and $R^9$ together with the nitrogen atom to which they are bonded form an azetidine, pyrrolidine, or piperidine ring.

40. The compound of claim 25, wherein:

X is CH$_2$;

q is 1;

each of $R^{13}$ and $R^{14}$ is hydrogen;

$R^{15}$ is hydrogen;

W is selected from O and NR$^{18}$ wherein $R^{18}$ is hydrogen; and $R^{16}$ is selected from —C(O)R$^{19}$ and —C(O)OR$^{20}$.

41. The compound of claim 40, wherein $R^{19}$ is selected from $C_{1-6}$ alkyl, substituted $C_{1-6}$ alkyl, $C_{3-6}$ cycloalkyl, phenyl, substituted phenyl, $C_{7-9}$ phenylalkyl, pyridyl, and substituted pyridyl.

42. The compound of claim 40, wherein each of $R^1$ and $R^2$ is hydrogen.

43. The compound of claim 40, wherein:

$R^1$ is

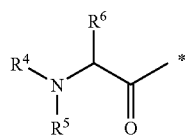

and $R^2$ is hydrogen; or
$R^1$ is hydrogen and $R^2$ is.

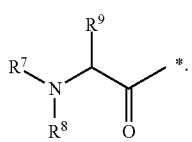

44. The compound of claim 43, wherein:

each of $R^4$ and $R^5$ is hydrogen;

$R^6$ is selected from hydrogen, methyl, isopropyl, isobutyl, sec-butyl, tert-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl, and 3-indolylmethyl; or $R^5$ and $R^6$ together with the nitrogen atom to which they are bonded form an azetidine, pyrrolidine, or piperidine ring;

each of $R^7$ and $R^8$ is hydrogen; and $R^9$ is selected from hydrogen, methyl, isopropyl, isobutyl, sec-butyl, tert-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl, and 3-indolylmethyl; or $R^8$ and $R^9$ together with the nitrogen atom to which they are bonded form an azetidine, pyrrolidine, or piperidine ring.

45. The compound of claim 40, wherein $R^{20}$ is selected from $C_{1-6}$ alkanyl, $C_{2-6}$ alk-1-en-2-yl, 2-$C_{3-7}$ cycloalkyl-eth-1-en-2-yl, 2-phenyleth-1-en-2-yl, substituted 2-phenyleth-1-en-2-yl, $C_{3-7}$ cycloalkanyl, $C_{5-7}$ cycloalk-1-en-1-yl, phenyl, naphthyl, halophenyl, methoxyphenyl, cyanophenyl, carboxyphenyl, $C_{1-4}$ alkoxycarbonylphenyl, aminophenyl, halobenzyl, methoxybenzyl, cyanobenzyl, carboxybenzyl, $C_{1-4}$ alkoxycarbonylbenzyl, aminobenzyl, furyl, thienyl, pyrrolyl, imidazoyl, oxazolyl, pyridyl, pyrimidyl, pyraziny, and triazinyl.

46. The compound of claim 45, wherein each of $R^1$ and $R^2$ is hydrogen.

47. The compound of claim 25, wherein:

X is O;

q is 1;

each of $R^{13}$ and $R^{14}$ is hydrogen;

$R^{15}$ is hydrogen;

W is NR$^{18}$, wherein $R^{18}$ is selected from hydrogen and methyl; and $R_{16}$ is

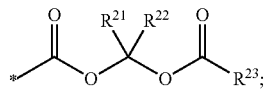

wherein $R^{21}$ is selected from hydrogen, methyl, ethyl, propyl, isopropyl, tert-butyl, cyclopentyl, cyclohexyl, and phenyl;

$R^{22}$ K is hydrogen; and $R^{23}$ is selected from methyl, ethyl, propyl, isopropyl, butyl, isobutyl, sec-butyl, tert-butyl, pent-1-yl, pent-2-yl, pent-3-yl, 2-methylbut-1-yl, 3-methylbut-1-yl, 1,1-dimethoxyethyl, 1,1-diethoxyethyl, phenyl, 2-methylphenyl, 2,6-dimethylphenyl, 2-methoxyphenyl, 4-methoxyphenyl, 2,6-dimethoxyphenyl, benzyl, phenethyl, styryl, cyclopropyl, cyclobutyl, cyclopentyl, cyclohexyl, and 3-pyridyl.

48. The compound of claim 47, wherein each of $R^1$ and $R^2$ is hydrogen.

49. The compound of claim 47, wherein:

$R^1$ is

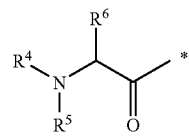

and $R^2$ is hydrogen; or

R¹ is hydrogen and R² is

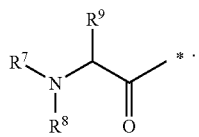

50. The compound of claim 49, wherein:
each of R⁴ and R⁵ is hydrogen;
R⁶ is selected from hydrogen, methyl, isopropyl, isobutyl, sec-butyl, tert-butyl, cyclopentyl, cyclohexyl, —CH₂OH, —CH(OH)CH₃, —CH₂CO₂H, —CH₂CH₂CO₂H, —CH₂CONH₂, —CH₂CH₂CONH₂, —CH₂CH₂SCH₃, —CH₂SH, —CH₂(CH₂)₃NH₂, —CH₂CH₂CH₂NHC(NH)NH₂, phenyl, benzyl, 4-hydroxybenzyl, 4-imidazolylmethyl, and 3-indolylmethyl; or R⁵ and R⁶ together with the nitrogen atom to which they are bonded form an azetidine, pyrrolidine, or piperidine ring;
each of R⁷ and R⁸ is hydrogen; and
R⁹ is selected from hydrogen, methyl, isopropyl, isobutyl, sec-butyl, tert-butyl, cyclopentyl, cyclohexyl, —CH₂OH, —CH(OH)CH₃, —CH₂CO₂H, —CH₂CH₂CO₂H, —CH₂CONH₂, —CH₂CH₂CONH₂, —CH₂CH₂SCH₃, —CH₂SH, —CH₂(CH₂)₃NH₂, —CH₂CH₂CH₂NHC(NH)NH₂, phenyl, benzyl, 4-hydroxybenzyl, 4-imidazolylmethyl, and 3-indolylmethyl; or R⁸ and R⁹ together with the nitrogen atom to which they are bonded form an azetidine, pyrrolidine, or piperidine ring.

51. The compound of claim 1, wherein the compound is selected from:
β-1-(4-allyloxycarbonylamino-2-oxo-1H-pyrimidin-1-yl)-2-C-methyl-ribofuranose;
β-1-(4-benzyloxycarbonylamino-2-oxo-1H-pyrimidin-1-yl)-2-C-methyl-ribofuranose;
β-1-(4-ethoxycarbonylamino-2-oxo-1H-pyrimidin-1-yl)-2-C-methyl-ribofuranose;
β-1-(4-ethoxycarbonylamino-2-oxo-1H-pyrimidin-1-yl)-5-O-(tert-butyldimethylsilyl)-2-C-methyl-ribofuranose;
β-1-(4-ethoxycarbonylamino-2-oxo-1H-pyrimidin-1-yl)-3-O-(N-tert-butyloxycarbonyl-L-valinyl)-5-O-(tert-butyldimethylsilyl)-2-C-methyl-ribofuranose;
β-1-(4-ethoxycarbonylamino-2-oxo-1H-pyrimidin-1-yl)-3-O-(L-valinyl)-2-C-methyl-ribofuranose;
β-1-(4-ethoxycarbonylamino-2-oxo-1H-pyrimidin-1-yl)-3-O-(tetrahydropyranyl)-5-O-(tert-butyldimethylsilyl)-2-C-methyl-ribofuranose;
β-1-(4-ethoxycarbonylamino-2-oxo-1H-pyrimidin-1-yl)-3-O-(tetrahydropyranyl)-2-C-methyl-ribofuranose;
β-1-(4-ethoxycarbonylamino-2-oxo-1H-pyrimidin-1-yl)-3-O-(tetrahydropyranyl)-5-O-(N-tert-butoxycarbonyl-L-valinyl)-2-C-methyl-ribofuranose;
β-1-(4-ethoxycarbonylamino-2-oxo-1H-pyrimidin-1-yl)-5-O-(L-valinyl)-2-C-methyl-ribofuranose;
β-1-(4-allyloxycarbonylamino-2-oxo-1H-pyrimidin-1-yl)-5-O-(tert-butyldimethylsilyl)-2-C-methyl-ribofuranose;
β-1-(4-Pentyloxycarbonylamino-2-oxo-1H-pyrimidin-1-yl)-2-C-methyl-ribofuranose;
β-1-(4-Pentyloxycarbonylamino-2-oxo-1H-pyrimidin-1-yl)-3-O-(pentyloxycarbonyl)-2-C-methyl-ribofuranose;
β-1-(4-Pentyloxycarbonylamino-2-oxo-1H-pyrimidin-1-yl)-5-O-(pentyloxycarbonyl)-2-C-methyl-ribofuranose;
β-1-(4-Pentyloxycarbonylamino-2-oxo-1H-pyrimidin-1-yl)-3-O-(pentyloxycarbonyl)-5-O-(pentyloxycarbonyl)-2-C-methyl-ribofuranose;
β-1-(4-Phenyloxycarbonylamino-2-oxo-1H-pyrimidin-1-yl)-2-C-methyl-ribofuranose;
β-1-(4-(4-Methoxyphenyl)oxycarbonylamino-2-oxo-1H-pyrimidin-1-yl)-2-C-methyl-ribofuranose;
β-1-(4-(1,1,1-Trifluoroethyl)oxycarbonylamino-2-oxo-1H-pyrimidin-1-yl)-2-C-methyl-ribofuranose;
β-1-(4-(4-Methoxybenzyl)oxycarbonylamino-2-oxo-1H-pyrimidin-1-yl)-2-C-methyl-ribofuranose;
β-1-(4-(Propen-2-yl)oxycarbonylamino-2-oxo-1H-pyrimidin-1-yl)-2-C-methyl-ribofuranose;
β-1-(4-(2-Carboxy-2-methyl)ethoxycarbonylamino-2-oxo-1H-pyrimidin-1-yl)-2-C-methyl-ribofuranose;
β-1-(4-Pentyloxycarbonylamino-2-oxo-1H-pyrimidin-1-yl)-5-O-acetyl-2-C-methyl-ribofuranose;
β-1-(4-Pentyloxycarbonylamino-2-oxo-1H-pyrimidin-1-yl)-3-O-acetyl-2-C-methyl-ribofuranose;
β-1-(4-Acetoxymethoxycarbonylamino-2-oxo-1H-pyrimidin-1-yl)-2-C-methyl-ribofuranose;
β-1-(4-(1-Isobutanoyloxyethoxy)carbonylamino-2-oxo-1H-pyrimidin-1-yl)-2-C-methyl-ribofuranose;
β-1-(4-(2,6-Dimethylbenzoyl)oxymethoxycarbonylamino-2-oxo-1H-pyrimidin-1-yl)-2-C-methyl-ribofuranose;
β-1-(4-(2-Methylbenzoyl)oxymethoxycarbonylamino-2-oxo-1H-pyrimidin-1-yl)-2-C-methyl-ribofuranose;
β-1-(4-Acetoxymethoxycarbonylamino-2-oxo-1H-pyrimidin-1-yl)-5-O-(L-valinyl)-2-C-methyl-ribofuranose;
β-1-{[4-((2S)-((2S)-Aminopropionylamino)-2-carboxy)ethoxycarbonylamino]-2-oxo-1H-pyrimidin-1-yl}-2-C-methyl-ribofuranose;
β-1-{[4-((2S)-((2S)-Amino-3,3-dimethylbutyroylamino)-2-carboxy)ethoxycarbonylamino]-2-oxo-1H-pyrimidin-1-yl}-2-C-methyl-ribofuranose;
β-1-{[4-((2S)-(Aminoacetylamino)-2-carboxy)ethoxycarbonylamino]-2-oxo-1H-pyrimidin-1-yl}-2-C-methyl-ribofuranose;
β-1-{[4((2S)-((2S)-Aminophenacetylamino)-2-carboxy)ethoxycarbonylamino]-2-oxo-1H-pyrimidin-1-yl}-2-C-methyl-ribofuranose;
β-1-{[4((2S)-(2-Amino-2-methylpropionylamino)-2-carboxy)ethoxycarbonylamino]-2-oxo-1H-pyrimidin-1-yl}-2-C-methyl-ribofuranose;
β-1-{[4-((2S)-(1-Amino-cyclohexanecarbonylamino)-2-carboxy)ethoxycarbonylamino]-2-oxo-1H-pyrimidin-1-yl}-2-C-methyl-ribofuranose;
β-1-(4-(2-Acetoxyethoxy)carbonylamino-2-oxo-1H-pyrimidin-1-yl)-2-C-methyl-ribofuranose;
β-1-(4-(2-Pivaloyloxyethoxy)carbonylamino-2-oxo-1H-pyrimidin-1-yl)-2-C-methyl-ribofuranose;
β-1-(4-(2-Cyclohexanecarboxyethoxy)carbonylamino-2-oxo-1H-pyrimidin-1-yl)-2-C-methyl-ribofuranose;
β-1-{[4-(2-((2S)-Amino-3-methylbutyroylamino)-ethoxycarbonylamino]-2-oxo-1H-pyrimidin-1-yl}-2-C-methyl-ribofuranose;
β-1-{[4-(2-((2S)-Amino-3-phenylpropionylamino)-ethoxycarbonylam ino]-2-oxo-1H-pyrimidin-1-yl}-2-C-methyl-ribofuranose;
β-1-{[4-(2-(Phenyloxycarbonylamino)-ethoxycarbonylamino]-2-oxo-1H-pyrimidin-1-yl}-2-C-methyl-ribofuranose;

β-1-{[4-(3-(Benzyloxycarbonylamino)-propoxycarbonylamino]-2-oxo-1H-pyrimidin-1-yl}-2-C-methyl-ribofuranose;

β-1-[4-(2-Dimethylamino-ethoxycarbonylamino)-2-oxo-1H-pyrimidin-1-yl]-2-C-methyl-ribofuranose;

β-1-[4-(4-Acetoxybutyroylamino)-2-oxo-1H-pyrimidin-1-yl]-2-C-methyl-ribofuranose;

β-1-[4-(4-Pivaloyloxybutyroylamino)-2-oxo-1H-pyrimidin-1-yl]-2-C-methyl-ribofuranose;

β-1-{[4-(2-((1-Pivaloyloxy-2,2-dimethylpropyl)oxycarbonylamino)-ethoxycarbonylamino]-2-oxo-1H-pyrimidin-1-yl}-2-C-methyl-ribofuranose;

β-1-{[4-(2-((Isobutanoyloxymethyl)oxycarbonylamino)-ethoxycarbonylamino]-2-oxo-1H-pyrimidin-1-yl}-2-C-methyl-ribofuranose;

β-1-{[4-(2-((Acetoxymethypoxycarbonylamino)-ethoxycarbonylamino]-2-oxo-1H-pyrimidin-1-yl}-2-C-methyl-ribofuranose;

β-1-{[4-(2-((1-Isobutanoyloxyethypoxycarbonylamino)-ethoxycarbonylamino]-2-oxo-1H-pyrimidin-1-yl}-2-C-methyl-ribofuranose;

β-1-{[4-(2-((1-Acetoxy-2-methylpropyl)oxycarbonylamino)-ethoxycarbonylamino]-2-oxo-1H-pyrimidin-1-yl}-2-C-methyl-ribofuranose;

β-1-{[4-(2-((1-Isobutanoyloxy-2-methylpropyl)oxycarbonylamino)-ethoxycarbonylamino]-2-oxo-1H-pyrimidin-1-yl}-2-C-methyl-ribofuranose;

β-1-{[4-(2-((1-Pivaloyloxy-2-methylpropyl)oxycarbonylamino)-ethoxycarbonylamino]-2-oxo-1H-pyrimidin-1-yl}-2-C-methyl-ribofuranose;

β-1-{[4-(2-((1-Pivaloyloxyethyl)oxycarbonylamino)-ethoxycarbonylamino]-2-oxo-1H-pyrimidin-1-yl}-2-C-methyl-ribofuranose;

β-1-{[4-(2-((1-Acetoxyethyl)oxycarbonylamino)-ethoxycarbonylamino]-2-oxo-1H-pyrimidin-1-yl}-2-C-methyl-ribofuranose;

β-1-{[4-(2-((Acetoxymethyl)oxycarbonylmethylamino)-ethoxycarbonylamino]-2-oxo-1H-pyrimidin-1-yl}-2-C-methyl-ribofuranose;

β-1-{[4-(2-((1-Isobutanoyloxyethyl)oxycarbonylmethylamino)-ethoxycarbonylamino]-2-oxo-1H-pyrimidin-1-yl}-2-C-methyl-ribofuranose;

β-1-{[4-(2-((1-Acetoxy-2-methylpropyl)oxycarbonylmethylamino)-ethoxycarbonylamino]-2-oxo-1H-pyrimidin-1-yl}-2-C-methyl-ribofuranose;

β-1-{[4-(2-((1-Isobutanoyloxy-2-methylpropyl)oxycarbonylmethylamino)-ethoxycarbonylamino]-2-oxo-1H-pyrimidin-1-yl}-2-C-methyl-ribofuranose;

β-1-{[4-(2-((1-Pivaloyloxy-2-methylpropyl)oxycarbonylmethylamino)-ethoxycarbonylamino]-2-oxo-1H-pyrimidin-1-yl}-2-C-methyl-ribofuranose;

β-1-{[4-(2-((1-Pivaloyloxyethyl)oxycarbonylmethylamino)-ethoxycarbonylamino]-2-oxo-1H-pyrimidin-1-yl}-2-C-methyl-ribofuranose;

β-1-{[4-(2-((1-Acetoxyethyl)oxycarbonylmethylamino)-ethoxycarbonylamino]-2-oxo-1H-pyrimidin-1-yl}-2-C-methyl-ribofuranose;

β-1-{[4-(2-((1-(2,6-Dimethylbenzoyl)oxymethyl)oxycarbonylmethylamino)-ethoxycarbonylamino]-2-oxo-1H-pyrimidin-1-yl}-2-C-methyl-ribofuranose;

β-1-{[4-(2-((1-(2,6-Dimethylbenzoyl)oxy-2-methylpropyl)oxycarbonylmethylamino)-ethoxycarbonylamino]-2-oxo-1H-pyrimidin-1-yl}-2-C-methyl-ribofuranose;

β-1-{[4-(2-((1-(2-Methylbenzoyl)oxy-2-methylpropyl)oxycarbonylmethylamino)-ethoxycarbonylamino]-2-oxo-1H-pyrimidin-1-yl}-2-C-methyl-ribofuranose; and a pharmaceutically acceptable salt of any of the foregoing.

52. A pharmaceutical composition comprising a compound of claim 1 and a pharmaceutically acceptable vehicle.

53. A method of treating a patient infected with hepatitis C comprising administering to a patient in need of such treatment a therapeutically effective amount of a compound of claim 1.

54. A method of treating a patient infected with hepatitis C comprising administering to a patient in need of such treatment a therapeutically effective amount of a pharmaceutical composition of claim 52.

* * * * *